(12) United States Patent
Prusiner et al.

(10) Patent No.: US 6,617,119 B2
(45) Date of Patent: *Sep. 9, 2003

(54) ASSAY FOR SPECIFIC STRAINS OF MULTIPLE DISEASE RELATED CONFORMATIONS OF A PROTEIN

(75) Inventors: Stanley B. Prusiner, San Francisco, CA (US); Jiri G. Safar, Concord, CA (US); Fred E. Cohen, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/901,865

(22) Filed: Jul. 9, 2001

(65) Prior Publication Data

US 2002/0001817 A1 Jan. 3, 2002

Related U.S. Application Data

(63) Continuation of application No. 09/151,057, filed on Sep. 10, 1998, now abandoned, which is a continuation-in-part of application No. 09/026,957, filed on Feb. 20, 1998, now abandoned, which is a continuation-in-part of application No. 08/804,536, filed on Feb. 21, 1997, now Pat. No. 5,891,641.

(51) Int. Cl.$^7$ .................................................. G01N 33/53

(52) U.S. Cl. ................................................ 435/7.1; 435/5

(58) Field of Search ............................................. 436/5, 7.1

(56) References Cited

U.S. PATENT DOCUMENTS

| | | | |
|---|---|---|---|
| 4,300,905 A | 11/1981 | Bleisteiner et al. |
| 4,320,086 A | 3/1982 | Reiss |
| 4,806,627 A | 2/1989 | Wisniewski et al. |
| 5,462,751 A | 10/1995 | Kossovsky et al. |
| 5,521,060 A | 5/1996 | Hoenes et al. |
| 5,565,186 A | 10/1996 | Prusiner et al. |
| 5,757,361 A | 5/1998 | Hirshik |
| 5,846,533 A | 12/1998 | Prusiner et al. |
| 5,858,326 A | 1/1999 | Kisilevsky et al. |
| 5,891,641 A | 4/1999 | Prusiner et al. |
| 5,977,324 A | 11/1999 | Prusiner et al. |
| 6,214,366 B1 | 4/2001 | Prusiner et al. |
| 6,214,565 B1 | 4/2001 | Prusiner et al. |
| 2002/0058031 A1 | 5/2002 | Tung |

FOREIGN PATENT DOCUMENTS

| | | |
|---|---|---|
| AU | 731048 B2 | 11/1997 |
| EP | 0 861 900 A1 | 9/1998 |
| WO | WO 93/10227 | 5/1993 |
| WO | WO 93/23432 | 11/1993 |
| WO | WO 95/31466 | 11/1995 |
| WO | WO 97/16728 | 5/1997 |
| WO | WO 97/40861 | 11/1997 |
| WO | WO 97/43649 | 11/1997 |
| WO | WO 97/46155 | 12/1997 |
| WO | WO 98100441 | 1/1998 |
| WO | WO 98/16834 | 4/1998 |
| WO | WO 98/37411 A | 8/1998 |
| WO | WO 99/42487 | 8/1999 |
| WO | WO 99/42829 | 8/1999 |
| WO | WO 00/02575 | 1/2000 |

OTHER PUBLICATIONS

Alpatova, N.M., et al. "Comparison of Electrochemical Behavior of Heteropolyacids in Solution and Immobilized in a Conducting Polymer Film" Chemical Abstracts, vol. 121, No. 16, Oct. 17, 1994.

Anderson et al., (1996) "Transmission dynamics and epidemiology and BSE in British cattle," *Nature* 382: 779–88.

Barry, R.A., et al., (1986) "Monoclonal Antibodies to the Cellular and Scrapie Prion Proteins," *Journal of Infectious Diseases* 154:518–521.

Basler et al., (1986) "Scrapie and Cellular PrP Isoforms Are Encoded by the Same Chromosomal Gene," *Cell* 46: 417–28.

Bendheim, et al., (1984) "Characterization of Antisera Against Scrapie–Associated Fibrils (SAF) from Affected Hamster and Cross–Reactivity with SAF from Scrapie–Affected Mice and from Patients with Creutzfeldt–Jacob Disease," *J. Gen. Virol.* 66:2471–2478.

Bolton et al., (1992) "Identification of a Protein That Purifies with the Scrapie Prion," *Science* 218:1309–11.

Brown et al., (1992) "'Friendly Fire' in Medicine: Hormones, Homografts, and Creutzfeldt–Jakob Disease," *Lancet* 340:24–27.

Buchanan et al., (1991) "Mortality, Neoplasia, and Creutzfeldt–Jakob Disease in Patients Treated with Human Pituitary Growth Hormone in the United Kingdom", *BMJ* 302:824–828.

Bueler et al., (1992), "Normal Development and Behavior of Mice Lacking the Neuronal Cell–surface PrP Protein," *Nature* 356:577–582.

(List continued on next page.)

Primary Examiner—James Housel
Assistant Examiner—Jeffrey S. Parkin
(74) Attorney, Agent, or Firm—Karl Bozicevic; Bozicevic, Field & Francis LLP

(57) ABSTRACT

Assay methodology of the invention allows for: (1) determining if a sample contains a conformation of a protein which is associated with disease and the concentration and amount of such if present; (2) determining the amount of protease resistant disease related protein in a sample and by subtracting that amount from the total amount of disease related protein present determining the amount of protease sensitive disease protein in the sample; and (3) determining the strain and incubation time of a disease related protein by (i) relating the relative amounts of protease resistant and protease sensitive protein to known strains to thereby determine the strain; and (ii) plotting the concentration of protease sensitive protein on a graph of incubation time versus concentration of protease sensitive protein for known strains to predict the incubation time of an unknown strain of pathogenic protein in a sample.

32 Claims, 19 Drawing Sheets

OTHER PUBLICATIONS

Carter, et al., (1992) "High Level *Escherichia coli* Expression and Production of a Bivalent Humanized Antibody Fragment," *Biotechnology* 10:163–7.

Cochius et al., (1990) "Creutzfeldt–Jakob Disease in a Recipient of Human Pituitary–Derived Gonadotrophin," *Aust. N.Z. J. Med.* 20:592–593.

Cochius et al., (1992) "Creutzfeldt–Jakob Disease in a Recipient of Human Pituitary–Derived Gonadotrophin: A Second Case," *J. Neurol. Neurosurg. Psychiatry* 55:1094–1095.

Collinge, et al., (1996) "Prion protein gene analysis in new variant cases of Creutzfeldt–Jakob disease," *Lancet* 348: 56.

Gabizon, R., et al., "Immunoaffinity Purification and Neutralization of Scrapie Prion Infectivity" Proc. Natl. Acad. Sci. USA, vol. 85, Sep. 1988, pp. 6617–6621.

Gajdusek, D.C., (1977) "Unconventional Viruses and the Origin and Disappearance of Kuru," *Science* 197:943–960.

Gibbs, Jr. et al., (1993) "Creutzfeldt–Jakob Disease Infectivity of Growth Hormone Derived from Human Pituitary Glands," *N. Engl. J. Med.* 328:358–359.

Gioia et al. (1994) "Conformational Polymorphism of the Amyloidogenic and Neurotoxic Peptide Homologous to Residues 106–126 of the Prion Protein." *Journal of Biological Chemistry*, vol. 269(11):7859–7862.

Goldfarb et al., (1992) "Fatal Familial Insomnia and Familial Creutzfeldt–Jakob Disease: Disease Phenotype Determined by a DNA Polymorphism," *Science* 258:806–808.

Healy et al., "Creutzfeldt–Jakob Disease After Pituitary Gonadotrophins: The Prion is the Problem," *BMJ* (1993) 307:517–518.

Hsiao et al., (1994) "Serial transmission in rodents of neurodegeneration from transgenic mice expressing mutant prion protein," *Proc.National Acad. Sci. USA* 91:9126–30.

Kamada, M., et al., "Dispersion and Fixation of 12–Tungstophosphate Anion on a Silica Surface Modified with Silane Agents Having an Amine Group and Their Catalytic Properties" Bull. Chem. Soc. JPN., vol. 66, Dec. 1993, pp. 3565–3570.

Kascsak et al. (1993) "The Role of Antibodies to PRP in the Diagnosis of Transmissible Spongiform Encephalopathies." *Developments in Biological Standardization*, Ch, Basel, vol. 80:141–151.

Kascsak, R.J., et al., (1987) "Mouse Polyclonal and Monoclonal Antibody to Scrapie–Associated Fibril Proteins" *Journal of Virology* 61:3688–3693.

Kimberlin, R.H., et al. "Suppression of Scrapie Infection In Mice by Heteropolyanion 23, Dextran Sulfate, and Some Other Polyanions" Antimicrobial Agents and Chemotherapy, vol. 30, No. 3, Sep. 1986, pp. 409–413.

Lasmezas et al., (1993) "Recombinant Human Growth Hormone and Insulin–Like Growth Factor I Induce PRP Gene Expression in PC12 Cell," *Biochem. Biophys. Res. Commun.* 196:1163–1169.

McKinley et al., (1983) "A Protease–Resistant Protein is a Structural Component of the Scrapie Prion," *Cell* 35:57–62.

Mehlhorn et al., (1996) "High–Level Expression and Characterization of a Purified 142–Residue Polypeptide of the Prion Protein," *Biochemistry* 35:5528–37.

Meyer et al., (1986) "Separation and Properties of Cellular and Scrapie Prion Proteins," *Proc. Natl. Acad. Sci. USA* 83:2310–2314.

Nguyen et al., (1986) "Prion Protein Peptides Induce Alpha–helix to Beta–Sheet Conformational Transitions." *Biochemistry*, pp. 4186–4192.

Oesch, et al., (1985) "A Cellular Gene Encodes Scrapie PrP 27–30 Protein," *Cell* 40:735–46.

Pan, et al., (1992) "Purification and Properties of the Cellular Prion Protein from Syrian Hamster Brain," *Protein Sci.* 1:1343–1352.

Pan, et al., (1993) "Conversion of a α–helices into β–sheets features in the formation of the scrapie prion proteins," *Proc. Natl. Acad. Sci. USA* 90:10962–66.

Prusiner et al. (1993) "Immunologic and Molecular Biologic Studies of Prion Proteins in Bovine Spongiform Encephalopathy." *Journal of Infectious Diseases*, vol. 167:602–613.

Prusiner, S.B. et al., "Biology of Prions," *The Molecular and Genetic Basis of Neurological Disease*, 2nd Edition, Chap. 7, pp. 103–143.

Prusiner, S.B., et al., (1983) "Scrapie prions aggregate to form amyloid–like birefringent rods," *Cell* 35:349–58.

Rogers et al., (1991) "Epitope Mapping of the Syrian Hamster Prion Protein Utilizing Chimeric and Mutant Genes in a Vaccinia Virus Expression System," *J. Immunol.* 147:3568–74.

Rogers, et al., (1993) "Conversion of truncated and elongated prion proteins into the scrapie isoform in cultured cells," *Proc. Natl. Acad. Sci. USA* 90:3182–6.

Safar et al. J., (1993) "Conformational Transitions, Dissociation, and Unfolding of Scrapie Amyloid (Prion) Protein," *J. Biol. Chem.* 268:20276–84.

Safar, et al., (1990) "Scrapie–associated precursor proteins: Antigenic relationship between species and immunocytochemical localization in normal, scrapie, and Creutzfeldt–Jakob disease brains," *Neurology* 40:513–7.

Safar, J., et al., "Eight Prion Strains Have $PrP_{Sc}$ Molecules With Different Conformations" Nature Medicine, vol. 4, No. 10, Oct. 1998, pp. 1157–1165.

Saidkhanov, S.S., et al. "Changes in Catalytic Properties of 12–Heteropolyacids in Reaction of Dihydrogen Evolution From Water Induced By Their Immobilization on Anion–Exchange Polymers" Journal of Molecular Catalysis, vol. 21, 1983, pp. 365–373.

Schmerr, Mary Jo et al., (1996) "Improvements in a Competition Assay to Detect Scrapie Prion Protein by Capillary Eletrophoresis", *Journal of Chromatography b* 681:29–35.

Serban et al, (1990) "Rapid Detection of Creuzfeldt–Jakob Disease and Scrapie Prion Proteins," *Neurology* 40:110–7.

Stahl et al., (1993) "Structural Studies of the Scrapie Prion Protein Using Mass Spectrometry and Amino Acid Sequencing," *Biochemistry* 32:1991–2002.

Taraboulos et al., (1992) "Regional Mapping of Prion Proteins in Brain," *Proc. Natl. Acad. Sci. USA* 89:7620–7624.

Turk, et al., (1988) "Purification and Properties of the Cellular and Scrapie Hamster Prion Proteins," *Eur. J. Biochem.* 176:21–30.

Wilesmith and Wells, (1991) "Bovine Spongiform Encephalopathy," *Curr. Topics Microbiol. Immunol.* 172 21–38.

Wilesmith, "Bovine Spongiform Encephalopathy," *Methods in Molecular Medicines: Prion Diseases*, pp. 155–173.

Williamson, et al., (1996) "Circumventing tolerance to generate autologous monoclonal antibodies to the prion protein," *Proc. Natl. Acad. Sci. USA* 93:7279–82.

Williamson, R.A. et al., (1998) "Mapping the prion protein using recombinant antibodies", J. Virol. 72(11):9413–9418.

Xu, Y., et al., (1997) "Cryptic and regulatory epitopes in CD13/Aminopeptidase N", Exp. Hematol. 25:521–529.

Yokoyama, Takashi, et al., (1996) "Immunoreactivity of Specific Epitopes of PrP$^{Sc}$ is Enhanced by Pretreatment in a Hydrated Autoclave", *Clinical and Diagnostic Laboratory Immunology* 3(4):470–471.

Bessen et al. (1992) "Biochemical and Physical Properties of the Prion Protein from Two Strains of the Transmissible Mink Encephalopathy Agent." *J. Virol.* 66(4):2096–2101.

Bessen et al. (1992) "Identification of two biologically distinct strains of transmissible mink encephalopathy in hamsters." *J. Gen. Virol.* 73:329–334.

Collinge et al. (1996) "Molecular analysis of prion strain variation and the aetiology of 'new variant' CJD." *Nature* 383:685–690.

Hill et al. (1997) "Diagnosis of new variant Creutzfeldt–Jakob disease by tonsil biopsy." *The Lancet* 349:99–100.

Karlsson et al. (1991) "Analysis and isolation of human transferrin receptor using the OKT–9 monoclonal antibody covalently crosslinked to magnetic beads" *Anal. Biochem.* 199:219–222.

Kelly (1996) "Alternative conformations of amyloidogenic proteins govern their behavior." *Curr. Op. Struct. Biol.* 6:11–17.

Korth et al. (1997) "Prion (PrP$^{Sc}$)–specific epitope defined by a monoclonal antibody" *Nature* 390:74–77.

Lai et al. (1996) "The Acid–Mediated Denaturation Pathway of Transthyretin Yields a Conformational Intermediate that Can Self–Assemble into Amyloid." *Biochem*.35:6470–6482.

Marsh et al. (1994) "Physiochemical and biological characterization of distinct strains of the transmissible mink encephalopathy agent." *Phil. Tran. R. Soc. Lond. B.* 343:413–414 .

Max, E.E. (1999) "Immunoglobulins: Molecular Genetics" in: Fundamental Immunology, Fourth Ed., Paul, W.F., ed., Lippincott–Raven Publishers, Philadelphia, PA, pp. 142–143.

McCutchen et al. (1993) "Intermolecular Disulfide Linkages are not Required for Transthyretin Amyloid Fibril Formation in vitro." *Biochem. Biophys. Res. Comm.* 197(2):415–421.

McCutchen et al. (1993) "Transthyretin Mutation Leu–55–Pro Significantly Alters Tetramer Stability and Increases Amyloidogenicity." *Biochem*32:12119–12127.

Medori et al. (1992) "Fatal Familial Insomnia, a Prion Disease with a mutation at codon 178 of the prion protein gene." *N. Engl. J. Med.* 326:444–449.

Milroy et al. (1996) "Inhibiting transthyretin amyloid fribril formation via protein stabilization." *Proc. Natl. Acad. Sci. USA* 93:15051–15056.

Prusiner et al. (1997) "The prion diseases of humans and animals" in: *The Molecular and Genetic Basis of Neurological Disease*, 2$^{nd}$ ed., Rosenberg et al., eds. Butterworth–Heinemann, Chapter 9.

Prusiner et al. (1982) "Further Purification and Characterization of Scrapie Prions." *Biochem.* 21:6942–6950.

Setchel, C.H. (1985) "Magnetic separations in biotechnology—A Review" *J. Chem. Tech. Biotechnol.* 35B:175–182.

Somerville et al. (1997) "Biochemical typing of scrapie strains." *Nature* 386(6625):564.

Telling et al. (1996) "Interactions between wild–type and mutant prion proteins modulate neurodegeneration in transgenic mice." *Genes Devel.* 10:1736–1750.

Telling et al. (1996) "Evidence for the Conformation of the Pathologic Isoform of the Prion Protein Enciphering and Propagating Prion Diversity." *Science* 274:2079–2082.

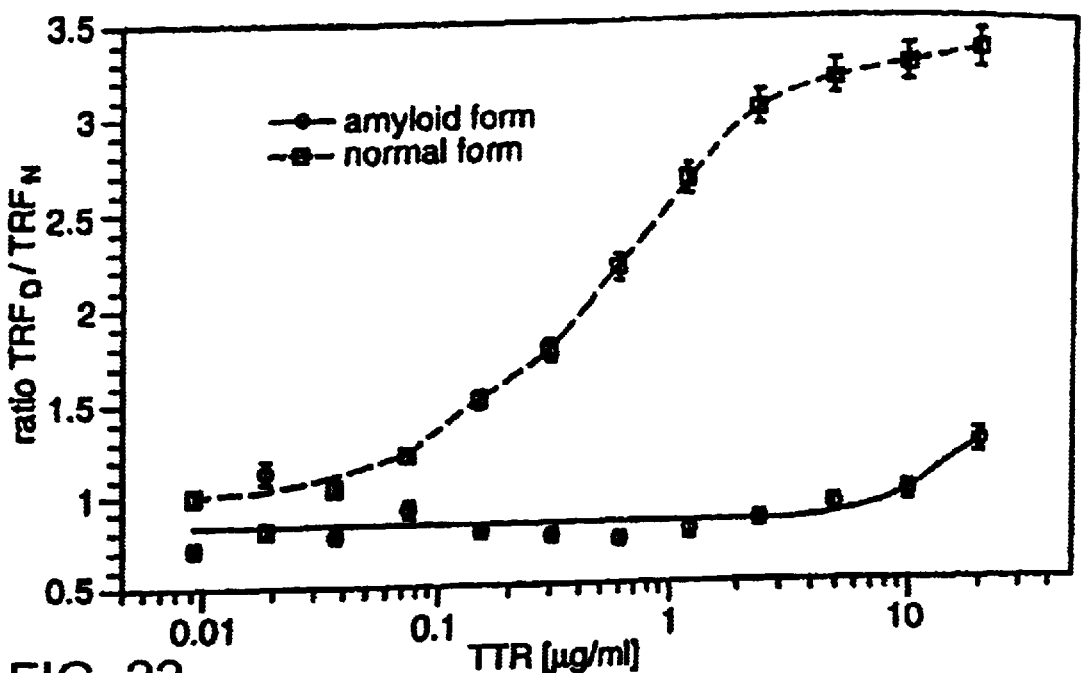
FIG. 22
a) $F_n = F_{nN} + F_{nA}$ → $F_{nN} = F_n - F_{nA}$
b) $F_d = F_{dN} + F_{dA}$
$\Delta F_{n \to d} = \Delta F_{Nn \to d} + \Delta F_{An \to d}$
$\Delta F_{An \to d} = F_d - \Delta F_{Nn \to d}$
$[TTR_A] \sim \Delta F_{An \to d} = (F_n \cdot f_{Nn \to d}) - F_d$
FIG. 23
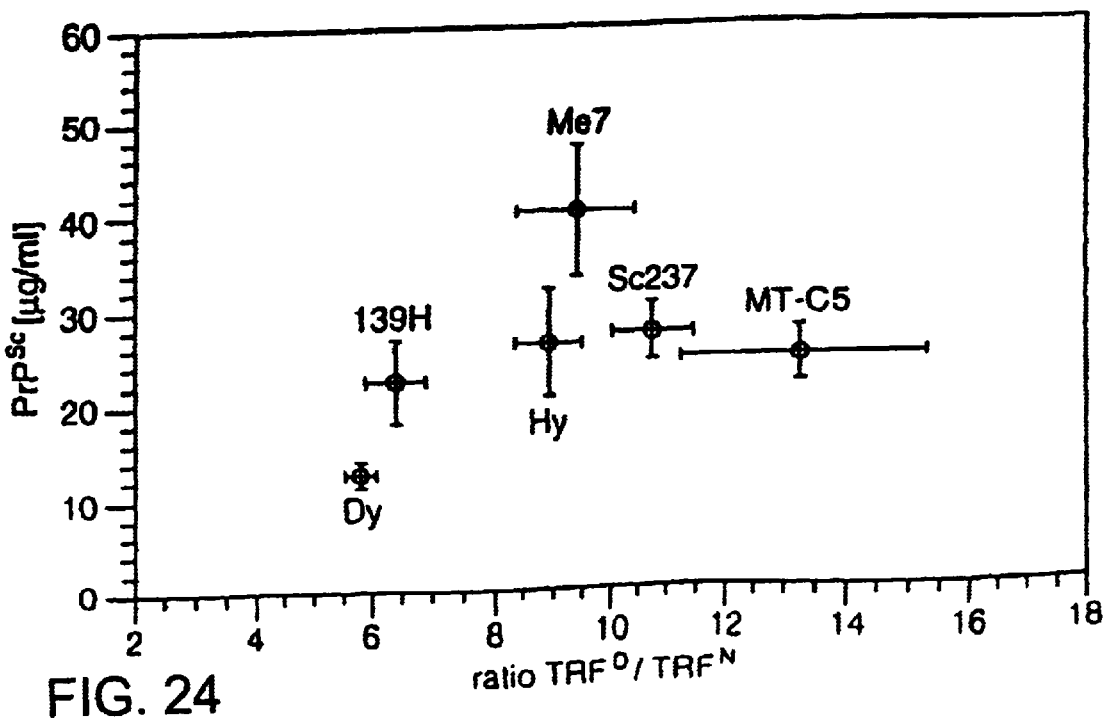
FIG. 24

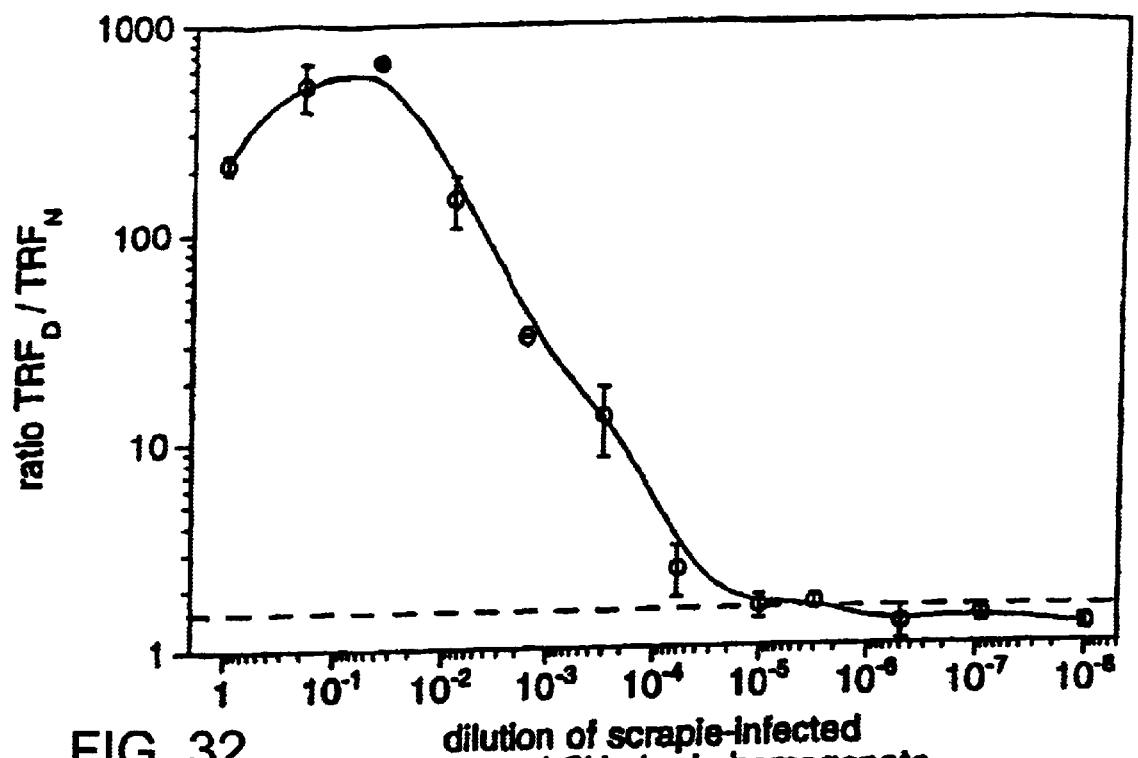
FIG. 32  dilution of scrapie-infected into normal SHa brain homogenate
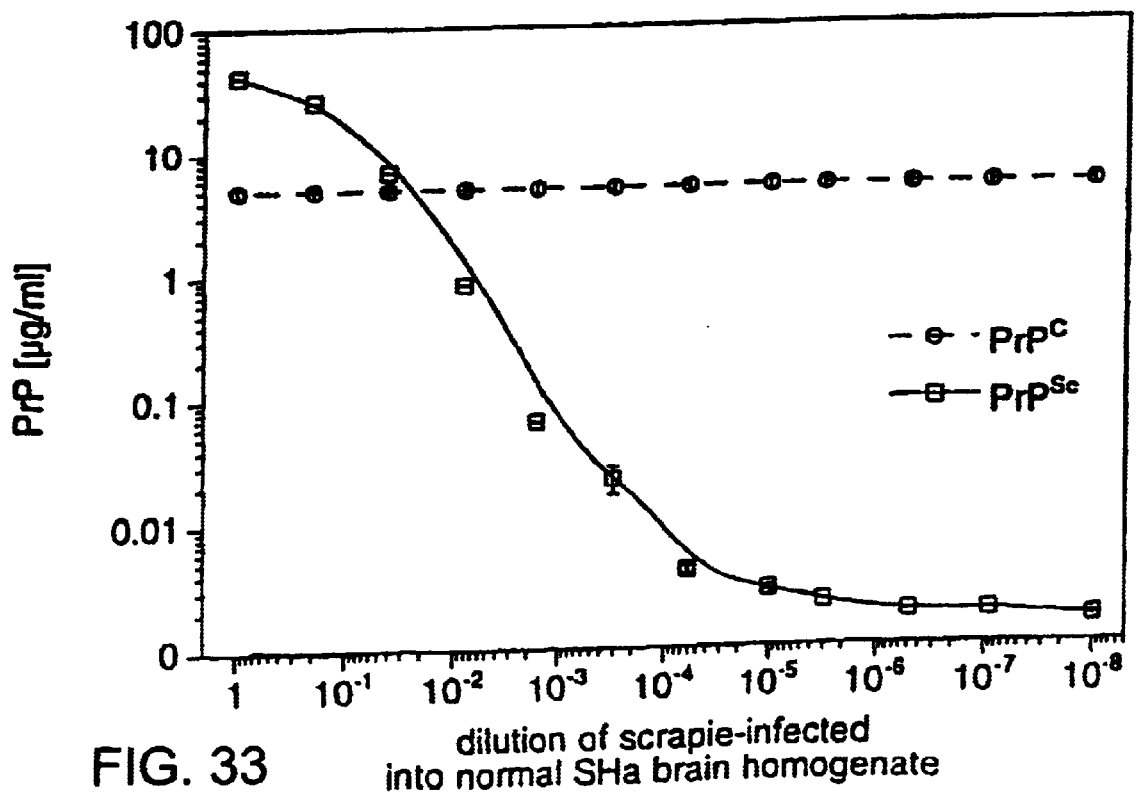
FIG. 33  dilution of scrapie-infected into normal SHa brain homogenate

ASSAY FOR SPECIFIC STRAINS OF MULTIPLE DISEASE RELATED CONFORMATIONS OF A PROTEIN

CROSS-REFERENCE

This application is a continuation application of Ser. No. 09/151,057, filed Sep. 10, 1998 (now abandoned), which is a continuation-in-part application of Ser. No. 09/026,957, filed Feb. 20, 1998 now abandoned, which is a continuation-in-part application of Ser. No. 08/804,536, filed Feb. 21, 1997 now issued U.S. Pat. No. 5,891,641, issued Apr. 6, 1999, all of which are incorporated herein by reference in their entirety and to which applications we claim priority under 35 U.S.C. §120.

FIELD OF THE INVENTION

This invention relates generally to immunoassays. More particularly the invention relates to an assay which allows for detection of a specific strain of a disease related conformational form of a protein (such as $PrP^{Sc}$) which may have very low antibody binding affinity.

BACKGROUND OF THE INVENTION

Prions are infectious pathogens that cause invariably fatal prion diseases (spongiform encephalopathies) of the central nervous system in humans and animals. Prions differ significantly from bacteria, viruses and viroids. The dominating hypothesis is that no nucleic acid is necessary to allow for the infectivity of a prion protein to proceed.

A major step in the study of prions and the diseases they cause was the discovery and purification of a protein designated prion protein [Bolton, McKinley et al. (1982) *Science* 218:1309–1311; Prusiner, Bolton et al. (1982) *Biochemistry* 21:6942–6950; McKinley, Bolton et al. (1983) *Cell* 35:57–62]. Complete prion protein-encoding genes have since been cloned, sequenced and expressed in transgenic animals. $PrP^C$ is encoded by a single-copy host gene [Basler, Oesch et al. (1986) *Cell* 46:417–428] and when $PrP^C$ is expressed it is generally found on the outer surface of neurons. Many lines of evidence indicate that prion diseases results from the transformation of the normal form of prion protein ($PrP^C$) into the abnormal form ($PrP^{Sc}$). There is no detectable difference in the amino acid sequence of the two forms. However, $PrP^{Sc}$ when compared with $PrP^C$ has a conformation with higher β-sheet and lower α-helix content [Pan, Baldwin et al. (1993) *Proc Natl Acad Sci USA* 90:10962–10966; Safar, Roller et al. (1993) *J Biol Chem* 268:20276–20284]. The presence of the abnormal $PrP^{Sc}$ form in the brains of infected humans or animals is the only disease-specific diagnostic marker of prion diseases.

$PrP^{Sc}$ plays a key role in both transmission and pathogenesis of prion diseases (spongiform encephalopathies) and it is a critical factor in neuronal degeneration [Prusiner (1997) The Molecular and Genetic Basis of Neurological Disease, 2nd Edition: 103–143]. The most common prion diseases in animals are scrapie of sheep and goats and bovine spongiform encephalopathy (BSE) of cattle [Wilesmith and Wells (1991) *Curr Top Microbiol Immunol* 172:21–38]. Four prion diseases of humans have been identified: (1) kuru, (2) Creutzfeldt-Jakob Disease (CJD), (3) Gerstmann-Streussler-Sheinker Disease (GSS), and (4) fatal familial insomnia (FFI) [Gajdusek (1977) *Science* 197:943–960; Medori, Tritschler et al. (1992) *N Engl J Med* 326:444–449]. Initially, the presentation of the inherited human prion diseases posed a conundrum which has since been explained by the cellular genetic origin of PrP.

Prions exist in multiple isolates (strains) with distinct biological characteristics when these different strains infect in genetically identical hosts [Prusiner (1997) The Molecular and Genetic Basis of Neurological Disease, 2nd Edition: 165–186]. The strains differ by incubation time, by topology of accumulation of $PrP^{Sc}$ protein, and in some cases also by distribution and characteristics of brain pathology [DeArmond and Prusiner (1997) Greenfield's Neuropathology, 6th Edition:235–280]. Because $PrP^{Sc}$ is the major, and very probably the only component of prions, the existence of prion strains has posed a conundrum as to how biological information can be enciphered in a molecule other than one comprised of nucleic acids. The partial proteolytic treatment of brain homogenates containing some prion isolates has been found to generate peptides with slightly different electrophoretic mobilities [Bessen and Marsh (1992) *J Virol* 66:2096–2101; Bessen and Marsh (1992) *J Gen Virol* 73:329–334; Telling, Parchi et al. (1996) *Science* 274:2079–2082]. These findings suggested different proteolytic cleavage sites due to the different conformation of $PrP^{Sc}$ molecules in different strains of prions. Alternatively, the observed differences could be explained by formation of different complexes with other molecules, forming distinct cleavage sites in $PrP^{Sc}$ in different strains [Marsh and Bessen (1994) *Phil Trans R Soc Lond B* 343:413–414]. Some researchers have proposed that different prion isolates may differ in the glycosylation patterns of prion protein [Collinge, Sidle et al. (1996) *Nature* 383:685–690; Hill, Zeidler et al. (1997) *Lancet* 349:99–100]. However, the reliability of both glycosylation and peptide mapping patterns in diagnostics of multiple prion strains is currently still debated [Collings, Hill et al. (1997) *Nature* 386:564; Somerville, Chong et al. (1997) *Nature* 386:564].

A system for detecting $PrP^{Sc}$ by enhancing immunoreactivity after denaturation is provided in Serban, et al., Neurology, Vol. 40, No. 1, Ja 1990. Sufficiently sensitive and specific direct assay for infectious $PrP^{Sc}$ in biological samples could potentially abolish the need for animal inoculations completely. Unfortunately, such does not appear to be possible with current $PrP^{Sc}$ assays—it is estimated that the current sensitivity limit of proteinase-K and Western blot-based $PrP^{Sc}$ detection is in a range of 1 μg/ml which corresponds to $10^4$–$10^5$ prion infectious units. Additionally, the specificity of the traditional proteinase-K-based assays for $PrP^{Sc}$ is in question in light of recent findings of only relative or no proteinase-K resistance of undoubtedly infectious prion preparations [Hsiao, Groth et al. (1994) *Proc Natl Acad Sci USA* 91:9126–9130] Telling, et al. (1996) *Genes & Dev.*

Human transthyretin (TTR) is a normal plasma protein composed of four identical, predominantly β-sheet structured units, and serves as a transporter of hormone thyroxine. Abnormal self assembly of TTR into amyloid fibrils causes two forms of human diseases, namely senile systemic amyloidosis (SSA) and familial amyloid polyneuropathy (FAP) [Kelly (1996) *Curr Opin Strut Biol* 1):11–7]. The cause of amyloid formation in FAP are point mutations in the TTR gene; the cause of SSA is unknown. The clinical diagnosis is established histologically by detecting deposits of amyloid in situ in biopsy material.

To date, little is known about the mechanism of TTR conversion into amyloid in vivo. However, several laboratories have demonstrated that amyloid conversion may be simulated in vitro by partial denaturation of normal human TTR [McCutchen, Colon et al. (1993) *Biochemistry* 32(45):12119–27; McCutchen and Kelly (1993) *Biochem Biophys Res Commun* 197(2) 415–21]. The mechanism of conformational transition involves monomeric conformational intermediate which polymerizes into linear β-sheet structured amyloid fibrils [Lai, Colon et al. (1996) *Biochemistry* 35(20):6470–82]. The process can be mitigated by binding with stabilizing molecules such as thyroxine or triiodophenol [Miroy, Lai et al. (1996) *Proc Natl Acad Sci USA* 93(26): 15051–6].

In view of the above points, there is clearly a need for a specific, high flow-through, and cost-effective assay for testing sample materials for the presence of specific strains of a pathogenic protein including transthyretin and prion protein.

SUMMARY OF THE INVENTION

Assay methodology of the invention allows for: (1) determining if a sample contains a conformation of a protein which is associated with disease and the concentration and amount of such if present; (2) determining the amount of a chemical compound such as a protease resistant disease related protein in a sample and by subtracting that amount from the total amount of disease related protein present determining the amount of protease sensitive disease protein in the sample; and (3) determining the strain and incubation time of a disease related protein by (i) relating the relative amounts of protease resistant and protease sensitive protein to known strains to thereby determine the strain; and (ii) plotting the concentration of protease sensitive protein on a graph of incubation time versus concentration of protease sensitive protein for known strains to predict the incubation time of a given unknown strain.

The presence and concentration of protein in a disease related conformation is determined via one of three different basic methods. Pursuant to the primary method a sample first is divided into two portions. A first portion is contacted with a labeled antibody which binds to the non-disease conformation of the protein but not to the disease related conformation of the protein. The second portion is then subjected to a protein unfolding treatment which increases the binding affinity for any protein in the second conformation for the antibody. In general the protein unfolding treatment will expose an epitope to which the antibody can bind which epitope is unexposed in the disease related conformation. Accordingly, disease related protein which did not bind the antibody prior to the protein unfolding treatment will now bind the antibody. A comparison is then made between the amount of antibody binding to protein in the first untreated portion with the amount of antibody binding to protein in the second portion. A difference between the amount of antibody binding in the first and second portions indicates the presence of disease related protein in the sample. Depending on the protein and the protein unfolding treatment used it may be necessary to make an adjustment due to the effect of the treatment one protein in the non-disease related conformation.

Stated in a step-by-step manner the basic assay method of the invention comprises (a) providing a sample suspected of containing a protein (having a first conformation and a second, disease-related conformation), (b) dividing the sample into first and second portions, (c) contacting the first portion with an antibody that binds to the first conformation with higher affinity than to the second conformation, (d) subjecting the second portion to a protein unfolding treatment to cause any protein in the second conformation to adopt a different conformation having a higher affinity for the antibody, (e) contacting the second portion with the antibody, (f) determining the relative levels of antibody binding to said first and second portions, and (g) determining the presence or absence of protein in the second conformation based on the comparison.

Once it has been determined that a sample contains protein in disease related conformation it is further useful to determine the strain in relationship to incubation time of the protein. This can be done by obtaining another portion of the sample which tested positive for protein in the disease related conformation. This portion is subjected to limited protease treatment which hydrolyzes most protein in the sample but for highly resistant protein in the disease related conformation, e.g. protease resistant PrP 27–30. The concentration and amount of the treatment resistant protein is then determined. By subtracting the amount of treatment resistant protein in the sample from the total amount of disease related protein in the sample one obtains the amount of disease related protein in the sample which is sensitive to protease digestion, e.g. protease sensitive $PrP^{Sc}$. Each strain of disease related protein has a known ratio of total protein in the disease related conformation (e.g. native $PrP^{Sc}$) to amount of protein in disease related conformation which is denatured by a protein denaturing treatment (protease sensitive $PrP^{Sc}$). Thus, the (total: denatured) ratio can be matched to that of a known strain to determine the strain in a sample.

The method of determining the strain of any disease conformation of a protein can also be stated in a step-by-step fashion. The method is carried out by (a) isolating protein in the disease related formation, e.g. by centrifugation; (b) treating the isolated protein with a compound (e.g. guanidine hydrochloride) which denatures one form of the isolated protein but not another; (c) determining the ratio of protein resistant to the treatment relative to the total amount of disease related protein; and (d) comparing the ratio to that of a predetermined standard of a known strain thereby determining the strain of disease related protein in a sample This method is more readily applied when the strain found matches to a known strain. If there is no match to a known strain and no experimental error was made, it may be assumed that a new strain has been discovered.

The incubation time of a disease related conformation of a protein can be determined even if the strain is previously unknown. This is determined by (a) isolating protein in the disease related formation, e.g. by centrifugation; (b) treating the isolated protein (e.g. with proteinase K) which hydrolyzes one form of the isolated protein but not another; (c) subtracting the amount of disease related protein not denatured (treatment resistant protein) from the total amount of disease related protein to find the amount of disease related protein which is denatured; (d) plotting the amount of disease related (treatment sensitive) protein found in (c) on a graph of incubation time versus amount of disease related protein not denatured (which graph has plotted known strains with known incubation times); and (e) thereby predict the incubation time.

The assay of the invention is useful in assaying samples which contain proteins which are present in at least two conformations (e.g., a native non-disease conformation and a disease conformation) and are present at levels of $1\times10^3$ particles/ml or less. The present invention utilizes antibodies which do not bind or have a relatively low degree of affinity for the tightly configured disease-conformation of the protein. One useful antibody for binding to $PrP^C$ is the monoclonal antibody 3F4 produced by the hybridoma cell line ATCC HB9222 deposited on Oct. 8, 1986 in the American Type Culture Collection, 12301 Parklawn Drive, Rockville, Md. 20852 and disclosed and described in U.S. Pat. No.

4,806,627 issued Feb. 21, 1989—incorporated by reference to disclose antibodies which selectively bind $PrP^C$. In addition to antibody other binding partners which bind the non-disease related conformation but not the disease related conformation could be used in the assay of the invention. Antibodies such as 3F4 and others used in the assays described in the examples are commercially available.

To demonstrate the primary method behind the present invention one begins with a starting sample which is divided into at least two portions. The first portion is contacted with labeled antibodies without treating the proteins and the second portion is treated with labeled antibodies after the proteins have been subjected to a protein unfolding treatment which causes any proteins in the disease conformation to assume a conformation which has a higher degree of binding affinity for the antibodies (e.g. exposes a previously unexposed epitope). The readings are compared (i.e., one subtracted from the other) and the presence of proteins in the disease related conformation are deduced based on the difference between the two readings.

Pursuant to a second embodiment of the basic assay, it is possible to utilize the basic concept behind the present invention without obtaining two readings for each assay. This can be done by establishing a standard based on carrying out the assay on a statistically significant number of closely related samples. After the standard has been established one will know the level of antibody binding which should be observed when a given sample does not contain any proteins in the disease related conformation. Using the standard, one then subjects a sample to be tested to a protein unfolding treatment so as to convert any proteins in the disease related conformation to a different conformation which has a much higher degree of binding affinity for the label antibodies. The measurement obtained is then compared with the standard. If the difference between the standard and the measurement obtained is outside of a given range it can be deduced that the original sample included proteins in the disease related conformation. These results could be confirmed (1) via the first embodiment described above and/or (2) by testing the sample with an antibody which binds only the disease related conformation of the protein—see US96/14840.

A third embodiment of the invention can utilize either of the embodiments disclosed above along with the formulae provided herein in order to calculate (quantitatively) the number of proteins (concentration) in the disease related conformation present within the original sample.

In accordance with any of the assay embodiments it is preferable to pre-treat the sample being tested to (1) remove as many contaminant proteins as possible, and (2) increase the concentration of disease related protein in the sample relative to the non-disease related conformation of the protein. For example, the initial sample can be chemically treated with a compound which preferentially degrades or denatures contaminant proteins and/or the relaxed, non-disease form of the protein and/or is exposed to antibodies which preferentially bind to (in order to remove) contaminants and/or non-disease conformation of the protein.

It may be possible to enhance further the sensitivity of various aspects of the invention by concentrating the disease conformation of a protein by adding a compound which selectively binds to the disease conformation to form a complex and centrifuging the sample to precipitate out the complex which is then tested in accordance with the methods described here. Specifics regarding such concentration methods are described in detail in our co-pending application Ser. No. 09/026,967 entitled "Process for Concentrating Protein with Disease-Related Conformation".

The different embodiments of the assay of the invention described above are all "direct" types of immunoassays—meaning that the sample is directly assayed with the labeled antibody either with or without treatment to change the conformation of any disease related conformation proteins present in the sample. An "indirect" assay may also be used. For example, it may be desirable to enhance the number of disease related proteins in the sample (if any) by the use of a transgenic mouse and thereby enhance any signal obtained. To carry out these embodiments of the invention, the sample is first used to inoculate a transgenic mouse which has had its genome modified so that it will develop symptoms of disease when inoculated with proteins in the disease related conformation. After the mice are inoculated, a sufficient period of time is allowed to pass (e.g., 30 days) after which the transgenic animal is sacrificed and a sample such as homogenized brain tissue from the mouse is used in the direct assay described above. The present invention enhances the ability of transgenic mice to detect prions by shortening the period of time which must pass until a determination can be made as to whether the original sample included proteins in the disease related conformation. It would also be possible to use mice of the type disclosed and described in any of U.S. Pat. Nos. 5,565,186; 5,763,740; or 5,792,901 or to apply epitope tagged PrP as disclosed in U.S. Pat. No. 5,750,361 (incorporated by reference) to affinity purify the $PrP^{Sc}$ from the brain of a Tg mouse and thereafter apply the assay of the present invention. Without the present invention the mouse is inoculated and one must wait until the inoculated mouse actually demonstrates symptoms of the disease. Depending on the mouse, this can take several months or even years. Any of the assays of the present invention could be used with any transgenic mice such as those described above. The assay could be used well before the mouse developed symptoms of disease thereby shortening the time needed to determine if a sample includes infectious proteins.

The assay methodology of the present invention can be applied to any type of sample when the sample is suspected of containing a protein which occurs in at least two conformations. The protein must occur in one conformation which binds to known antibodies, antibodies which can be generated or other specific binding partners. The second conformation must be sufficiently different from the first conformation in terms of its binding affinity so that the two conformations can be distinguished by using antibodies or binding partners which have a much higher degree of affinity for the first conformation than for the second conformation. In its conceptually simplest form, the invention works best when a known labeled antibody binds to a non-disease form of a protein with a high degree of affinity, and does not bind (or binds with an extremely low degree of affinity) to the same protein when it is present in its disease related conformation. However, in reality, a given protein may have more than two conformations. The protein may have more than one non-disease conformation and more than one disease related conformation, (Telling, et al., *Science* (1996)). The invention is still useful when multiple conformations of non-disease and disease forms of the protein exist—provided that (1) at least one non-disease conformation differs from at least one disease conformation in terms of its binding affinity; and (2) it is possible to treat the disease related conformation of the protein so as to substantially enhance its binding affinity.

As indicated above, the assay of the invention can be used to assay any type of sample for any type of protein, provided the protein includes a non-disease and a disease related conformation. However, the invention was particularly developed to assay samples for the presence of (1) PrP proteins and determine whether the sample included a PrP protein in its disease conformation, i.e., included $PrP^{Sc}$ (2) insoluble forms of βA4 associated with Alzheimer's disease and (3) transthyretin. Accordingly, much of the following disclosure is directed to using the immunoassay of the present invention to detect the presence of either $PrP^{Sc}$ (or to a lesser degree βA4 or transthyretin (TTR)) in a sample—it being understood that the same general concepts are applicable to detecting disease related conformations of a wide range of different types of proteins. Further, the disclosure is particularly directed to describing how to determine the incubation time and the particular strain of infectious prions ($PrP^{Sc}$) in a sample—it being understood that the same general concepts are applicable to determining the incubation time and particular strain of other constricted proteins associated with different diseases.

The present method of $PrP^{Sc}$ detection was developed by labeling selected purified IgG with Europium. Antibodies used (3F4) have a high binding affinity for $PrP^{C}$ (non-disease conformation) which comprises an α-helical rich conformation. The antibodies have a low binding affinity for $PrP^{Sc}$ (disease conformation) which comprises a β-sheet rich conformation. The IgG may be obtained from common monoclonal, polyclonal, or recombinant antibodies, typically recognizing the sequence 90–145 of $PrP^{C}$ and conformationally unfolded prion protein. Different conformations of recombinant prion protein were chemically crosslinked to polystyrene plates through a glutaraldehyde activation step. The relative affinities of the Eu-labeled IgG with α-helical, β-sheet, and random coil conformation of recombinant Syrian hamster prion protein corresponding to sequence 90–231 were determined by time-resolved, dissociation-enhanced fluorescence in a 96-well polystyrene plate format.

A determination of the relative affinities of different labeled antibodies for proteins can be made by different methods. However, the disease related conformation of a protein is often present in a very low concentration relative to that of the non-disease conformation. Accordingly, it often requires very sensitive methods to detect any increase caused by the treatment of the disease conformation of the protein. Time-resolved, dissociation-enhanced fluorescence and more preferably dual wavelength, laser-driven fluorometers are particularly useful devices—see Hemmilä et al., Boianalytical Applications of Labeling Technologies (eds. Hemmilä) 113–119 (Wallas Oy. Turku, Finland, 1995).

By carefully calibrating this method, it is possible to detect the signal increase in antibody reactivity in the transition from β-sheet conformational state to denatured state. This signal is relatively large compared to that obtained from the transformation from its native α-helical to the treated relaxed, or denatured state. Thus, the original conformational state of prion protein can be assigned by the differential assay in native and treated states. When a sample containing no β-sheet rich protein is treated some increase is obtained in immunoreactivity. This amount of increase must be adjusted for and after doing such the resulting concentration or amount is referred to the "adjusted amount." The amount of antibody-specific binding over that obtained for α-helical conformation of $PrP^{C}$ (beyond the adjusted amount) is a measure of the presence of the β-sheet rich conformation which is essential for pathogenicity and infectivity of $PrP^{Sc}$.

An aspect of the invention is to provide an immunoassay which is applicable to assaying samples containing proteins, which samples are suspected of containing a protein which occurs within a native non-disease conformation and a disease related conformation (e.g., PrP protein, βA4 protein and transthyretin).

Another aspect of the invention is to provide an assay which differentiates between (1) disease related proteins or portions thereof which are not hydrolyzed by limited protease treatment with a protease such as proteinase K (protease resistant proteins, e g PrP 27–30) and (2) disease related proteins which are hydrolyzed by a limited protease treatment with a protease such as proteinase K (e g., protease-sensitive $PrP^{Sc}$).

Another aspect is to provide a method for determining the ratio of total native disease related protein to disease related protein which is denatured by protein denaturing treatment.

An advantage of the invention is that it allows for detection of disease related protein (e.g., protease sensitive $PrP^{Sc}$) which is hydrolyzed during protease digestion of the non-disease, native protein (e.g., $PrP^{C}$) and thus which would not be detected via conventional Western Blot methodologies.

A feature of the invention is that it can be used to calculate the incubation time of an infectious protein.

An advantage of the present invention is that the immunoassay can quickly and accurately determine the presence of proteins in the disease related conformation (e.g., $PrP^{Sc}$, βA4 and transthyretin) even though the antibody used in the assay does not bind or has a very low degree of binding affinity for the protein in the disease related conformation and the disease related conformation is present in a lower concentration than the non-disease conformation.

Another object of the invention is to provide an assay which makes it possible to not only determine (1) whether a pathogenic particle is present in a sample but (2) determine the concentration of the particles in a sample, (3) determine the particular strain of particle present, and (4) the incubation time.

A feature of the invention is that the signal obtained can be enhanced by the use of transgenic animals, e.g., mice which are used to detect the presence of a protein in a sample.

Another feature is that time-resolved, dissociation-enhanced fluorescence or a dual wavelength, laser driven fluorometer can be used to enhance sensitivity.

Another advantage is that the assay can detect levels of the disease causing conformation of a protein at a concentration of $1\times10^3$ particles/ml or less.

A specific object is to provide a diagnostic assay for determining the presence of infectious prion protein in variable sample materials obtained or derived from human, primate, monkey, pig, bovine, sheep, deer, elk, cat, dog, mouse, and chicken tissues and/or body fluids.

Another specific object is to provide a diagnostic assay for determining the presence of βA4 protein in variable sample materials obtained or derived from human, primate, monkey, pig, bovine, sheep, deer, elk, cat, dog, mouse, and chicken tissues and/or body fluids.

Another object is to provide a rapid assay for native infectious prion protein in the brains of transgenic and non-transgenic animals injected with sample material potentially containing prions.

Another object is to provide a method to evaluate decontamination procedures by assaying the level of denaturation of pathogenic proteins (e.g., prions or β-sheet βA4) after such treatments.

Another object is to provide a rapid method for screening different compounds to evaluate their potential for treating diseases associated with disease conformations of different proteins such as by screening compounds for their stabilizing effect on different protein conformations (e.g., $PrP^C$ or α-helical conformation of βA4) or their destabilizing impact on the pathogenic conformation (e.g., $PrP^{Sc}$ or β-sheet conformation of βA4) of a protein.

Another object is to provide a rapid method for screening different pharmaceutical compounds with potential for prion disease treatment such as by screening compounds for their stabilizing effect on α-helical conformation of a normal isoform of the $PrP^C$ protein or their destabilizing impact on the β-sheet conformation of the pathogenic isoform of the $PrP^{Sc}$ protein.

Another advantage is that the process can be carried out without an antibody directly able to recognize an infectious conformation of a protein, and without using a proteinase K step to eliminate the signal of normal (non-disease) isoforms of the protein such as $PrP^C$.

Another advantage is that in the invented process there is no need for the antibody directly able to recognize pathogenic conformation of βA4 or transthyretin.

An important feature of the assay is the rapid, cost effective and high flow-through design which can be designed with the capacity to screen 96 samples per day per 96 well plate.

Another aspect of the invention is the diagnostic method to quantitatively detect TTR in the abnormal, amyloid conformation in sample material obtained from human and animal tissues, body fluids, and pharmaceuticals. The invented process provides a direct, sensitive method to distinguish and quantify the normal and amyloid conformations of TTR in a mixture present in sample materials.

The quantitation is based on a measurement of the difference in affinities of monoclonal or polyclonal antibodies with TTR in normal or amyloid conformation against random coil conformation. The present invention describes three methods of evaluation and the mathematical formula used for such quantification.

An important object is to provide specific diagnostic assay for pathogenic TTR in variable sample materials obtained or derived from human, primate, monkey, pig bovine, sheep, deer, elk, cat, dog, and chicken tissues.

Another object is to provide a rapid assay for amyloid form of TTR in transgenic animals.

Another object is to provide a rapid method to screen different pharmaceutical compounds with potential for treatment of senile systemic amyloidosis (SSA) and familial amyloidotic polyneuropathy (FAP). Such compounds are screened for their stabilizing effect on normal conformation of TTR or their destabilizing impact on the amyloid conformation of TTR Still another object is to provide a rapid method to screen the impact of different spontaneous and designed mutations in the TTR gene on conformation, stability and amyloid formation of such TTR gene products in transgenic animals harboring natural or artificial APP genes.

The specific advantage is that invented assay may detect a pathogenic forms of TTR in a mixture with denatured nonpathogenic forms of the same or in a mixture with a soluble form of TTR—for example, detect less than $1 \times 10^3$ particles per ml.

These and other objects, advantages, and features of the invented process will become apparent to those skilled in the art upon reading the details of the assay method, antibody development and testing, and transgenic mouse as more fully described below with reference to the attached figures.

BRIEF DESCRIPTION OF THE DRAWINGS

FIG. 10 is a graph showing the total amount of PrP proteins in scrapie infected hamster brains and the amount of β-sheet PrP$^{Sc}$ in both brains calculated from the model wherein the data points and bars represent average±SEM obtained from four independent measurements. The concentration of SHaPrP on the ordinate was calculated from formula (1). The samples of 5% (w/v) brain homogenates obtained from normal or scrapie-infected Syrian hamsters were serially diluted into 5% (w/v) Prnp$^{0/0}$ mouse homogenate. Data points and bars represent average±SEM obtained from four independent measurements;

FIG. 11 is a graph showing the correlation of the infectivity and amount of β-sheet form of SHaPrP$^{Sc}$ as calculated from the direct assay and formula wherein purified SHaPrP$^{Sc}$ was sonicated in the presence of 5% PrP$^{0/0}$ mouse brain homogenate and diluted as described and wherein the data points and bars represent average±SEM obtained from four independent measurements.

FIG. 22 shows the ratio between signals of denatured and native TTR in normal and amyloid conformations, developed as described above. The data points and bars represent average±SEM obtained from four independent measurements;

FIG. 23: Modified formula for calculating the amount of TTR in amyloid conformation from the data obtained by direct assay with anti-TTR polyclonal antibody The changes from general equation reflect the reversed ratio of denatured and native states for normal and amyloid forms of TTR. The difference between the fluorescence of denatured state of the sample and that expected for transition from native normal protein to denatured state is proportionate to the amount of TTR in amyloid conformation. $F_n$–total signal of native conformation; $F_{nN}$ and $F_{nA}$–the signals of native normal and amyloid conformations, respectively; $F_d$–total signal of TTR in denatured state; $F_{dN}$ and $F_{dA}$ are the signals of denatured normal or amyloid states of TTR; $\Delta F_{n \rightarrow d}$–the total increase of the signal in the transition from native to denatured states; $\Delta F_{Nn \rightarrow d}$–increase in the signal of normal conformation in the transition from native to denatured state; $\Delta F_{An \rightarrow d}$–change in the signal of amyloid conformation in the transition from native to denatured state; $f_{Nn \rightarrow d}$–correlation factor for the transition from native to denatured state of normal TTR;

FIG. 24 is a graph of the "prion index" (which is the ratio of antibody binding to denatured vs. native PrP protein) vs. the concentration of PrP$^{Sc}$ in μg/ml. The results shown represent the average±SEM obtained from three different brains of LVG/LAK Syrian hamsters infected with different prion strains;

FIGS. 26–29 are all graphs used to distinguish eight strains of PrP$^{Sc}$ via the immunoassay of the invention wherein:

FIG. 26 is a bar graph of total PrP compared to PrP$^{Sc}$. The columns and bars represent the average±SEM obtained from three different brains of LVG/LAK Syrian hamsters infected with different prion strains and measured in three independent experiments, FIG. 27 is a graph showing the ratio of antibody binding to denatured/native PrP and a function of concentration of PrP$^{Sc}$ in the brains of Syrian hamsters infected with different prion strains. The concentration of PrP$^{Sc}$ (formula 1) and the ratio of antibody binding to denatured/native PrP were measured by the conformation-dependent immunoassay;

FIG. 28 is a graph of brain homogenates of Syrian hamsters inoculated with different scrapie strains and uninoculated controls, denoted C, were digested with 50 μg/ml of proteinase K for 2 h at 37° C. prior to the conformation-dependent immunoassay;

FIG. 29 is a graph of incubation time plotted as a function of the concentration of the proteinase K-sensitive fraction of PrP$^{Sc}$ ([PrP$^{Sc}$]–[PrP 27–30]);

FIGS. 30 and 31 are graphs showing the equilibrium dissociation and unfolding of PrP$^C$ and PrP$^{Sc}$ in three prion strains. Ratio of antibody binding to denatured/native PrP and apparent fractional change of unfolding of prion proteins during equilibrium dissociation and unfolding, wherein:

FIG. 30 is a graph of data from the brains of uninoculated controls (C) and Syrian hamsters infected with Sc237, DY, and HY strains of prions analyzed by the conformation-dependent immunoassay; the ratio of antibody binding to denatured/native PrP is plotted as a function of the GdnHCl concentration;

FIG. 31 is a graph of such data showing the apparent fractional change unfolding ($F_{app}$) of PrP$^{Sc}$ from the Sc237, DY, and HY strains. The points and bars represent the average±SEM obtained from four different measurements;

FIGS. 32 and 33 are graphs showing the dynamic range and sensitivity of the ratio of antibody binding to PrP in denatured and native states. Homogenates [5%(w/v)] prepared from the brains of Syrian hamsters exhibiting signs of CNS dysfunction ~70 d after inoculation with Sc237 prions were serially diluted into 5% (w/v) normal SHa brain homogenate, and the presence of PrP$^{Sc}$ was measured after NaPTA precipitation by the conformation-dependent immunoassay, wherein:

FIG. 32 is a graph showing the ratio of the fluorescence signals of denatured and native aliquots plotted as a function of the dilution of scrapie-infected brain homogenate;

FIG. 33 is a graph wherein the absolute amount of PrP$^C$ and PrP$^{Sc}$ was calculated from formula (1) and plotted as a function of the dilution of scrapie-infected brain homogenate. The data points and bars represent average±SEM obtained from four independent measurements;

FIGS. 34 and 35 are all graphs showing incubation time for eight strains of PrP$^{Sc}$, wherein:

FIG. 34 shows each strain plotted as incubation time versus total PrP$^{Sc}$;

FIG. 35 shows each strain plotted as incubation time versus treatment or protease resistant PrP$^{Sc}$ which is PrP 27–30;

Figure 29:
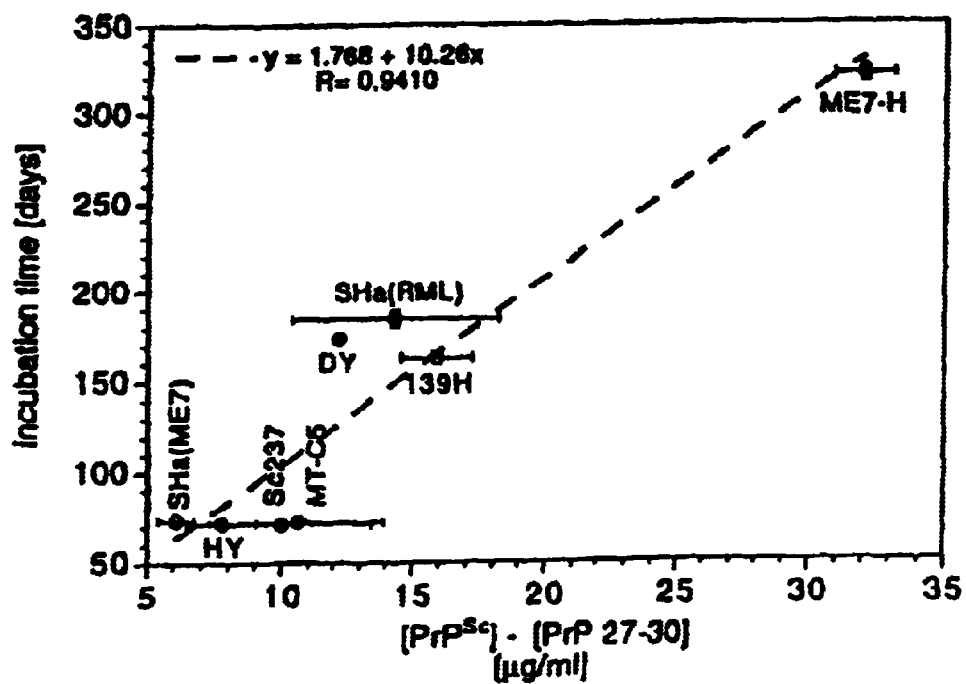
Figure 30:
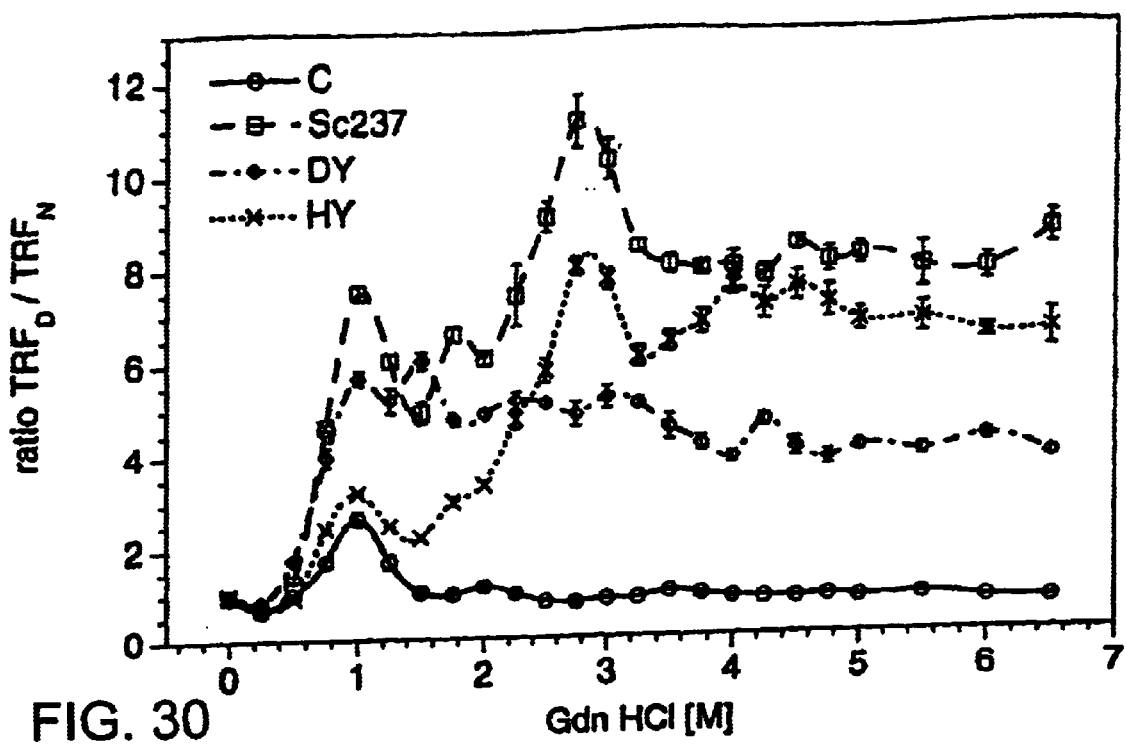
Figure 31:
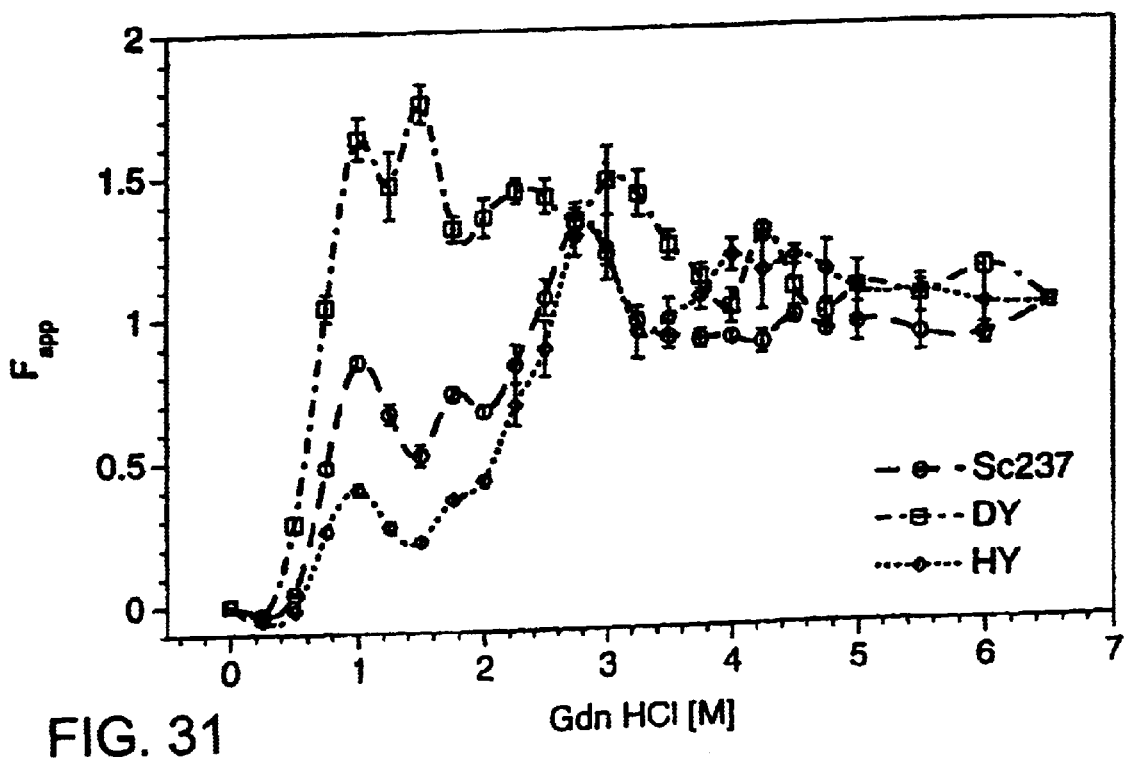
Figure 34:
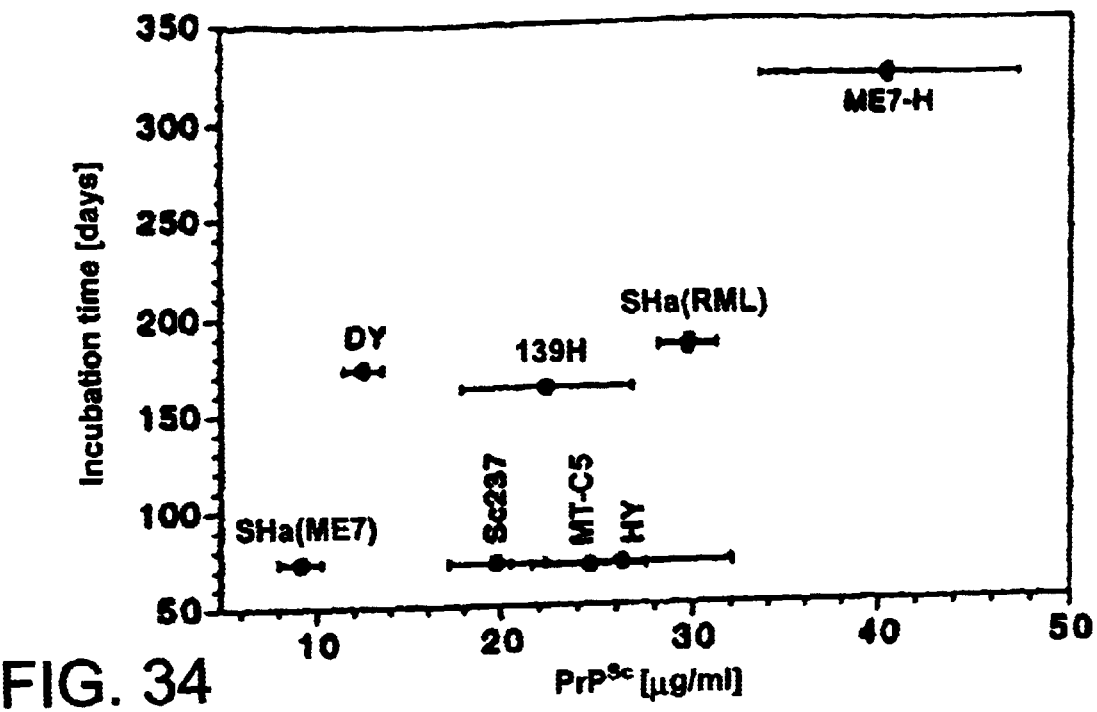
Figure 35:
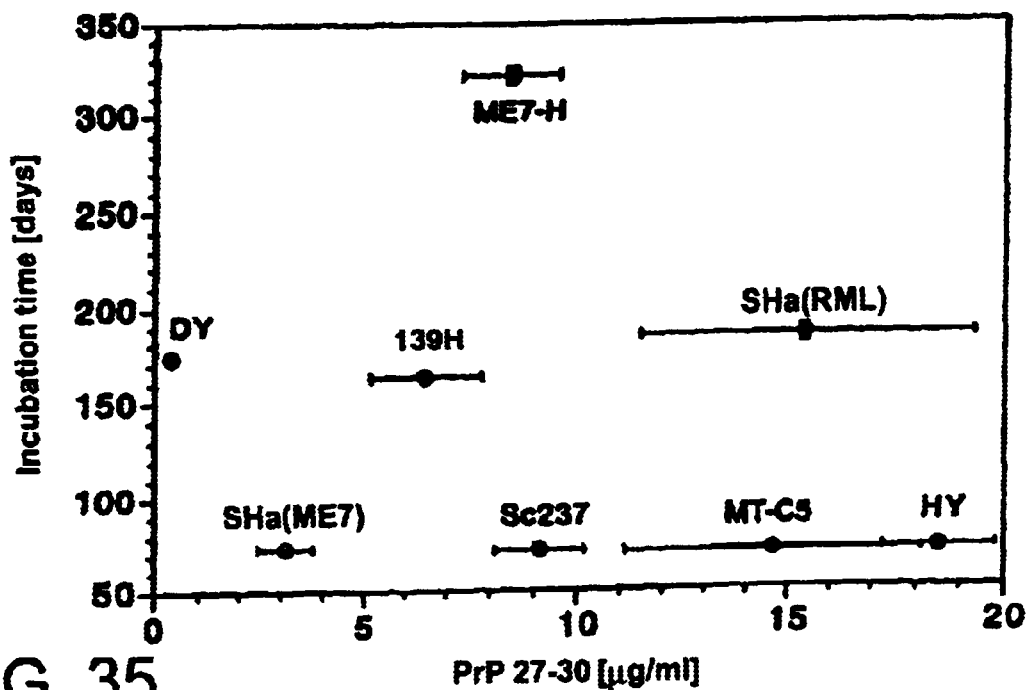

It is most interesting to compare FIGS. 34 and 35 where no correlation of PrP$^{Sc}$ or PrP 27–30 with incubation time is evident with FIG. 29 which shows a linear relationship for data plotting incubation time versus treatment or protease sensitive PrP$^{Sc}$, i.e. incubation time versus (total PrP$^{Sc}$–PrP 27–30) where PrP 27–30 is the protease resistant PrP$^{Sc}$.

DETAILED DESCRIPTION OF THE PREFERRED EMBODIMENTS

Before the present assays and methods are disclosed and described, it is to be understood that this invention is not limited to particular antibodies, proteins, labels, assays or method as such may, of course vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are provided solely for the disclosure prior to the filing date of the present application Nothing herein is to be construed as an admission that the present invention is not entitled to antedate such publication by virtue of prior invention. Further, the dates of publication provided are subject to change if it is found that the actual date of publication is different from that provided here.

Definitions

The terms "protein" as used herein is intended to encompass any amino acid sequence and include modified sequences such as glycoproteins. The term includes naturally occurring proteins and peptides as well as those which are recombinantly or synthetically synthesized. As used in connection with the present invention the term "protein" is specifically intended to cover naturally occurring proteins which occur in at least two different conformations wherein both conformations have the same or substantially the same amino acid sequence but have different three dimensional structures. The two conformations of the protein include at least one conformation which is not related to a disease state and at least one conformation which is related to a disease state—pathogenic. A specific and preferred example of a protein as used in connection with this disclosure is a PrP protein which includes the non-disease form referred to as the PrP$^c$ form and the disease related form referred as the PrP$^{Sc}$. Although a prion protein or the PrP$^{Sc}$ form of a PrP protein is infectious and pathogenic, the disease conformation of other proteins is not infectious although it is pathogenic. As used herein, the term pathogenic may mean that the protein actually causes the disease or it may simply mean that the protein is associated with the disease and therefore is present when the disease is present. Thus, a pathogenic protein as used in connection with this disclosure is not necessarily a protein which is the specific causative agent of a disease.

Samples being assayed may contain a number of different proteins and the proteins of these samples are treated via one or more different types of treatment as described below to obtain a desired result.

"Pretreatment" is used here to describe the most gentle of the different types of treatment applied in the assays of the invention. Pretreatment is optionally carried out early in the method to denature or hydrolyze proteins which are (1) easily hydrolyzed or denatured and (2) not of the same general type as the proteins of interest. The pretreatment is carried out to break up contaminate protein so that they can be more easily removed from the sample containing proteins of interest. Gentle treatment with low concentrations of a protease for a short period could be used for pretreatment. The pretreatment can remove contaminant proteins by other means such as by contacting a sample with antibodies which bind to contaminant proteins expected to be present in the sample.

The terms "protein unfolding treatment" or "unfolding treatment" or "denaturing" and the like are used interchangeably here to describe a process whereby a sample or portion thereof and specifically proteins in the disease conformation of the sample are physically and/or chemically manipulated so that proteins in the sample in a disease related conformation are caused to unfold to some degree, i.e. changed to a different conformation with a higher binding affinity with a binding partner such as an antibody, e.g. by exposing a previously unexposed or partially exposed epitope. Proteins treated in this manner are also referred to as proteins in a relaxed conformation which conformation increases the binding affinity of the protein to a binding partner such as an antibody. Unfolding treatment includes subjecting the sample to heat, pressure and/or chemicals. In a preferred embodiment, samples containing PrP$^{Sc}$ (which is the disease-related conformation comprising β-sheet structural configurations) are treated (e.g. with guanidine hydrochloride) so that the protein assumes a different conformation (e.g., comprising an α-helical configuration and/or a random coil configuration) having four times or more greater antibody binding affinity.

"Limited protease treatment" means treating a protein sample such that all or substantially all of the proteins but for those most resistant to the treatment (e.g. protease resistant $PrP^{Sc}$—i.e. PrP 27–30) are hydrolyzed or broken into pieces, i.e. small peptides and/or amino acids. This type of lytic treatment is carried out in order to hydrolyze proteins of interest in the non-disease configuration as well as protein of interest in the disease conformation which are "sensitive" to the limited protease treatment. The only proteins not hydrolyzed by limited protease treatment are proteins of interest in the disease conformation which are "resistant" to this treatment (e.g. PrP 27–30).

Some trial and error is expected in determining the parameters (e.g. temperature, time, protease type and concentration) needed to obtain the desired type of treatment. Gentle conditions for pretreatment, medium for unfolding and harsh for limited protease treatment.

The terms "PrP protein", "PrP" and like are used interchangeably herein and shall mean both the infectious particle form $PrP^{Sc}$ known to cause diseases (spongiform encephalopathies) in humans and animals and the noninfectious form $PrP^C$ which, under appropriate conditions is converted to the infectious $PrP^{Sc}$ form. The terms "prion", "prion protein" and "$PrP^{Sc}$ protein" and the like we used interchangeably herein to refer to the infectious $PrP^{Sc}$ form of PrP, and is a contraction of the words "protein" and "infection." Particles are comprised largely, if not exclusively, of $PrP^{Sc}$ molecules encoded by a PrP gene. Prions are distinct from bacteria, viruses and viroids. Known prions infect animals to cause scrapie, a transmissible, degenerative disease of the nervous system of sheep and goats, as well as bovine spongiform encephalopathy (BSE), or "mad cow disease", and feline spongiform encephalopathy of cats. Four prion diseases known to affect humans are (1) kuru, (2) Creutzfeldt-Jakob Disease (CJD), (3) Gerstmann-Straussler-Scheinker Disease (GSS), and (4) fatal familial insomnia (FFI). As used herein "prion" includes all forms of prions causing all or any of these diseases or others in any animals used—and in particular in humans and domesticated farm animals.

The term "PrP gene" is used herein to describe genetic material which expresses proteins including known polymorphisms and pathogenic mutations The term "PrP gene" refers generally to any gene of any species which encodes any form of a PrP protein. Some commonly known PrP sequences are described in Gabriel et al., *Proc Natl. Acad Sci. USA* 89:9097–9101 (1992), and U.S. Pat. Nos. 5,565, 186; 5,763,740; 5,792,901; and WO97/04814, incorporated herein by reference to disclose and describe such sequences. The PrP gene can be from any animal, including the "host" and "test" animals described herein and any and all polymorphisms and mutations thereof, it being recognized that the terms include other such PrP genes that are yet to be discovered. The protein expressed by such a gene can assume either a $PrP^C$ (non-disease) or $PrP^{Sc}$ (disease) form.

The term "antibody" stands for an immunoglobulin protein which is capable of binding an antigen. Antibody as used herein is meant to include the entire antibody as well as any antibody fragments (e.g. F(ab)', Fab, Fv) capable of binding the epitope, antigen or antigenic fragment of interest. Preferred antibodies for assays of the invention are immunoreactive or immunospecific for and therefore specifically and selectively bind to a protein of interest e.g., an A4β amyloid protein or a PrP protein. Antibodies which are immunoreactive and immunospecific for both the native non-disease form and the treated disease form but not for the untreated disease form, (e.g., for both native $PrP^{C}$ and treated $PrP^{Sc}$ but not native $PrP^{Sc}$) are preferred. Antibodies for PrP are preferably immunospecific—e.g., not substantially cross-reactive with related materials. Some specific antibodies which can be used in connection with the invention are disclosed in published PCT application WO 97/10505 which is incorporated herein by reference to disclose and describe antibodies. This published PCT application corresponds to U.S. Ser. No. 08/713,939 also incorporated herein by reference. Antibodies disclosed in the PCT application which selectively bind $PrP^{Sc}$ should not be used to carry out the basic assay of the present invention but could be used to confirm the presence of $PrP^{Sc}$ when other proteins are denatured. The term "antibody" encompasses all types of antibodies, e.g. polyclonal, monoclonal, and those produced by the phage display methodology. Particularly preferred antibodies of the invention are antibodies which have a relatively high degree of affinity for both native $PrP^{C}$ and treated $PrP^{Sc}$ but a relatively low degree of or substantially no binding affinity for $PrP^{Sc}$. More specifically, antibodies of the invention preferably have four times or more, more preferably fifteen times or more, and still more preferably 30 times or more binding affinity for both native $PrP^{C}$ and denatured $PrP^{Sc}$ as compared with the binding affinity for native $PrP^{Sc}$.

One useful antibody for binding to $PrP^{C}$ is the monoclonal antibody 263K 3F4 produced by the hybridoma cell line ATCC HB9222 deposited on Oct. 8, 1986 in the American Type Culture Collection, 12301 Parklawn Drive, Rockville, Md. 20852 and disclosed and described in U.S. Pat. No. 4,806,627 issued Feb. 21, 1989—incorporated by reference to disclose antibodies which selectively bind $PrP^{c}$.

"Purified antibody" refers to that which is sufficiently free of other proteins, carbohydrates, and lipids with which it is naturally associated. Such an antibody "preferentially binds" to a treated or denatured disease conformation of a protein such as the β-sheet conformation of A4β or $PrP^{Sc}$ protein (or an antigenic fragment thereof), and does not substantially recognize or bind to other antigenically unrelated molecules. A purified antibody of the invention is preferably immunoreactive with and immunospecific for a specific species and more preferably immunospecific for native $PrP^{C}$ and for treated or denatured forms of $PrP^{C}$ and $PrP^{Sc}$ but not for native or untreated $PrP^{Sc}$.

"Antigenic fragment" of a protein (e.g., a PrP protein) is meant a portion of such a protein which is capable of binding an antibody.

By "binds specifically" is meant high avidity and/or high affinity binding of an antibody to a specific polypeptide e.g., epitope of a protein, e.g., a $PrP^{C}$ or A4β protein. Antibody binding to its epitope on this specific polypeptide is preferably stronger than binding of the same antibody to any other epitope, particularly those which may be present in molecules in association with, or in the same sample, as the specific polypeptide of interest e.g., binds more strongly to epitope fragments of a protein such as $PrP^{Sc}$ so that by adjusting binding conditions the antibody binds almost exclusively to an epitope site or fragments of a desired protein such as an epitope fragment exposed by treatment of $PrP^{Sc}$ and not exposed on native untreated $PrP^{Sc}$.

By "detectably labeled antibody", "detectably labeled anti-PrP" or "detectably labeled anti-PrP fragment" is meant an antibody (or antibody fragment which retains binding specificity), having an attached detectable label. The detectable label is normally attached by chemical conjugation, but where the label is a polypeptide, it could alternatively be attached by genetic engineering techniques. Methods for production of detectably labeled proteins are well known in the art. Detectable labels known in the art, but normally are radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/ diaminobenzidine, avidin/streptavidin, luciferase/luciferin), methods for labeling antibodies, and methods for using labeled antibodies are well known in the art (see, for example, Harlow and Lane, eds. (Antibodies: A Laboratory Manual (1988) Cold Spring Harbor Laboratory Press, Cold Spring Harbor, N.Y.)). Europium is a particularly preferred label.

Abbreviations used herein include:
CNS for central nervous system;
BSE for bovine spongiform encephalopathy;
CJD for Creutzfeldt-Jacob Disease;
FFI for fatal familial insomnia;
GdnHCl for Guanidine hydrochloride;
GSS for Gerstamnn-Strassler-Scheinker Disease;
Hu for human;
HuPrP for human prion protein;
Mo for mouse;
MoPrP for mouse prion protein;
SHa for a Syrian hamster;
SHaPrP for a Syrian hamster prion protein;
Tg for transgenic;
Tg(SHaPrP) for a transgenic mouse containing the PrP gene of a Syrian hamster;
Tg(HuPrP) for transgenic mice containing the complete human PrP gene;
Tg(ShePrP) for transgenic mice containing the complete sheep PrP gene;
Tg(BovPrP) for transgenic mice containing the complete cow PrP gene;
$PrP^{Sc}$ for the scrapie isoform of the prion protein;
$PrP^C$ for the cellular contained common, normal isoform of the prion protein;
PrP 27–30 or $PrP^{Sc}$ 27–30 for the treatment or protease resistant form of $PrP^{Sc}$;
$MoPrP^{Sc}$ for the scrapie isoform of the mouse prion protein;
MHu2M for a chimeric mouse/human PrP gene wherein a region of the mouse PrP gene is replaced by a corresponding human sequence which differs from mouse PrP at 9 codons;
Tg(MHu2M) mice are transgenic mice of the invention which include the chimeric MHu2M gene;
$MHu2MPrP^{Sc}$ for the scrapie isoform of the chimeric human/mouse PrP gene;
$PrP^{CJD}$ for the CJD isoform of a PrP protein;
$Prnp^{0/0}$ for ablation of both alleles of an endogenous prion protein gene, e.g., the MoPrP gene,
$Tg(SHaPrP^{+/0})81/Pmp^{0/0}$ for a particular line (81) of transgenic mice expressing SHaPrP, +/0 indicates heterozygous;
$Tg(HuPrP)/Prnp^{0/0}$ for a hybrid mouse obtained by crossing a mouse with a human prion protein gene (HuPrP with a mouse with both alleles of the endogenous prion protein gene disrupted;
$Tg(MHu2M)/Prnp^{0/0}$ for a hybrid mouse obtained by crossing a mouse with a chimeric prion protein gene (MHu2M) with a mouse with both alleles of the endogenous prion protein gene disrupted;

TTR for transthyretin;
FVB for a standard inbred strain of mice often used in the production of transgenic mice since eggs of FVB mice are relatively large and tolerate microinjection of exogenous DNA relatively well;
[$PrP_\beta$]—concentration of prion protein in β-sheet conformation;
[$\beta A4_\beta$]—concentration of βA4 in β-sheet conformation;
[DRC]—concentration of a disease related conformation of a protein.

General Aspects of the Invention

The assay method comprises providing a sample suspected of containing a protein which assumes a first conformation and a second disease related conformation and is capable of detecting a disease conformation of the protein when present in a very low concentration relative to the concentration of the non-disease conformation. The sample is divided into a first portion and a second portion. The first portion is preferably bound to the surface of the solid support and thereafter brought into contact with a labeled antibody. The antibody is of a type which binds to the protein in its first conformation with a higher (four times or more) degree of affinity than it binds to the protein in its second disease related conformation. The second portion of the sample is then subjected to unfolding treatment which causes any protein in the second, disease related conformation to assume a different conformation which conformation has a higher degree of affinity (four times or more higher) for the labeled antibody as compared with the affinity for the protein in the untreated second disease related conformation. The second portion (subjected to the unfolding treatment) is then, preferably, bound to the surface of the solid support. The treated protein bound to the support is then contacted with a labeled antibody under conditions which allow the antibody to bind to proteins in the first conformation or proteins in the unfolded conformation.

After the labeled antibodies have been provided with sufficient time, temperature and chemical conditions (e.g., pH) to bind to the appropriate proteins present in the respective portions the level of binding of the labeled antibody to protein in each portion is determined. A highly sensitive assay is used such as an assay involving time-resolved, dissociation-enhanced fluorescence or dual wavelength, laser-driven fluorometer making it possible to detect concentrations in an amount in the range of about $1 \times 10^3$ particles per ml or less. A high degree of sensitivity is required because in most samples the concentration of protein in the disease conformation will be very low in comparison to the concentration of the protein in the non-disease conformation, e.g., 3 orders of magnitude or more different. For example, the non-disease conformation of the protein might be present in an amount of about $1 \times 10^8$ particles/ml while the disease conformation of the protein is only present in an amount of $1 \times 10^4$ particles/ml. Thus, any increase in signal noted due to subjecting the disease conformation of the protein to unfolding treatment will be very small relative to the signal being obtained from the protein in the non-disease conformation.

After the level of binding for both portions of sample is obtained, the levels are compared. For example, the level of binding of labeled antibody to a protein in the first portion is subtracted from the level of binding of antibody to a protein in the second portion. The difference between the two reflects the amount of protein present in the original sample which was in the second, disease related conformation—after adjusting for differences caused (if any) by increasing the binding affinity of protein in the first portion.

Figure 3:
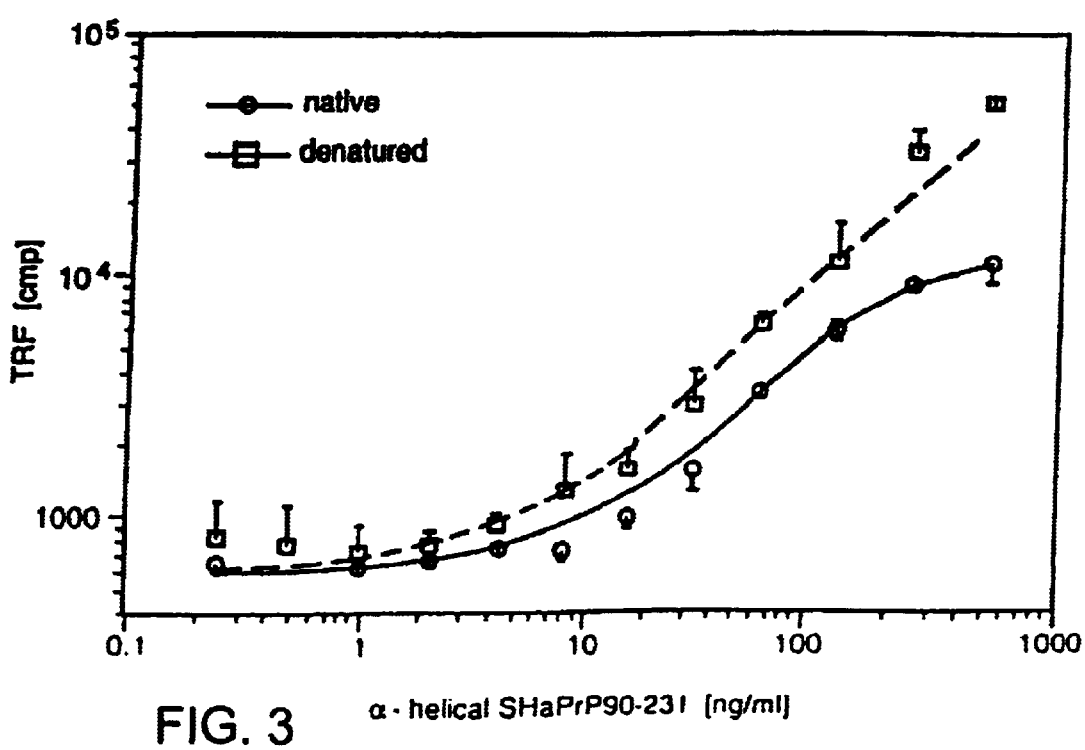
FIG. 3 is a graph showing the calibration of a direct assay with recombinant SHaPrP90–231 in α-helical conformation, in the presence of 5% $PrP^{0/0}$ mouse brain homogenate wherein the data points and bars represent average±SEM obtained from four independent measurements.
Figure 4:
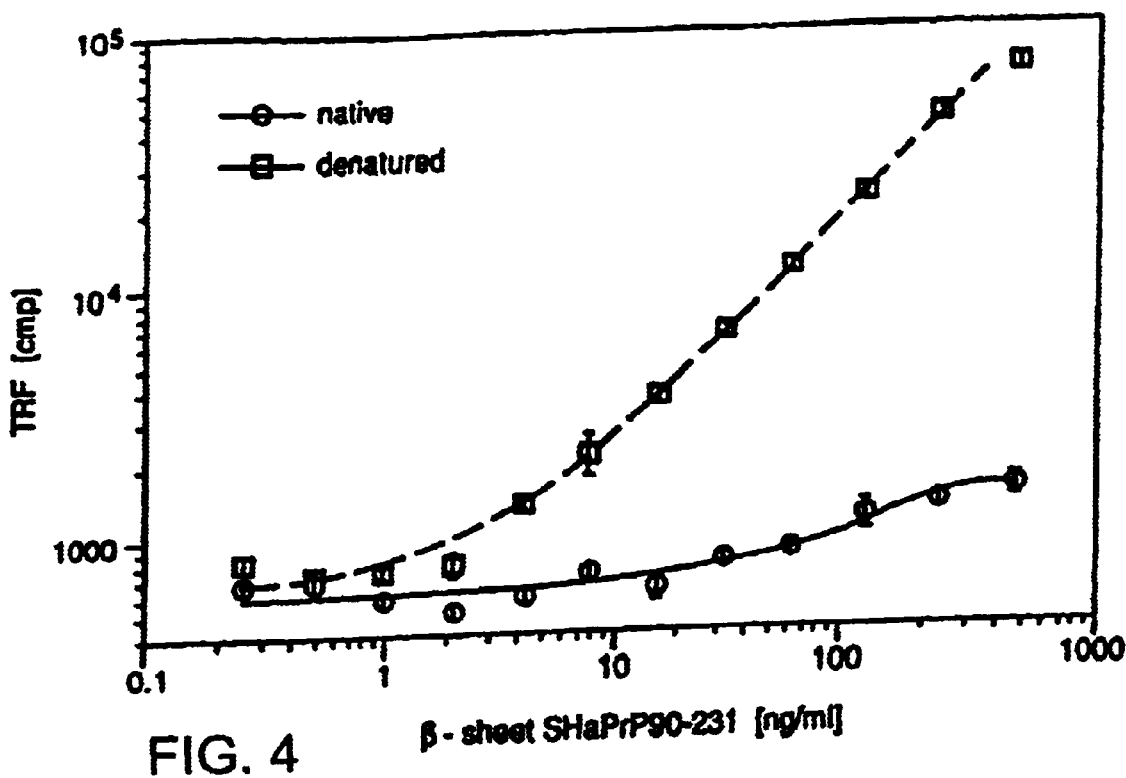
FIG. 4 is a graph showing the calibration of a direct assay with recombinant SHaPrP90–231 in β-sheet conformation, in the presence of 5% $PrP^{0/0}$ mouse brain homogenate wherein the data points and bars represent average±SEM obtained from four independent measurements.

More specifically, with some proteins there may be some differences due to the effect of the unfolding treatment on the proteins which are in the native non-diseased conformation—e.g., more epitopes of the protein in disease related conformation are exposed by treatment. This differential should be accounted for in drawing conclusions with respect to whether the original sample included proteins in the second, disease related conformation. Accounting for this effect is shown within FIGS. 3 and 4. In FIG. 3 there is shown a comparison of antibody binding to an untreated sample which contains only native protein in its non-disease configuration with the same native protein after unfolding treatment. As shown within FIG. 3 there is some difference between the results obtained with the treated protein showing a stronger signal in that the unfolding treatment increased the binding affinity of the protein. However, FIG. 4 shows the same results when the original sample included proteins which were in the second, disease related conformation. The native (PrP$^{Sc}$) disease related proteins which are not subjected to unfolding treatment provide a very weak signal. However, the unfolding treated PrP$^{Sc}$ proteins provide a very strong signal. The large differential between the unfolding treated and the untreated or native PrP$^{Sc}$ samples is a clear indication that the original sample included proteins with the second, disease related conformation in that these proteins do not bind to antibodies or bind to antibodies with a very low degree of binding affinity. However, after unfolding treatment these proteins bind to the antibodies as well or nearly as well or better than the proteins in the non-disease conformation which were treated via the unfolding treatment.

The assay can be used to test for the presence of the disease conformation of a given protein within any type of sample. Some of the most typical samples to be tested include pharmaceuticals which include components which are derived from living mammals or use materials derived from living mammals in their processing. It would also be desireable to test organs for transplantation and food items such as beef which was suspected of containing infectious prions. The invention could be used for testing for the presence of the disease conformation of one or more types of proteins such as infectious PrP$^{Sc}$ in pharmaceuticals, cosmetics, biopsy or autopsy tissue, brain, spinal cord, peripheral nerve, muscle, cerebrospinal fluid, blood and blood components, lymph nodes, and in animal or human-derived cultures infected or potentially infected by disease forms of proteins such as prions.

Treatment—Unfolding

An assay of the invention can use all or any of three basic types of treatment which are defined above. The treatments are (1) pretreatment, (2) unfolding treatment and (3) limited protease treatment. In general the conditions for pretreatment are gentle, those for unfolding treatment moderate and those for limited protease treatment are harsh. Each type of treatment can employ the same means (e.g. proteases, time, temperature, etc.) but employs each to a different degree, e.g. higher concentration, longer time, higher temperature.

The unfolding treatment denatures the protein but does not hydrolyze proteins of interest and can include exposing the proteins to any physical and/or chemical means which causes the protein which is originally present in a tightened, disease related conformation to assume a more relaxed conformation which has a higher degree of binding affinity for any binding partner such as antibodies. In general, the unfolding treatment involves subjecting the protein to some means which causes epitopes on the protein which were not previously exposed or partially exposed to become exposed or become more exposed so that an antibody or other binding partner can more readily bind to the newly exposed epitope.

Methods used for unfolding treatment may include: (1) physical, such as hydrostatic pressure or temperature, (2) chemical, such as acidic or alkaline pH, chaotropic salts, denaturing detergents, guanidine hydrochloride and proteinases such as Proteinase K and (3) combinations of above.

The treatment time will vary depending on the treatment used but should be carried out for sufficient time to obtain the desired effect, e.g. for unfolding treatment to expose new binding sites but not so long as to completely denature or hydrolyze the protein. When carrying out unfolding treatment on PrP proteins without chemical treatment the temperature is raised to about 40° C. to about 80° C. for a time sufficient to obtain the desired amount of unfolding of PrP$^{Sc}$. The temperature can be lower and the time shorter if the pH is raised to 12 or 13.

Pretreament

Before carrying out treatment or antibody testing of either portion of the sample it may be desirable to subject the sample to pretreatment. The pretreatment is carried out in order to destroy or remove unrelated proteins as well as some of the non-disease form of the protein present within the sample. Examples of pretreatment methodology include producing a column which includes antibodies bound to support surfaces which antibodies bind to the non-disease conformation of the protein thereby removing as much of the non-disease conformation of the proteins possible. Antibodies which bind unrelated but common proteins can also be used. Alternatively the sample can be subjected to physical treatment such as long term hydrostatic pressure or temperature alone or in combination with chemicals such as acids or alkalines as indicated above to destroy proteins present in the sample which proteins are not related to those being assayed for or are in the non-disease conformation. In some instances proteins in the non-disease and disease conformation will be destroyed. However, a higher relative percentage of the proteins in the non-disease conformation will be destroyed because these proteins are initially in a looser conformation which is more vulnerable to destruction. Thus, the pretreatment methodology results in a sample which includes a relatively lower concentration of the non-disease conformation of the protein relative to the concentration of the disease conformation of the protein. This increases the sensitivity of the assay making it possible to detect lower concentrations of the disease conformation of the protein. Removal of proteins is preferred over destruction of such in that destruction will decrease sensitivity if the disease conformation is destroyed. A particularly useful pretreatment method is disclosed in our patent application Ser. No. 09/026,967 entitled "Process for Concentrating Protein with Disease-Related Conformation".

Limited protease Treatment—Lytic Treatment

The limited protease treatment is a lytic treatment which is the harshest treatment method used in preparing samples for assays of the invention. After a portion of a sample has been subjected to the pretreatment treatment it is divided into two portions and one of the two portions is subjected to the unfolding treatment. If the basic assay shows that disease related protein is present in the sample then the total amount (or concentration) of disease related protein is determined. Another portion of the original sample or the isolated total disease related protein is then subjected to limited protease treatment. This treatment will destroy or hydrolyze all or substantially all protein in the sample but for disease related protein resistant to the limited protease treatment (e.g. PrP 27–30). The amount (or concentration) of this protease resistant protein is then determined and subtracted from the total amount of disease related protein to find the protease sensitive disease related protein (.e.g. protease—sensitive $PrP^{Sc}$). The limited protease treatment or lytic treatment can include (1) chemical methods such as being exposed to extremes in pH (e.g. 2 or less or 12 or above) strongly reducing or oxidizing compounds; and/or (2) enzymatic methods such as proteases (e.g. proteinase K). The concentration of the treating compounds as well as the time and temperature will vary with the protein being treated and end result to be obtained. When treating PrP proteins the treatment is carried out in order to (1) hydrolyze all or substantially all non-PrP proteins present in the sample; (2) hydrolyze all or substantially all non-$PrP^C$ present; (3) hydrolyze protease sensitive $PrP^{Sc}$ present; and (4) hydrolyze the 65 N-terminal amino acids of protease resistant $PrP^{Sc}$ present thereby leaving only PrP 27–30 un-hydrolyzed.

The limited protease treatment can, like the unfolding treatment or pretreatment, be carried out with temperature. For example, hydrolysis of PrP proteins can be obtained by heating to above 80° C. to 132° C. for 1 to 3 days. The time and temperature can be significantly reduced by raising the pH to 12 or 13. The object of this treatment is to do more than unfold proteins and to hydrolyze proteins.

Binding Proteins to Support Surfaces

The method of chemical or affinity coupling of PrP protein to the plastic support are generally described in available literature and may vary. The antibodies used in the diagnostic assay are polyclonal, monoclonal or recombinant Fab and need to be species specific with preferential binding to the native $PrP^C$ or denatured form of $PrP^{Sc}$ with preferably at least 4-fold lower reactivity with infectious $PrP^{Sc}$, assuming the same amount of the antigen.

Using the Assay to Detect Prions ($PrP^{Sc}$)

One aspect of the invention is a two step process to diagnose prion disease by quantitatively measuring the native infectious form of $PrP^{Sc}$ protein in sample material or in the brains of susceptible animals inoculated with such material. The sample is preferably pretreated to remove as much unrelated and non-disease protein as possible. The pretreated sample is divided into two aliquots. The first aliquot is crosslinked to the solid plastic support in native conformation through a chemical activation step under the non-denaturing conditions, i.e., no treating. The second portion of the sample is first subjected to unfolding treatment and then crosslinked to the plastic support. Both portions of the sample material react in situ with the labeled antibodies that preferentially recognize native $PrP^C$ or unfolding treated $PrP^{Sc}$ of the given animal species. The amount of the antibody bound to the unfolding treated or native conformations of PrP protein is recorded by the signal of the IgG label. The excess of the signal obtained with the portion of sample subjected to unfolding treatment over that expected from an increase in the signal obtained with the native α-helical conformation of $PrP^C$ (i.e., the increase over the adjusted amount)is the measure of the amount of infectious β-sheet structured $PrP^{Sc}$ in the original sample. The formula developed for calculation of $PrP^{Sc}$ content is shown in formulae provided here and exemplified in Example 11.

The diagnosis of the presence of prions is established by three procedures: (1) measurement of treated sample alone and by detecting the increase in the total PrP amount in the examined sample above the background levels of $PrP^C$ obtained from normal controls; (2) calculation of the ratio between denatured versus native signal for a given antibodies—for example values higher than 2.2 for Europium-labeled 3F4 IgG indicates presence of $PrP^{Sc}$ preferably using time-resolved, dissociation-enhanced fluorescence; (3) evaluation of the excess of the denatured sample signal over that expected from increase in the signal for α-helical conformation of $PrP^C$ as a measure of the amount of infectious β-sheet structured $PrP^{Sc}$ in the original sample. Preferably prior to step (1) the method uses a pre-treatment step whereby $PrP^C$ is removed or destroyed in relative amounts greater than that of $PrP^{Sc}$.

In a scrapie infected Syrian hamster brain, the concentration of $PrP^{Sc}$ is 5–10 times higher than $PrP^C$ when the animals become ill. At this time, the prion titer in their brains is $10^7$–$10^8$ $ID_{50}$ units/ml of 10% homogenate. The highly quantitative system that we have developed allows us to subtract the $PrP^C$ signal. The subtraction can be readily carried out when the concentration of $PrP^{Sc}$ is greater than $PrP^C$. However, the subtraction becomes difficult when the concentration of $PrP^{Sc}$ is much less than $PrP^C$.

To address the foregoing problem, the present assay utilizes the principle of affinity between different conformations of antigen and antibody. To measure the concentration of $PrP^{Sc}$ when it is much less than $PrP^C$, the detection system has to have extreme sensitivity and a linear range of at least $10^4$. The assay described herein can readily detect $PrP^{Sc}$ at a concentration of (approximately) 50 pg/ml using Europium-labeled IgG. Assuming $10^5$–$10^6$ $PrP^{Sc}$ molecules per $ID_{50}$ unit the present assay can readily detect $5 \times 10^2$–$5 \times 10^3$ $ID_{50}$ units per ml.

The assay can detect $PrP^{Sc}$ in mixtures (by direct method) where the concentration of $PrP^{Sc}$ is less than 1% of the concentration of $PrP^C$. Additional sensitivity can be achieved by immunoprecipitation, using a sandwich format for a solid state assay, differential centrifugation with detergent extraction to remove $PrP^C$, the indirect transgenic animal method or combinations of these methods. A conservative estimate is that such procedures should allow measurement of between 5 and 50 $ID_{50}$ units per ml or less conservatively to measure between 0.1 and 0.01 $ID_{50}$ units per ml. Such measurements would provide a rapid, "positive" means of establishing biological sterility which is the "absence" of infectivity.

Antibodies

Method of generating antibodies are generally known to those skilled in the art. In that the disease form is often in a tighter configuration than the non-disease form, with less epitopes exposed, one can readily generate antibodies which bind only to the non-disease form of the protein or the treated disease form. For example, antibodies detecting treated forms of $PrP^{Sc}$ protein and $PrP^C$ protein may be generated by immunizing rabbits or mice with α-helical conformations of recombinant PrP, native $PrP^C$ from animal brains, synthetic peptides in α-helical or random coil conformations, or against denatured $PrP^{Sc}$ or PrP 27–30. Only antibodies with affinity at least 4 fold higher for $PrP^C$ (or denatured conformation of $PrP^{Sc}$ of the same species) as compared to their affinity for $PrP^{Sc}$ should be selected. The method of antibody generation, purification, labeling and detection may vary.

The IgG or Fab's may be purified from different sources by affinity HPLC using protein A column and Size exclusion HPLC. The purified antibodies may be labeled with Europium and detected by time resolved fluorescence. The antibody binding to different conformations of PrP protein may be measured by time-resolved, dissociation-enhanced fluorescence. However, the system of detection of PrP-bound IgG on solid support in situ or in solution may vary. Further, it is possible to use direct or indirect immunological methods including direct radiolabels, fluorescence, luminescence, avidin-biotin amplification, or enzyme-linked assays with color or luminescent substrates.

An antibody which can be used in the invention is disclosed in U.S. Pat. No. 4,806,627, issued Feb. 21, 1989, disclosing monoclonal antibody 263K 3F4, produced by cell line ATCC HB9222 deposited on Oct. 8, 1986, which is incorporated herein by reference The cell line producing the antibody can be obtained from the American Type Culture Collection, 12301 Parklawn Drive, Rockville, Md. 20852.

In general, scrapie infection fails to produce an immune response, with host organisms being tolerant to $PrP^{Sc}$ from the same species. Antibodies which bind to either $PrP^c$ or $PrP^{Sc}$ are disclosed in WO97/10505, published Mar. 20, 1997. Any antibody binding to $PrP^c$ and not to $PrP^{Sc}$ can be used, and those skilled in the art can generate such using known procedures, e.g., see methods of producing page display antibody libraries in U.S. Pat. No. 5,223,409. Polyclonal anti-PrP antibodies have though been raised in rabbits following immunization with large amounts of formic acid or SDS-denatured SHaPrP 27–30 [Bendheim, Barry et al. (1984) Nature 310:418–421; Bode, Pocchiari et al. (1985) J Gen Virol 66:2471–2478; Safar, Ceroni et al. (1990) Neurology 40:513–517]. Similarly, a handful of anti-PrP monoclonal antibodies against PrP 27–30 have been produced in mice [Barry and Prusiner (1986) J Infect Dis 154:518–521; Kascsak, Rubenstein et al. (1987) J Virol 61:3688–3693]. These antibodies were generated against formic acid- or SDS-denatured PrP 27–30 and are able to recognize native $PrP^C$ and treated or denatured $PrP^{Sc}$ from both SHa and humans equally well, but do not bind to MoPrP. Not surprisingly, the epitopes of these antibodies were mapped to regions of the sequence containing amino acid differences between SHa- and MoPrP [Rogers, Yehiely et al. (1993) Proc Natl Acad Sci USA 90:3182–3186].

It is not entirely clear why many antibodies of the type described in the above cited publications will bind to $PrP^C$ and treated or denatured $PrP^{Sc}$ but not to native $PrP^{Sc}$. Without being bound to any particular theory it is suggested that such may take place because epitopes which are exposed when the protein is in the $PrP^C$ conformation are unexposed or partially hidden in the $PrP^{Sc}$ configuration—where the protein is relatively insoluble and more compactly folded together.

For purposes of the invention an indication that no binding occurs means that the equilibrium or affinity constant $K_a$ is $10^6$ l/mole or less. Further, binding will be recognized as existing when the $K_a$ is at $10^7$ l/mole or greater, preferably $10^8$ l/mole or greater. The binding affinity of $10^7$ l/mole or more may be due to (1) a single monoclonal antibody (i.e., large numbers of one kind of antibodies) or (2) a plurality of different monoclonal antibodies (e.g., large numbers of each of five different monoclonal antibodies) or (3) large numbers of polyclonal antibodies. It is also possible to use combinations of (1)–(3). Selected preferred antibodies will bind at least 4-fold more avidly to the treated or denatured $PrP^{Sc}$ forms of the protein when compared with their binding to the native conformation of $PrP^{Sc}$. The four fold differential in binding affinity may be accomplished by using several different antibodies as per (1)–(3) above and as such some of the antibodies in a mixture could have less than a four fold difference.

A variety of different types of assays of the invention may be used with one or more different antibodies. Those skill in the art will recognize that antibodies may be labeled with known labels and used with currently available robotics, sandwich assays, electronic detectors, flow cytometry, and the like.

Quantitative Calculations

Using the methodology described above it is possible to calculate the difference between the amount of signal obtained from a sample which has not been treated and the signal obtained with a sample which has been treated. This difference represents (after adjusting for the effect of treatment on the non-disease conformation) the amount (concentration) of protein in disease conformation present in the original sample. After obtaining the difference the formula put forth below can be used to calculate the amount of protein in the disease conformation present in the original sample per unit of volume.

$$F_n = F_{n\alpha} + F_{n\beta} \rightarrow F_{n\alpha} = F_n - F_{n\beta}, F_{n\beta} \sim \text{background} \quad \text{a)}$$

$$F_d = F_{d\alpha} + F_{d\beta} \quad \text{b)}$$

$$\Delta F_{n \rightarrow d} = \Delta F_{\alpha n \rightarrow d} + \Delta F_{\beta n \rightarrow d}$$

$$\Delta F_{\beta n \rightarrow d} = F_d - F_n - \Delta F_{\alpha n \rightarrow d}$$

$$[PrP_\beta] \text{ or } [DRC] \sim \Delta F_{\beta n \rightarrow d} = F_d - (F_n * f_{\alpha n \rightarrow d})$$

The definition of each of the above variables is provided below.

F—fluorescence signal (note that any detectable signal could be used);

$F_n$—fluorescence signal of native conformation;

$F_{n\alpha}$ and $F_{n\beta}$ fluorescence signals of native α-helical and β-sheet conformations, respectively;

$F_d$—fluorescence signal of PrP in the treated or denatured state;

$F_{d\alpha}$ and $F_{d\beta}$—are the signals of denatured α-helical of β-sheet states of PrP;

$\Delta F_{n \rightarrow d}$—increase of the fluorescence signal in the transition from native to denatured state;

$\Delta F_{\alpha n \rightarrow d}$—increase in the fluorescence signal of α-helical conformation in the transition from native to denatured state;

$\Delta F_{\beta n \rightarrow d}$—increase in the signal of β-sheet conformation in the transition from native to denatured state;

$f_{\alpha n \rightarrow d}$—correlation factor for the transition from native to denatured state of α-helical PrP;

$[PrP_\beta]$—concentration of prion protein in β-sheet conformation.

[DRC]—concentration of any protein in disease related conformation.

∼—proportional to.

*—multiple.

The formula provided above is used to specifically calculate the concentration of prion protein in the β-sheet conformation. However, the same formulae can be used to calculate the concentration of any protein i.e., the concentration of any constricted, disease conformation of a protein such a $[\beta A4_\beta]$. More generally, [DRC] represents the concentration of the disease related conformation of a protein.

To provide a specific example, the above definitions have been provided specifically with respect to PrP proteins which proteins include at least one relaxed, non-disease conformation (PrP$^C$) which includes an α-helical conformation and at least one constricted, disease related conformation (PrP$^{Sc}$) which includes a β-sheet conformation. The formulae are used to calculate the concentration of the disease related conformation of the protein present in the sample. Per the specific formulae and definitions provided above the formulae are used to calculate the concentration of prion proteins which include the β-sheet configuration (see Example 11).

The signal used in calculating the above formula is a fluorescence signal. However, any detectable signal can be used. The total signal is represented by $F_n$ which is a combination of the signal received from the disease and the non-disease related conformations. This is a signal which would be calculated from portion No. 1 which is not treated per the assay described above. The variable $F_d$ is the signal which is obtained by treating portion No. 2 of the sample. This signal is a combination of the signal received from treated protein in the non-disease conformation plus treated protein in the disease conformation.

It has been recognized that there is a difference in signal obtained by treating a sample (e.g. via unfolding treatment) which includes no disease related conformation of the protein. The difference should be accounted for to obtain an accurate reading. The difference in signal obtained between the native sample and the treated sample is, of course, a combination of the difference in signal obtained by treating the disease related conformation and the non-disease conformation. The increase in the signal obtained by subjecting the disease conformation to unfolding treatment, i.e., the difference between the signal of the untreated disease conformation and the signal received from the treated disease conformation can be calculated by subtracting the signal received from treating the entire sample from the signal received from calculating the increase in signal obtained from the untreated non-disease conformation and the treated non-disease conformation. Using these equations it is possible to produce the final equation which provides the concentration of protein in the disease conformation present in the original sample (see Example 11).

Differentiating (Typing) of Protein Strains

Different animals, including humans may become infected with different strains of pathogenic proteins. A "mutation table" is provided here to list some of the different mutations associated with different strains of prion infections. At times it may be important which specific strain has infected an individual in that such information may be useful in (1) providing a more precise diagnosis, (2) administering the appropriate treatment or (3) determining the source of the infection by matching the strain to a strain in a probable source of infection.

The particular strain of pathogenic protein causing an infection can be determined from two pieces of information which can be calculated using the present invention. Example 11 shows how the present invention can be used to determine the absolute amount, i e., the concentration of prions in a sample of given size. Example 8 shows how to calculate the "prion index" which is the ratio of antibody binding to denatured:native PrP protein. A "protein index" for other proteins is the ratio of binding of any binding partner to the denature:native form of the protein. In general terms, the "prion index" is simply a numerical characterization of the affect the treatment has on the protein.

To determine the particular strain one must first calculate a standard for each strain. This is done by determining the effect (prion index) of a particular treatment on a known amount of a known strain. This can be plotted as shown in FIG. 24. Once the standard is calculated, the strain of other samples can be readily determined—standards are preferably calculated at a number of different concentrations for each strain. To determine the strain of a simple sample, one calculates the concentration of protein in the sample and the affect of treatment on that concentration. The results are matched to the standard (as in FIG. 24) to determine the strain. Example 18 is a specific example of such as taken in combination with FIG. 24 The same concentration of the same strain will be effected in the same way by a given treatment. However, the same concentration of different strains will be effected differently by the same treatment making it possible to determine the strain.

Diseases Associated with Insoluble Proteins

Much of the disclosure and the specific examples provided herein relate to the use of the assay in connection with determining the presence of PrP$^{Sc}$ in the sample. However, as indicated above, the assay of the invention can be applied to determining the presence of any protein which assumes two different conformational shapes, one of which is associated with the disease. The following is a non-limiting list of diseases with associated insoluble proteins which assume two or more different conformations.

| Disease | Insoluble Proteins |
| --- | --- |
| Alzheimer's Disease | APP, Aβ peptide, α1-antichymotrypsin, tan, non-Aβ component |
| Prion diseases, Creutzfeld Jakob disease, scrapie and bovine spongeform encephalopathy | PrP$^{Sc}$ |
| ALS | SOD and neurofilament |
| Pick's disease | Pick body |
| Parkinson's disease | Lewy body |
| Diabetes Type 1 | Amylin |
| Multiple myeloma--plasma cell dyscrasias | IgGL-chain |
| Familial amyloidotic polyneuropathy | Transthyretin |
| Medullary carcinoma of thyroid | Procalcitonin |
| Chronic renal failure | β$_2$--microglobulin |
| Congestive heart failure | Atrial natriuretic factor |
| Senile cardiac and systemic amyloidosis | Transthyretin |
| Chronic inflammation | Serum amyloid A |
| Atherosclerosis | ApoA1 |
| Familial amyloidosis | Gelsolin |

It should be noted that the insoluble proteins listed above each include a number of variants or mutations which result in different strains which are all encompassed by the present invention. Known pathogenic mutations and polymorphisms in the PrP gene related to prion diseases are given below and the sequences of human, sheep and bovine are given in U.S. Pat. No. 5,565,186, issued Oct. 15, 1996.

| | MUTATION TABLE | | |
| --- | --- | --- | --- |
| Pathogenic human mutations | Human Polymorphisms | Sheep Polymorphisms | Bovine Poly-morphisms |
| 2 octarepeat insert | Codon 129 Met/Val | Codon 171 Arg/Glu | 5 or 6 octarepeats |
| 4 octarepeat insert | Codon 219 Glu/Lys | Codon 136 Ala/Val | |

MUTATION TABLE -continued

| Pathogenic human mutations | Human Polymorphisms | Sheep Polymorphisms | Bovine Poly- morphisms |
|---|---|---|---|
| 5 octarepeat insert | | | |
| 6 octarepeat insert | | | |
| 7 octarepeat insert | | | |
| 8 octarepeat insert | | | |
| 9 octarepeat insert | | | |
| Codon 102 Pro-Leu | | | |
| Codon 105 Pro-Leu | | | |
| Codon 117 Ala-Val | | | |
| Codon 145 Stop | | | |
| Codon 178 Asp-Asn | | | |
| Codon 180 Val-Ile | | | |
| Codon 198 Phe-Ser | | | |
| Codon 200 Glu-Lys | | | |
| Codon 210 Val-Ile | | | |
| Codon 217 Asn-Arg | | | |
| Codon 232 Met-Ala | | | |

It should also be noted that such proteins have two different 3-dimensional conformations with the same amino acid sequence. One conformation is associated with disease characteristics and is generally insoluble whereas the other conformation is not associated with disease characteristics and is soluble. The methodology of the present invention is not limited to the diseases, proteins and strains listed.

Detecting the β-Sheet Form of βA4

One aspect of the invention involves a two step process to diagnose Alzheimer's disease based on the presence of a constricted form of a protein (βA4 amyloidosis) by quantitatively measuring β-sheet form of βA4 protein in sample material, e.g., in the brain or body fluids. The sample is divided into two aliquots. The first aliquot is crosslinked to a solid plastic (long chain polymeric material) support in native conformation through a chemical activation step under the nondenaturing conditions. The second portion of the sample is first subjected to unfolding treatment and then crosslinked to the plastic support. Both portions of the sample material react in situ with the labeled antibodies that preferentially recognize soluble βA4 or unfolding treatment βA4 of the human or a given animal species. The amount of the antibody bound to unfolded or native conformations of βA4 protein is recorded by the signal of the labeled secondary antibody. The excess of the signal obtained with the unfolding treated sample compared to that expected change in the signal obtained with the native α-helical conformation of βA4 protein is the measure of the amount of β-sheet structured βA4 in the original sample. The formula developed for calculation of βA4 content is provided above in connection with the calculation of $PrP^{Sc}$ content.

The diagnosis of βA4 amyloidosis (Alzheimer's disease) is established by three procedures. (1) measurement of denatured sample alone and by detecting the increase in the total βA4 amount (concentration) in the examined sample above the background levels of soluble βA4 obtained from normal controls; (2) calculation of the ratio between unfolding treated versus native signal for a given antibodies (protein index)—for example values higher than 2 for monoclonal antibody 6F3D and europium labeled secondary antibody; (3) evaluation of the change of the denatured sample signal over that expected change in the signal for α-helical conformation of βA4 as a measure of the amount of infectious β-sheet structured βA4 in the original sample. The formula developed for calculation of βA4 content is provided above. The particular strain of βA4 can also be determined using the same methodology described above to determine the strain of $PrP^{Sc}$ in a sample.

The invention provides a direct diagnostic method for detecting the presence pathogenic forms of βA4 protein in pharmaceuticals, biopsy or autopsy tissue, brain, spinal cord, peripheral nerves, muscle, cerebrospinal fluid, blood and blood components, lymph nodes, and in animal- or human-derived cultures expressing or potentially expressing βA4 protein. The invention also makes it possible to follow the α-helix-to-β-sheet conformational transition of βA4 protein, or its fragments of synthetic or recombinant origin, and to provide a method to screen compounds for their ability to stabilize the normal soluble conformation of βA4 protein and thus prevent conversion into pathogenic insoluble and β-sheet-structured βA4 protein.

Typical methods of sample denaturation include: (1) physical, such as hydrostatic pressure or temperature, (2) chemical, such as acidic or alkaline pH, chaotropic salts, or denaturing detergents, and (3) combination of above. Methods of chemical or affinity coupling of βA4 protein to a plastic support are described in available literature and may vary. Antibodies used in the diagnostic assay may be polyclonal, monoclonal or recombinant Fab and must be species specific with preferential binding to the soluble or denatured form of βA4 with preferably at least a 2-fold difference in reactivity between α-helical and β-sheet structured βA4, assuming the same amount of antigen.

Methods of sample attachment to the plastic support may vary and may be covalent or non-covalent as described in available literature. The sensitivity of the assay described in the examples may be increased by using high-affinity antibodies, sandwich formate, immunoprecipitation, or differential centrifugation. However, only the antibodies with an affinity at least a 2 fold for unfolding treated as compared to the native β-sheet conformation of βA4 of the same species shall be used for the diagnostic assay. Methods of antibody generation, purification, labeling and detection may vary. The antibody binding to different conformations of βA4 protein was measured by time-resolved, dissociation-enhanced fluorescence. However, the system of detection of βA4-bound IgG on solid support in situ or in solution may vary and may use direct or indirect immunological methods including direct radiolabels, fluorescence, luminescence, avidin-biotin amplification, or enzyme-linked assays with color or luminescent substrates.

EXAMPLES

The following examples are put forth so as to provide those of ordinary skill in the art with a complete disclosure and description of how to make and use assays of the present invention, and are not intended to limit the scope of what the inventors regard as their invention, nor are they intended to represent or imply that the experiments below are all of or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Example 1

Expression of Recombinant Prion Proteins

For the development and calibration of the diagnostic assays, recombinant Syrian hamster prion proteins of sequence 90–231 were refolded into α-helical or β-sheet conformations as described [Mehlhorn, Groth et al. (1996) *Biochemistry* 35:5528–5537]. PCR (Perkin-Elmer) was used to amplify the DNA corresponding to different portions of the Syrian hamster prion protein in order to ligate it into *E. coli* secretion vectors. Several 5' oligonucleotide primers were synthesized with an Mlu I restriction site within the C-terminal coding sequence of the STII signal peptide [Lee, Moseley et al. (1983) *Infect Immun* 42:264–268; Picken, Mazaitis et al. (1983) *Infect Immun* 42:269–275] and the initial amino acids of the appropriate PrP sequence. One 3' oligonucleotide primer matching the 3' end of PrP, a stop codon and a Bam HI restriction site was used with each of the 5' oligonucleotides. The PCR amplified products were purified, ligated into the vectors previously digested with MluI/Bam HI and transformed into DH5a. Clones containing the PrP insert were sequenced and transformed into the protease deficient expression strain 27C7 (ATCC# 55244).

Large scale expression was carried out as described previously for other proteins using a different medium [Carter, Kelley et al. (1992) *Biotechnology* 10: 163–167], 500 mL of an overnight culture grown in LB medium supplemented with ampicillin was inoculated into 7 L of fermentation medium in an aerated 10 L fermentor (Braun, model E10). Cells were grown at 37° C. at a high agitation rate, and expression was induced by phosphate starvation. After 4 h, a 50% glucose solution was added at a rate of 1 mL/min; glucose levels were monitored using a glucose dipstick (Diastix, Miles Inc.). A pH of 7.4 was maintained throughout the run by the automated addition of 10% $H_2SO_4$ or 24% $NH_4OH$. The final volume was 10 L in which an $OD_{600}$ of ≧100 was achieved after 36 h. The *E. coli* was harvested by centrifugation at 10,000×g for 30 min and the resulting paste was stored at −20° C.

For purification, 100 g of *E. coli* paste was resuspended in 1 L of 25 mM Tris.HCl, pH 8.0, 5 mM EDTA (buffer A). This was centrifuged at 10,000×g for 20 min, and the supernatant containing soluble periplasmic proteins was discarded. The pellet was resuspended in 1 L of buffer A, passed through a cell disrupter twice (Microfluidics International, model MF 110), and centrifuged at 30,000×g for 1 h, after which the supernatant was discarded and the pellet was washed once in buffer A and centrifuged again at 30,000×g for 1 h. At this stage the pellet could be stored at −20° C. prior to further separation. It was subsequently solubilized in 8M GdnHCl/25 mM Tris-HCl, pH 8.0/100 mM DTT (buffer B) and centrifuged at 14,000×g for 20 min to remove the remaining insoluble matter. Aliquots of 6 mL of the supernatant containing ~200 mg total protein were separated by size exclusion chromatography (SEC) using a 26 mm×60 cm HiLoad Superdex 200 column (Pharmacia), eluting with 6M GdnHCl/12.5 mM Tris-HCl, pH 8.0/5 mM DTT/1 mM EDTA (buffer C) at a flow rate of 2 mL/min. Fractions enriched for the recombinant prion protein as identified by SDS-PAGE were pooled and further purified by reversed phase high performance liquid chromatography (RP-HPLC) employing a 25 mm×25 cm C-4 column (Vydac), Buffer 1: $H_2O$/0.1% TFA, Buffer 2 acetonitrile/0.09% TFA, flow rate 5 mL/min. The recombinant protein rPrP was found in fractions containing 40% acetonitrile. If the SEC eluate was stored at 4° C. for several days prior to RP-HPLC, the recombinant protein was eluted in earlier fractions containing only 35% acetonitrile.

Samples of the reduced protein and the refolded oxidized form were concentrated using a Centricon column (Amicon) with a molecular weight cut-off of 10,000 Da. The buffer for the reduced protein was 10 mM MES, pH 6.5 whereas the oxidized form was concentrated in the refolding buffer described above. The conformations of refolded oxidized and reduced forms of SHaPrP90–231 protein were determined by circular dichroism (CD) spectroscopy (FIG. 1).

Example 2

Purification of Hamster $PrP^C$ From Normal and $PrP^{Sc}$ From Scrapie Infected Hamster Brains Both proteins produced per Example 1 were used as a standards for the prion assay and to establish the sensitivity and linearity range of the diagnostic method. The purified Syrian hamster brain $PrP^C$ was used for the calibration of prion protein detection and correlated with results obtained on recombinant SHaPrP90–231 in α-helical, β-sheet, and denatured conformations. The $PrP^C$ protein was purified as described with some minor modifications [Pan, Stahl et al. (1992) *Protein Sci* 1:1343–1352; Pan, Baldwin et al. (1993) *Proc Natl Acad Sci USA* 90:10962–10966]. Protein content was determined by amino acid analysis. The purity of $PrP^C$ protein, as demonstrated on SDS PAGE followed by silver staining and Western, was ≧95%.

Standard Syrian hamster $PrP^{Sc}$ was purified from a standard pool of scrapie strain Sc237 infected hamster brains as described with only minor modifications [Turk, Teplow et al. (1988) *Eur J Biochem* 176:21–30]. The infectivity of this standard, as determined by an incubation time assay on Syrian hamsters after intracerebral inoculation, was $10^{7.3}$ $ID_{50}$/ml and specific infectivity $10^{8.2}$ $ID_{50}$/mg of $PrP^{Sc}$ protein. However, the specific infectivity may vary from lot to lot ±$10^{0.5}$ $ID_{50}$/mg. The protein content was determined by BCA assay using Bovine serum albumin as a standard. The preparation was considered homogeneous with one major band on SDS PAGE after silver staining and Western Blots.

Example 3

Selection, Labeling and Detection Method of Antibodies Used in the Assay

The protocols and methods of antibody production and characterization are in general described elsewhere [Harlow and Lane (1988) supra: 726]. The data described in this and following examples were generated with immunoaffinity purified polyclonal antibody N12 and P3 [Safar, Ceroni et al. (1990) *Neurology* 40:513–517; Rogers, Serban et al. (1991) *J Immunol* 147:3568–3574], made against synthetic peptides corresponding sequence 90–145 (N12) and 222–231 (P3) of Syrian Hamster PrP [Barry, Vincent et al. (1988) *J Immunol* 140:1188–1193]; JS2 against denatured Syrian Hamster PrP 27–30 [Safar, Ceroni et al. (1990) *Neurology* 40:513–517]. The development and characteristics of monoclonal antibody 3F4 used in the assay are described elsewhere [Kascsak, Rubenstein et al. (1987) *J Virol* 61:3688–3693] and are described in U.S. Pat. No. 4,806,627, all of which are incorporated by reference to disclose and describe antibodies which can be used with the invention and methods of making those and related antibodies. The recombinant Fab recognizing denatured forms of prion protein were developed most recently [Williamson, Peretz et al. (1996) *Proc Natl Acad Sci USA* 93:7279–7282].

SHaPrP90–231 in α-helical, β-sheet and random coil conformations were covalently attached to glutaraldehyde activated polystyrene plates and incubated with serially diluted primary antibody. The amount of IgG reacting with each conformation of SHaPrP90–231 was determined either directly with Eu-labeled 3F4 IgG, or indirectly with europium labeled anti-rabbit or anti mouse antibody, according to usual protocols and the total signal was measured by time-resolved, dissociation-enhanced fluorescence. For the assay development were selected antibodies with the signal ratio of denatured versus β-sheet conformation of SHaPrP90–231 equal or higher than 4.

Example 4

Competitive and Direct Assay Format

Purified recombinant SHaPrP90–231, refolded into α-helical or β-sheet conformation, was diluted into 5% (w/v) brain homogenate obtained from $PrP^{0/0}$ mouse and containing no prion protein. The brain homogenate was made by three 30 sec bursts in PowerGen homogenizer equipped with plastic disposable probe in TBS, pH 7.4 containing protease inhibitors cocktail (1 mM PMSF, 2 μg/ml of Aprotinin, and 2 μg/ml of Leupeptin) and spun at 5° C. for 5 min at 500 G in a desktop centrifuge. The resulting supernatant was diluted 1:1 in TBS with final 4% (w/v) Sarcosyl and homogenized again by three 30 sec bursts in a PowerGen homogenizer. Next, the homogenate was spiked with different dilutions of recombinant SHaPrP90–231 in α-helical or β-sheet conformations (pretreatment).

Figure 1:
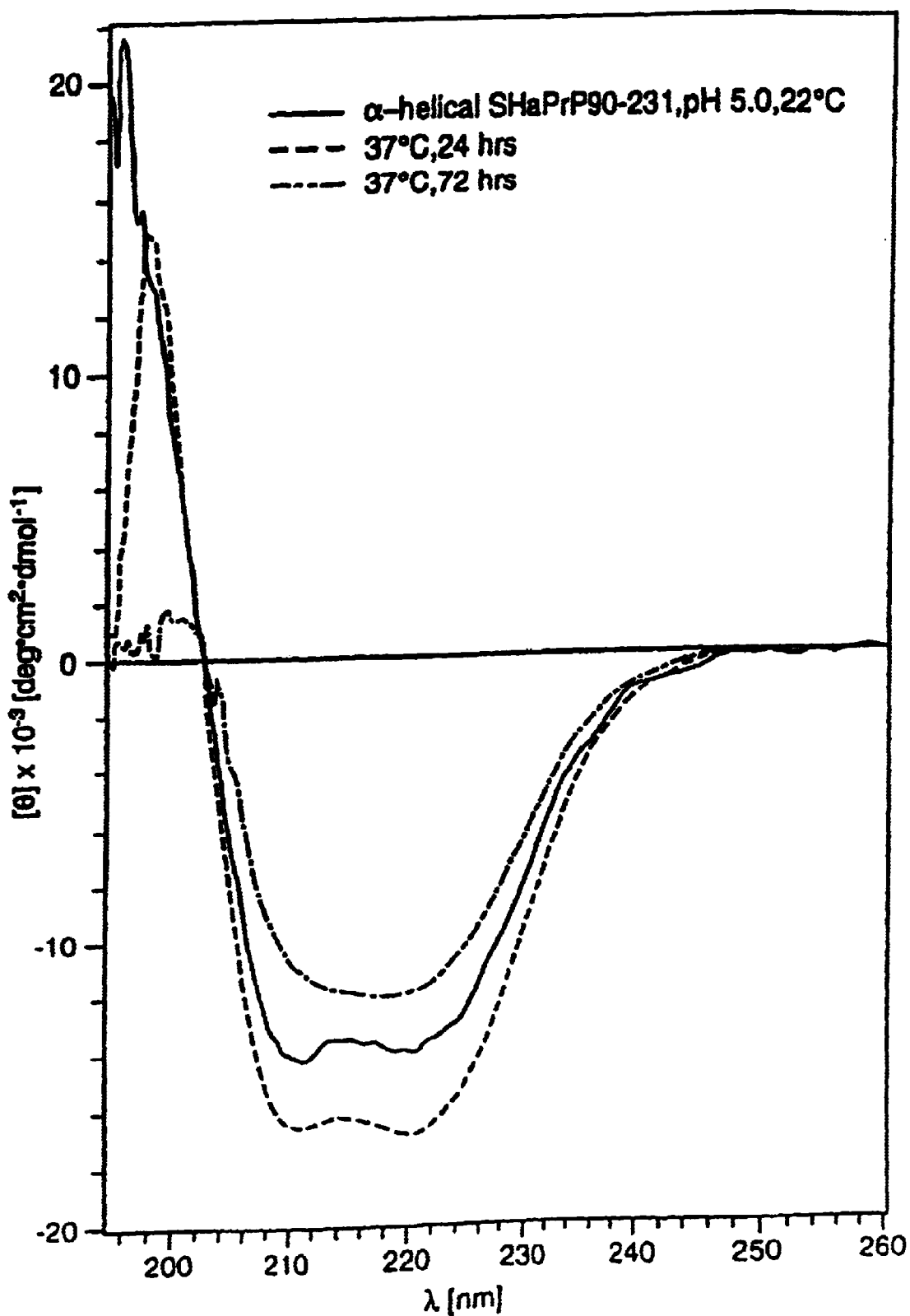
FIG. 1 is a spectrograph of the conformation of recombinant SHaPrP90–231 as determined by circular dichroism (CD) spectroscopy showing the two major bands with minima at 208 and 222 nm indicate α-helical conformation; single negative band with minimum at 217 nm is characteristic of predominantly β-sheet conformation. The figure shows the conversion of recombinant SHaPrP90–231 from α-helical to β-sheet conformation during incubation at 37° C. for 72 hrs, as determined by circular dichroism (CD) spectroscopy. The protein concentration was 5 mg/ml.
Figure 2:
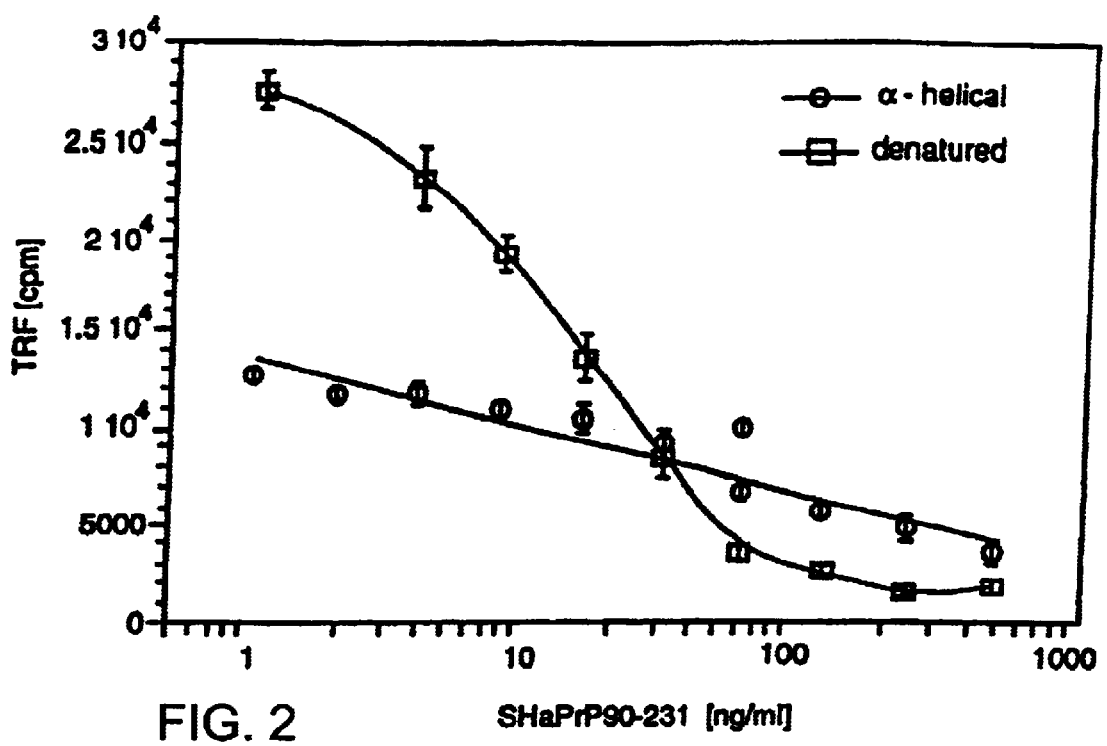
FIG. 2 is a graph showing the results of competitive assay of recombinant SHaPrP90–231 in α-helical and denatured conformations in the presence of 5% $PrP^{0/0}$ mouse brain homogenate wherein the difference in slope and crossover points obtained with Europium-labeled 3F4 IgG indicate that each conformations has both a different affinity and number of binding sites and further wherein the data points and bars represent average±SEM obtained from four independent measurements.

In a typical competitive assay, the analyte PrP in different conformations is preincubated with europium labeled 3F4 IgG and then transferred to the polystyrene plate coated with recombinant ShaPrP90–231 in SDS-denatured state. The results for analyte SHaPrP90–231 in α-helical and denatured state (FIG. 2) indicate marked difference in both available binding sites and affinity of europium-labeled 3F4 IgG with different conformations of prion protein.

In direct assay, each sample of dilution curve was divided into two aliquots: (1) untreated and designated native; (2) mixed with final 4M GdnHCl and heated for 5 min at 100° C. and designated denatured (unfolding treatment). Both samples were diluted 20-fold by $H_2O$ and aliquots loaded on polystyrene plate activated with glutaraldehyde. The plates, incubated overnight at 5° C., were blocked with TBS, pH 7.8, containing 0.5% BSA (w/v) and 6% Sorbitol (w/v). In the next step, they were washed three time with TBS, pH 7.8 containing 0.05% (v/v) of Tween(® 20 and incubated with europium-labeled antibodies listed above. The plates were developed after an additional 7 washing steps in enhancement solution provided by the europium label supplier (Wallac Inc., Turku, Finland) and signal counted on DELFIA 1234 Fluorometer (Wallac Inc., Turku, Finland).

Example 5

Differential Test for Various Conformations of SHaPrP90–231

The parameters obtained from direct assay with Eu-labeled 3F4 IgG were plotted as a function of the concentration. The results obtained with SHaPrP90–231 in α-helical conformation (FIG. 3) indicate relatively small difference between signal of α-helical and denatured protein. The sensitivity limit for denatured PrP in the presence of 5% brain homogenate is ≦1 ng/ml and linearity range over 3 orders of magnitude. In the experiments with the β-sheet form of SHaPrP90–231 (FIG. 4), Eu-labeled 3F4 IgG bind strongly to a denatured form of the protein. In contrast, the reactivity with the native β-sheet form of the protein only marginally exceeded the background even at high protein concentrations. When the results are expressed as a ratio of the fluorescence of denatured versus native states of the prion protein (FIGS. 3 and 4), the ratio for α-helical conformation is 1–1.8 and for recombinant SHaPrP90–231 in β-sheet conformation is 5–50.

Figure 6:
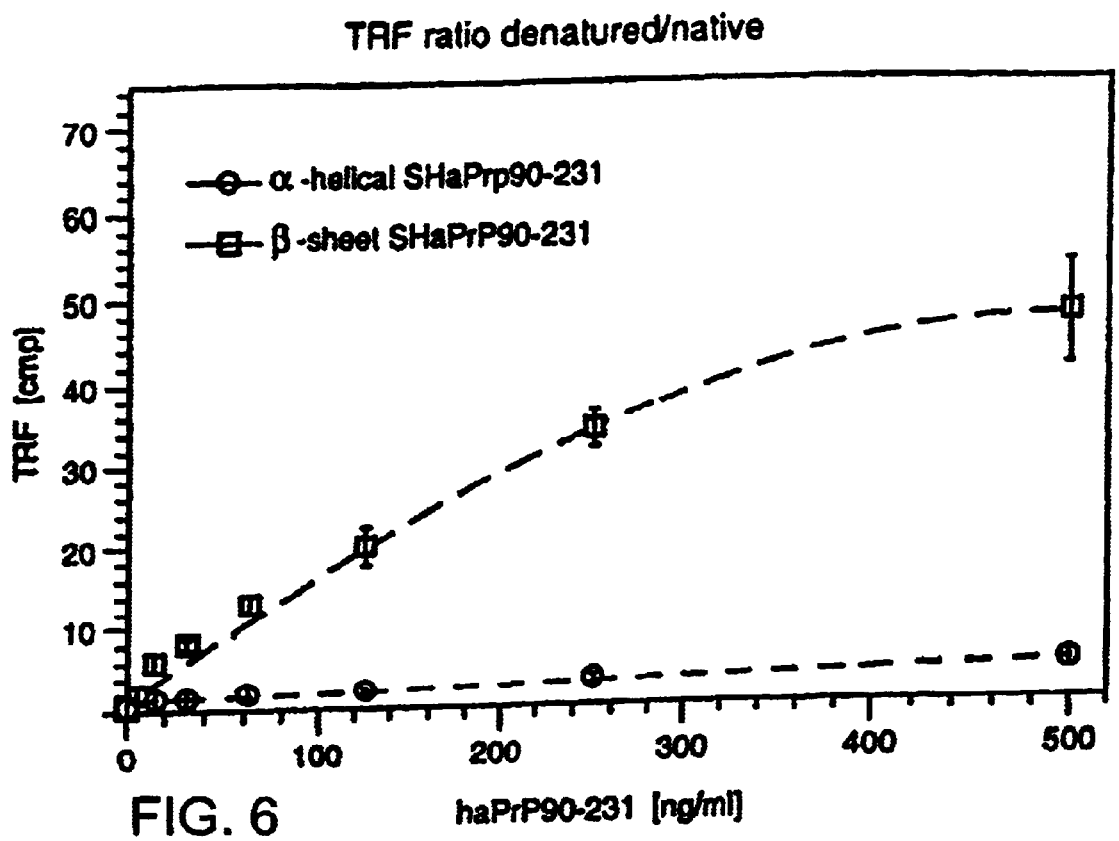
FIG. 6 is a graph showing the ratio between the signals of treated (unfolded shown as denatured) and native SHaPrP90–231 in α-helical and β-sheet conformations, developed with Eu-labeled 3F4 IgG wherein the data points and bars represent average±SEM obtained from four independent measurements. Two major bands in the CD spectrum with minima at 208 and 222 nm indicate an α-helical conformation; a single negative band with minimum at 217 nm is characteristic of predominantly β-sheet conformation; a negative trough toward 197 nm documents random-coil conformation. The calibration of the conformation-dependent immunoassay was performed in the presence of 5% (w/v) $Prnp^{0/0}$ mouse brain homogenate. The data points and bars represent average±SEM obtained from four independent measurements.

This effect was further utilized to analyze PrP samples of unknown conformation where the small increase in signal of Eu-labeled 3F4 IgG after denaturation of PrP is a characteristic of α-helical conformation. By contrast, the large increase in the signal above the expected change for α-helical conformation is diagnostic of the PrP90–231 in β-sheet conformation (FIGS. 3 and 4). The results are expressed in two different forms: (1) as a ratio (FIG. 6), where index ≦1.8 for recombinant SHaPrP90–231 indicates that the protein was originally in all α-helix conformation and index >1.8 indicates presence of β-sheet conformation; (2) as a formula shown herein and exemplified in Example 11, where the excess increase of signal above that expected for α-helical conformation is proportionate to the amount of SHaPrP90–231 in β-sheet conformation.

Example 6

Quantitative Assay for Recombinant SHaPrP90–231 and $PrP^C$

Figure 5:
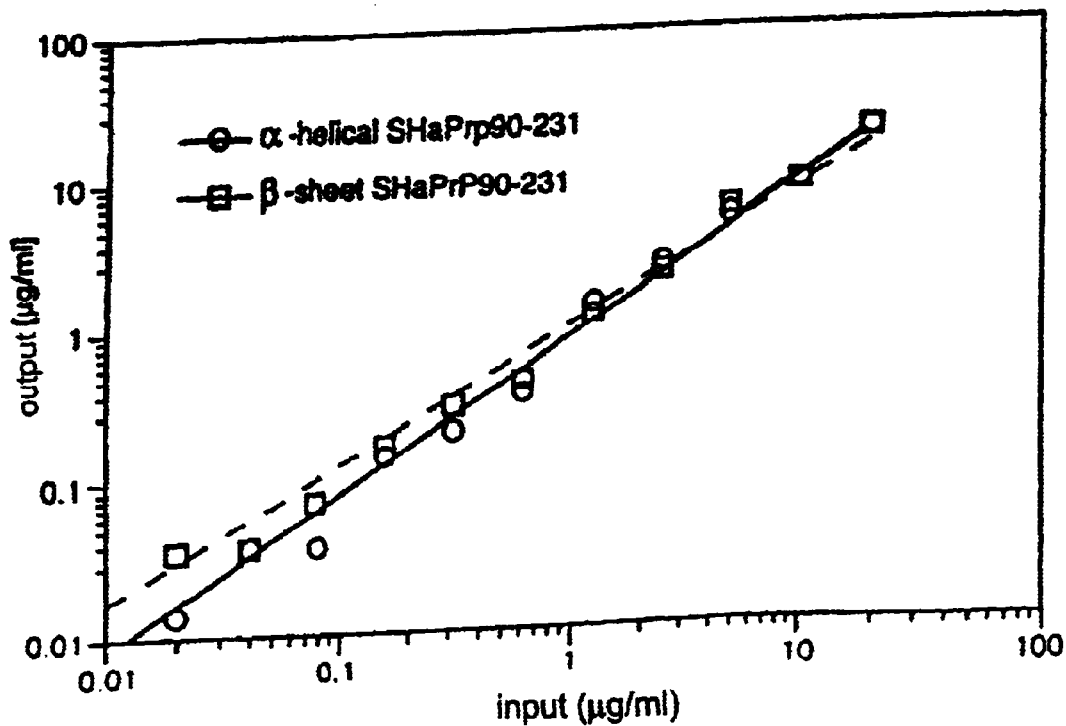
FIG. 5 is a graph showing the input-output validation of a direct assay for both α-helical and β-sheet forms of SHaPrP90–231 in the presence of 5% $PrP^{0/0}$ mouse brain homogenate wherein the amount of the protein on the x axis was determined by amino acid analysis and the amount of the protein on the y axis is calculated from the assay.

The input/output calibration for denatured ShaPrP90–231 in both α-helical and β-sheet conformations was linear within three orders of magnitude, and provide a high degree of confidence (FIG. 5) for the assay. Also assayed was $PrP^C$, serially diluted into $PrP^{0/0}$ mouse homogenate which provided results with high degree of confidence within linearity range of 3 orders of magnitude. Next, the assay was calibrated by purified infectious $PrP^{Sc}$ in the presence of 5% $PrP^{0/0}$ brain homogenate. The calibration with $PrP^{Sc}$ provided a linear response within similar range.

Figure 7:
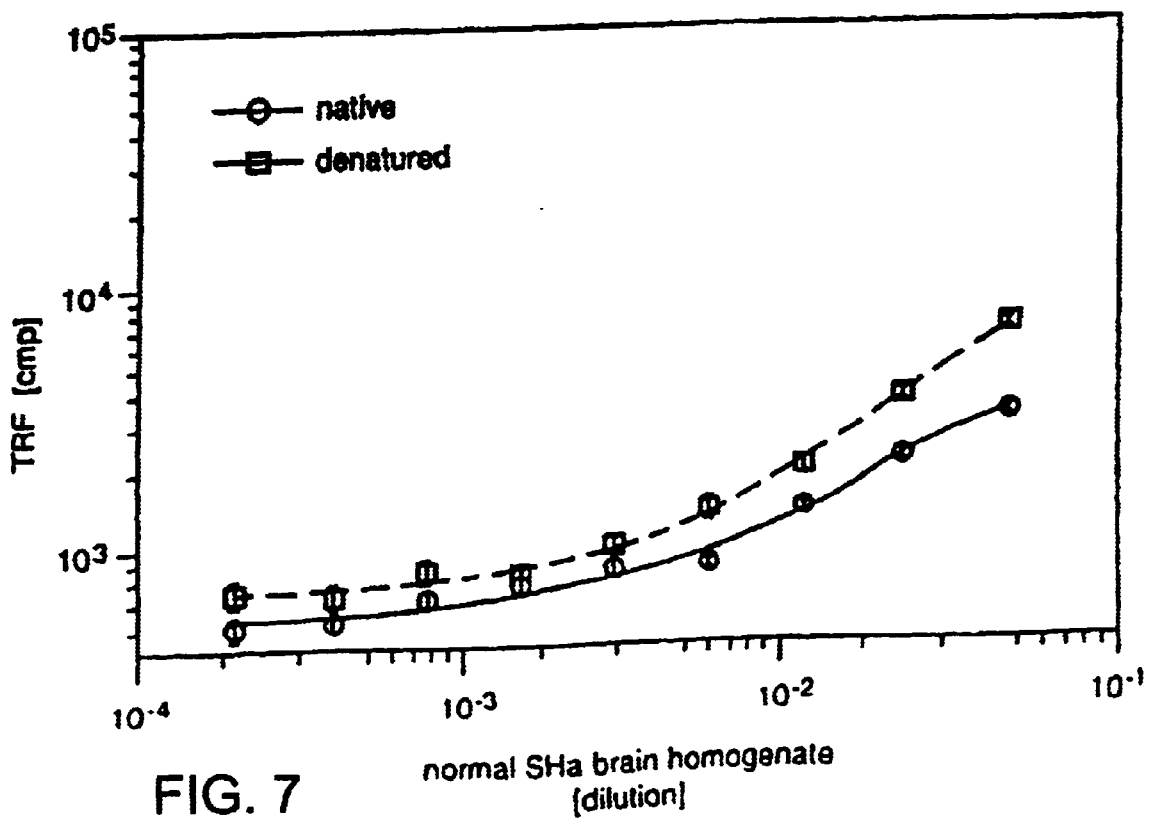
FIG. 7 is a graph showing the results of a direct assay for $PrP^C$ protein in normal hamster brain homogenate wherein the data points and bars represent average±SEM obtained from four independent measurements.
Figure 8:
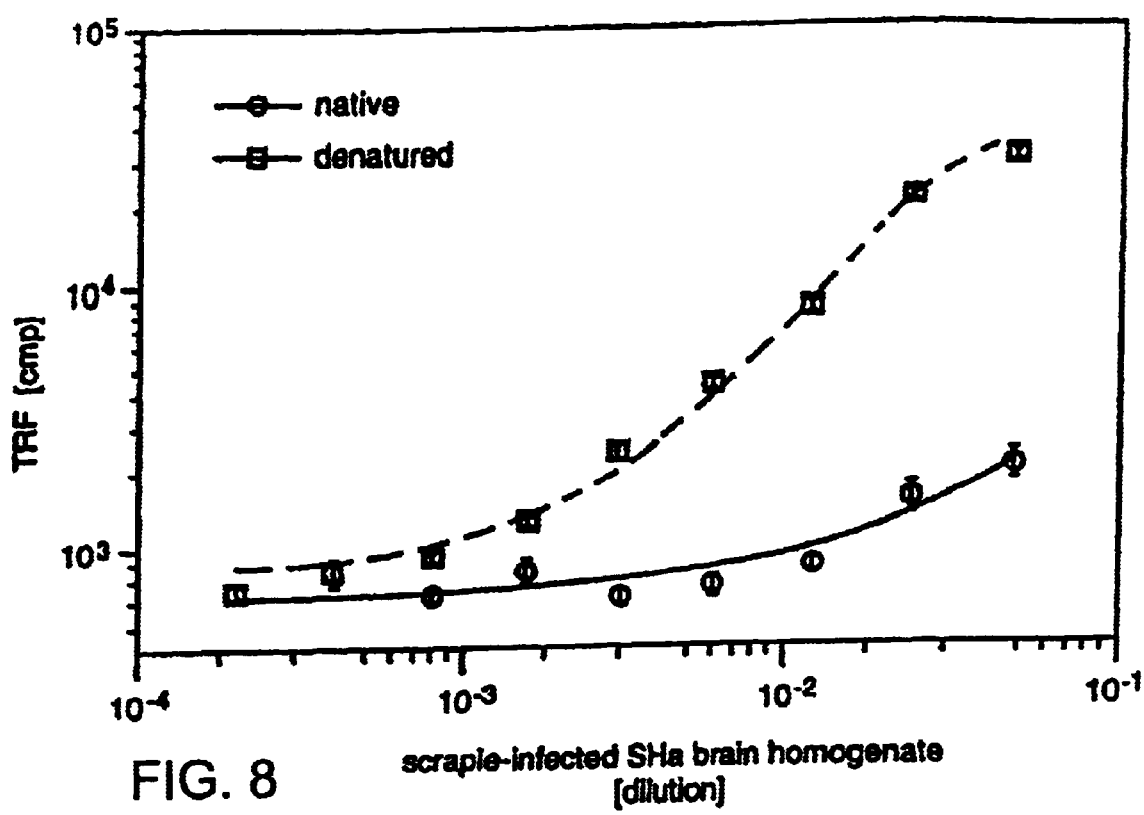
FIG. 8 is a graph showing the results of a direct assay for $PrP^{C+Sc}$ in scrapie infected hamster brain homogenate wherein the data points and bars represent average±SEM obtained from four independent measurements.

Using the differential method, the ratio between the signal of denatured versus native brain $PrP^C$ was for Eu-labeled monoclonal 3F4 IgG 2.2 (FIG. 7), for polyclonal N12 and P31.0. The calibration for $PrP^{Sc}$ gave ratio ≧20 (FIG. 8) for 3F4 Eu-labeled IgG and >4 for N12 and P3 antibodies. By using the formulae developed shown herein, all $PrP^C$ was in full range in α-helical conformation. In contrast, the calculated amount of $PrP^{Sc}$ in infectious, β-sheet conformation was as anticipated close to the total amount of prion protein.

Example 7

Figure 9:
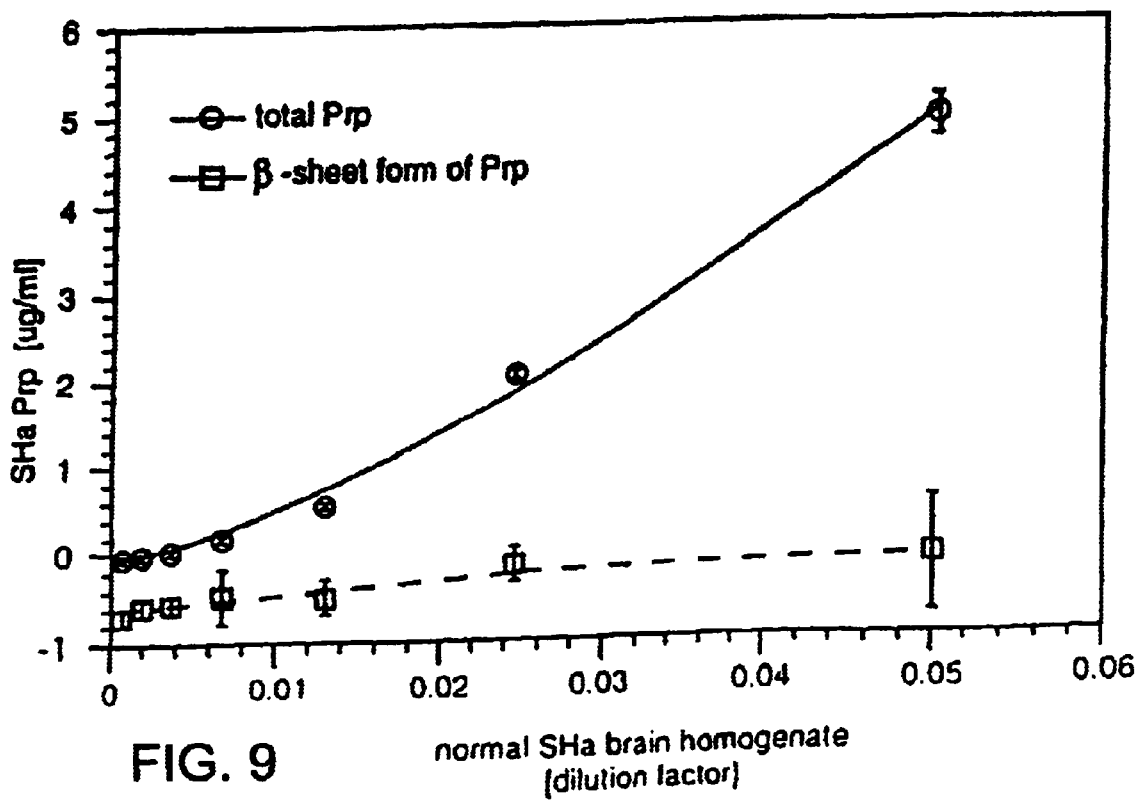
FIG. 9 is a graph showing the total amount of PrP proteins in normal hamster brains and the amount of β-sheet $PrP^{Sc}$ in both brains calculated from the model wherein the data points and bars represent average±SEM obtained from four independent measurements.

Diagnosis of Prion disease Based on Increase of Total Prion Protein Above Physiological $PrP^C$ Levels Accurate quantitative measurement of total PrP by exclusively evaluating the signal of denatured sample (subjected to unfolding treatment) gave an average value of $PrP^C$ in 5% normal Syrian Hamster brain homogenates of 5.0±0.2 μg/ml (Mean±SEM) (FIG. 9). The serial dilution of scrapie (Strain Sc237)-infected hamster brain homogenate into $PrP^{0/0}$ mouse brain homogenate gave values of total PrP 36.0±4 μg/ml (FIG. 10) with broad linearity of the measurement. Because the only known condition for accumulation of prion protein is the accumulation of the infectious $PrP^{Sc}$ form, the increased levels of total PrP in the tested sample is indicative of the presence of prions. This prion assay may be used: (1) in direct mode in brain, tissue samples, body fluids or pharmaceuticals after determination of normal control values; or (2) in indirect mode by detecting the elevation of total PrP in the brain of experimental animal intracerebrally inoculated with tested tissue, body fluid or pharmaceutical sample suspected of containing prions.

Example 8

Diagnosis of Prion Disease Based on Increase of the Signal Ratio Between Denatured vs Native PrP ("Prion Index")

Figures 10, 11:
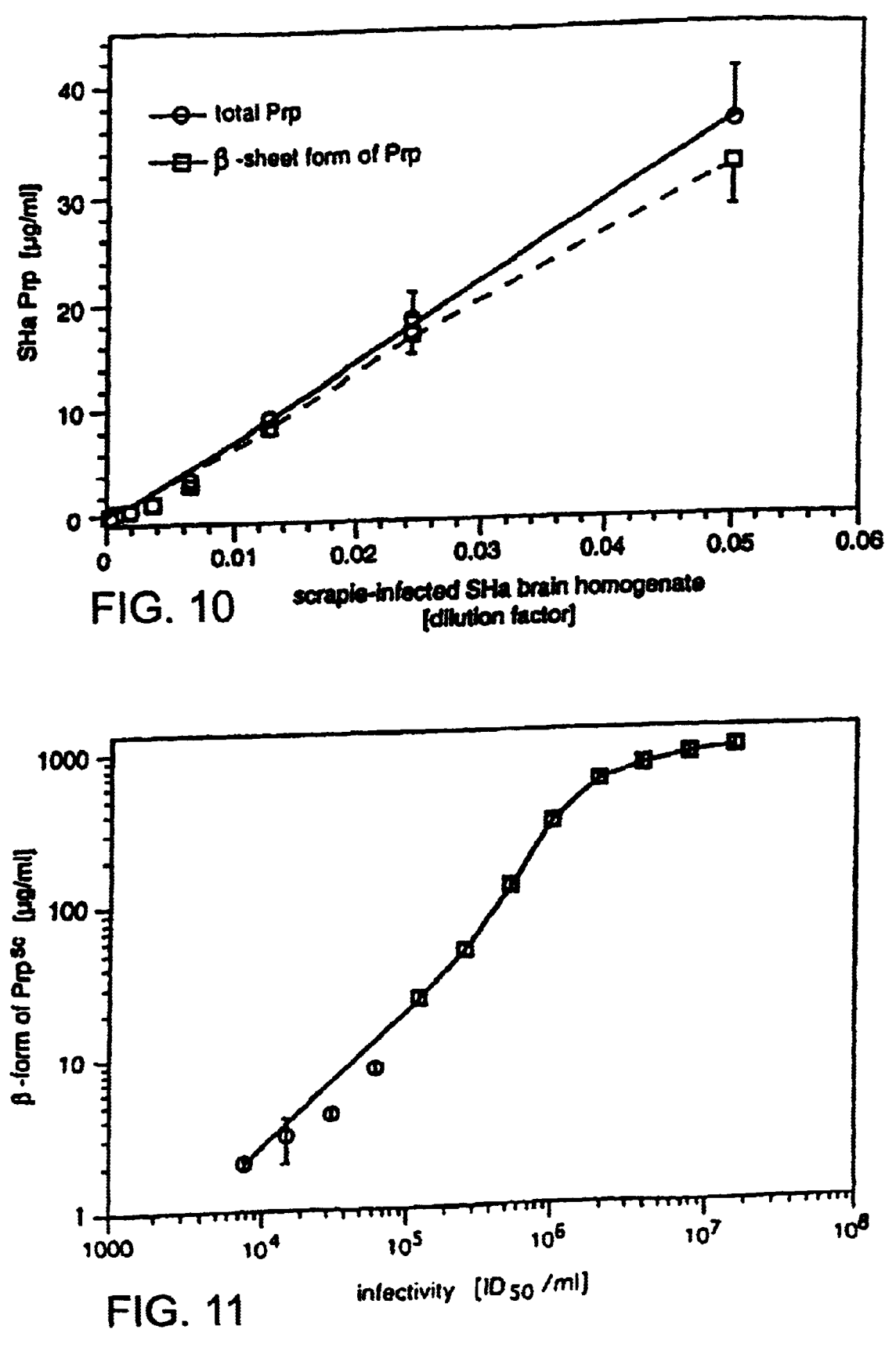

The ratio between antibody affinity for denatured (subjected to unfolding treatment) versus native Syrian hamster brain $PrP^C$ protein is in the broad concentration range for Eu-labeled 3F4 IgG between 0.8–2.2. The ratio in the scrapie infected brain is through the full linearity range above those values (FIG. 11). The "prion index" gives a relative indicator of the presence of infectious $PrP^{Sc}$ and therefore prions. This mode of prion assay may be used: (1) in direct mode in brain, tissue samples, body fluids or pharmaceuticals after determination of the index for normal controls; or (2) in indirect mode by detecting the elevated denatured/native prion protein index in the brain of experimental animals intracerebrally inoculated with tested tissue, body fluid or pharmaceutical sample suspected from containing prions.

Example 9

Diagnosis of Prion Disease From Differential Assay by Calculating $PrP^{Sc}$ Content By using the direct assay and formulae provided here, there is no detectable amount of β-sheet form of $PrP^{Sc}$ in normal brain homogenate. Conversely, most of the total PrP in scrapie-infected hamster brain was due to the accumulation of $PrP^{Sc}$ (FIGS. 9 and 10). The correlation between the prion titer and $PrP^{Sc}$ calculated from the formula has a broad linearity and sensitivity cutoff of ~$10^3$ $ID_{50}$ ml (FIG. 11). The formula gives a quantitative indicator of the presence of PrP protein in abnormal conformation which quantitatively correlates with prion titer. This mode of prion assay may be used (1) in direct mode in brain, tissue samples, body fluids or pharmaceuticals; or (2) in indirect mode, by calculating $PrP^{Sc}$ content in the brain of experimental animals intracerebrally inoculated with tested tissue, body fluid or pharmaceutical samples suspected for containing prions. After establishing a calibration curve between $PrP^{Sc}$ and prion titer, it is possible to estimate the titer directly from $PrP^{Sc}$ content.

Example 10

The Measurement of α-Helix-to -β-Sheet Conversion of PrP Protein in to Screen Prion Generation de novo and Potential Disease Therapeutics The aliquots of a 100 μg/ml solution of the α-helical form of recombinant SHaPrP90–231, or SHaPrP29–231, or corresponding recombinant or synthetic peptides of the prion protein are incubated in 20 mM Na acetate buffer, pH 5.5, for 24 hrs at 37° C. with $10^{-3}$–$10^{-6}$ M concentrations of glycerol, cyclodextrins, heparin, heparin sulfate, Congo Red, cholesterol ester, dimyristoyl phosphatidylcholine. The samples are then divided into two aliquots: (1) untreated, designated native; (2) mixed with final 4M GdnHCl and heated for 5 min at 100° C., designated denatured (unfolding treatment). Both samples are diluted 20-fold by $H_2O$ and aliquots loaded on polystyrene plate activated with glutaraldehyde. The plates, incubated overnight at 5° C., were blocked with TBS, pH 7.8, containing 0.5% BSA (w/v) and 6% Sorbitol (w/v). In the next step, they were washed three time with TBS, pH 7.8 containing 0.05% (v/v) of Tween® 20 and incubated with europium-labeled 3F4 IgG. The plates were developed after additional 7 washing steps in enhancement solution provided by the europium label supplier (Wallac Inc., Turku, Finland) and signal counted on DELFIA 1234 Fluorometer (Wallac Inc., Turku, Finland).

The degree of conversion from α-helical to β-sheet conformation of PrP is calculated from the "prion index" or alternatively from the formulae provided herein. Some compounds which inhibit the conversion by apparently stabilizing the native-like conformation of prion protein may have therapeutic potential in vivo.

Example 11

The assay method is demonstrated on the following example with scrapie-infected Syrian hamster brain homogenate, diluted 4-fold into $PrnP^{0/0}$ mouse brain homogenate:

a) Each plate is calibrated with an inner standard consisting from five dilution points of denatured SHaPrP90–231. The time-resolved fluorescence (TRF) of total PrP is developed with Eu-labeled 3F4 IgG and the time-resolved fluoresence values are plotted as a function of PrP concentration (FIG. 4). The data are fit within a linear or polynomial equation using the least square method and best function is selected for the calculation of denatured PrP:

$$PrP[\mu g/ml] = -0.22935 + 0.00026567*[TRF] + 0.0000000012255*[TRF]^2 \quad (1)$$

b) On the rest of the plate, native and denatured aliquots of scrapie-infected Syrian hamster brain homogenate, diluted 4-fold, and crosslinked to the plastic support were incubated with Eu-labeled 3F4 IgG. The total PrP content is calculated according to the above formula from the fluorescence signal of denatured sample:

| scrapie infected brain homogenate concentration [%] | native TRF [cpm] | denatured TRF [cpm] | $PrP^{C+Sc}$ [μg/ml] |
|---|---|---|---|
| 5 | 4214 | 109814 | 43.7 |
| 1.25 | 1381 | 30804 | 9.1 |
| 0.3125 | 1070 | 11240 | 2.9 | c) The ratio of the fluorescence signals between denatured (subjected to unfolding treatment) and native samples is calculated:

| scrapie infected brain homogenate concentration [%] | native TRF [cpm] | denatured* TRF [cpm] | denatured*/ native ratio |
|---|---|---|---|
| 5 | 4214 | 109814 | 26.1 |
| 1.25 | 1381 | 30804 | 22.3 |
| 0.3125 | 1070 | 11240 | 10.5 |

*denatured indicates it was subjected to unfolding treatment.

The normal value of $PrP^C$ determined from normal hamster brain homogenate is 2.2; the values over 2.2 are considered abnormal and indicate the presence of $PrP^{Sc}$.

d) The excess of fluoresence signal over that expected for α-helical PrP in the transition from native to denatured (unfolded) state is a measure of the amount of PrP$^{Sc}$ and is calculated according the formulae provided:

$$\Delta F_{\beta n \to d} = F_d - (F_n * f_{\alpha n \to d}) \qquad (2)$$

where f=is the maximum value of the factor for the fluorescence signal in the transition from native to denatured state of PrP$^C$; $F_d$ is the fluorescence of denatured (unfolded) sample, and $F_n$ is the fluorescence of native sample The amount of PrP$^{Sc}$ is then calculated from $\Delta F_{\beta n \to d}$ and equation (1):

| scrapie infected brain homogenate concentration (%) | $\Delta TRF_{\beta n \to d}$ [cpm] | PrP$^{Sc}$ [μg/ml] |
|---|---|---|
| 5 | 100543.2 | 38.9 |
| 1.25 | 27765.8 | 8.1 |
| 0.3125 | 8886 | 2.2 |

The positive value calculated for the β-sheet form of prion protein indicates the presence of PrP$^{Sc}$.

Example 12

Standards of Soluble (α-helical) and Insoluble (β-sheet) Forms of βA4 Protein

Soluble forms of βA4 (1–40) and βA4 (1–42) were obtained from Bachem (Torrance, Calif.). One portion of the fresh lyophilized peptide was solubilized in PBS, pH 7.4, containing 20% (v/v) of HFIP (hexafluoroisopropanol; 1,1,1,3,3,3-hexafluoro-2-propanol) or 1% (w/v) SDS (sodium dodecylsulfate) at final protein concentration 50 μM; this protein was designated "soluble" and was stored at –80° C. until use. A second portion of the peptide was resuspended in PBS, pH 7.4 at the final concentration ≧350 μM and incubated for 72 hrs at 37° C. This portion of the protein was designated "insoluble" and was stored until use at –80° C.

Figure 12:
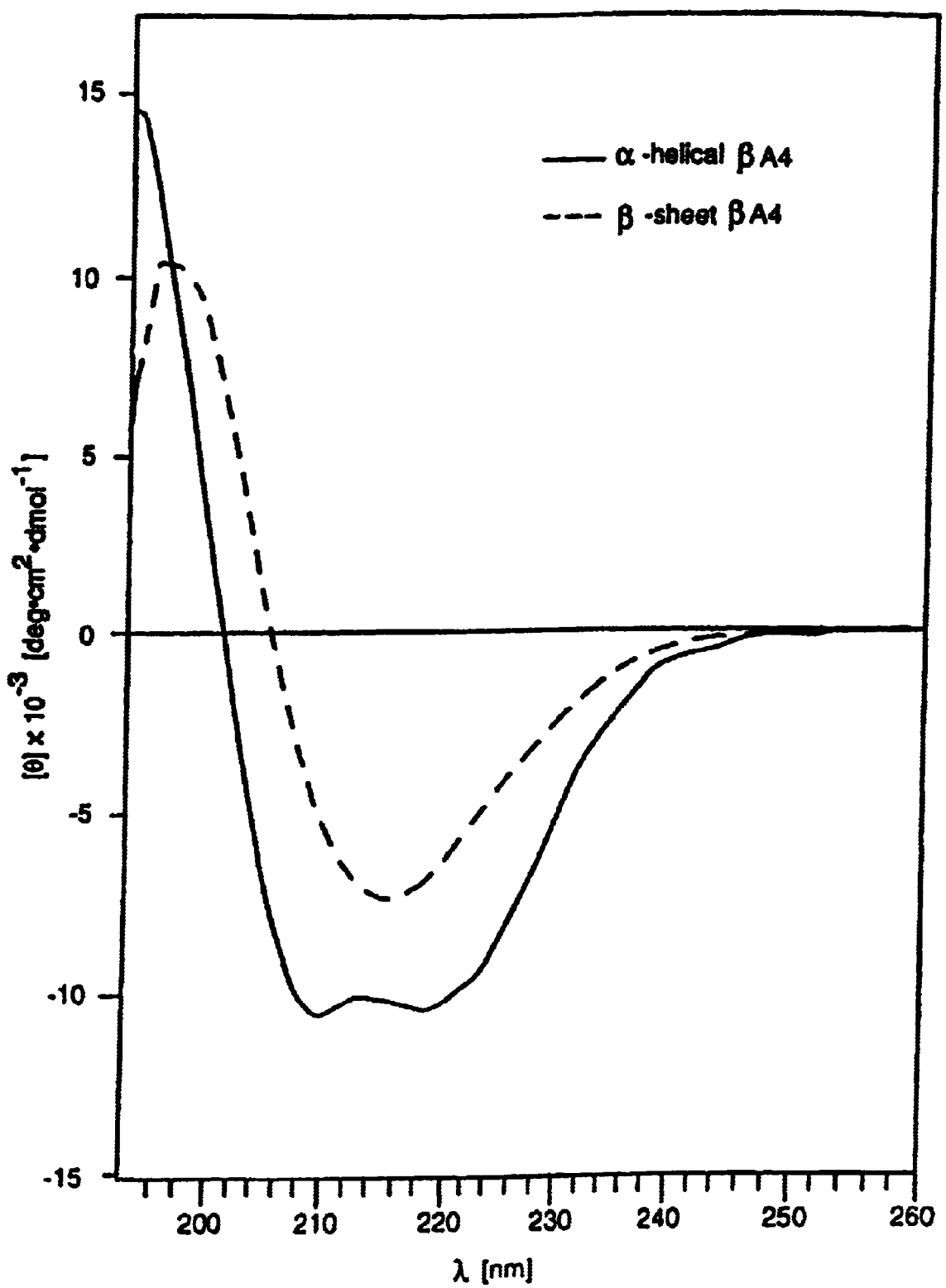
FIG. 12 is a graph of βA4 (1–40) in both α-helical and β-sheet conformations produced by circular dichroism (CD) spectroscopy showing major bonds at 208 and 222 nm for the helical conformation and a single negative band at 217 nm for the predominantly β-sheet conformation (at pH 7.4)

Both proteins were used as a standards for assay development and to establish the sensitivity and linearity range. The CD (circular dichroism) spectroscopy (FIG. 12) demonstrated that soluble protein has an α-helical conformation (see the solid line of FIG. 12). In contrast, the βA4 protein treated for 72 hrs at 37° C. has fully converted into β-sheet conformation (see the dashed line of FIG. 12).

Selection, Labeling and detection Method of Antibodies Used in the Assay

The protocols and methods of antibody production and characterization are generally described elsewhere [Harlow and Lane (1988) supra:726]. The data described in this and following examples were generated with monoclonal antibody 6F3D, developed against synthetic peptide corresponding to the sequence of human βA4 protein (Research Diagnostics Inc., Flanders, N.J.). However, polyclonal antibodies made against synthetic analog of βA4 protein might also be used. Recombinant Fab recognizing denatured forms of βA4 protein might also be used.

βA4 protein in α-helical, β-sheet and random coil conformations were covalently attached to the glutaraldehyde activated polystyrene plates and incubated with serially diluted primary antibody. The amount of IgG reacting with each conformation of βA4 was determined with europium labeled anti-rabbit or anti mouse antibody according usual protocols and the total signal was measured by time-resolved, dissociation-enhanced fluorescence. Antibodies with the signal ratio of denatured (subjected to unfolding treatment) versus β-sheet conformation of βA4 equal or higher than 2 were selected to develop the assay.

Direct and Competitive Assay Format

In direct assay, each sample of dilution curve of α-helical and β-sheet forms of βA4 protein was divided into two aliquots: (1) untreated (designated native); and (2) mixed with final 4M GdnHCl/1% Sarcosyl and heated for 5 min at 100° C. (designated "denatured" meaning it was subjected to unfolding treatment). Both samples were diluted 20-fold by H$_2$O and aliquots loaded on polystyrene plate activated with 0.2% glutaraldehyde for 2 hrs. The plates, incubated overnight at 5° C., were blocked with TBS, pH 7.8, containing 0.5% BSA (w/v) and 6% Sorbitol (w/v). The samples were then washed three time with TBS, pH 7.8 containing 0.05% (v/v) of Tween® 20 and incubated with primary antibodies against βA4 protein (6F3D, Research. Diagnostics Inc., Flanders, N.J.). The samples were washed and then developed with europium-labeled secondary antibodies against mouse IgG (Wallac Inc., Turku, Finland). The plates were developed after an additional 7 washing steps in enhancement solution (Wallac Inc, Turku, Finland) and signal counted on DELFIA 1234 Fluorometer (Wallac Inc., Turku, Finland). The results for analyte indicate marked difference in both available binding sites and affinity anti-βA4 IgG with different conformations of βA4 protein.

The method could be carried out using a competitive assay, where the analyte βA4, in different conformations is preincubated with anti-βA4 IgG and then transferred to the polystyrene plate coated with synthetic βA4 protein in GdnHCl -denatured state, i.e. unfolded βA4 protein.

Differential Test for Various Conformations of βA4

The parameters obtained from direct assay with 6F3D anti-βA4 IgG were plotted as a function of the concentration. The results obtained with βA4 in β-helical conformation (FIG. 13) show a large difference between the signal of β-sheet and denatured protein. The sensitivity limit for denatured βA4 is ≦1 μg/ml and the linearity range is over 2 orders of magnitude. In the experiments with the α-helical form of βA4 (FIG. 14), 6F3D IgG binds equally strongly to both native and denatured forms of the protein. In contrast, the reactivity with the native β-sheet form of the protein only marginally exceeded the background even at high protein concentrations. When the results are expressed as a ratio of the fluorescence of denatured versus native states of the βA4 (FIG. 15), the ratio for α-helical conformation is ≦1 and for βA4 in β-sheet conformation is in a given concentration range ≧1.5.

This effect was further utilized to analyze βA4 samples of unknown conformation where the small increase in signal of Eu-labeled 3F4 IgG after denaturation of βA4 is a characteristic of α-helical conformation. By contrast, the large increase in the signal above the expected change for α-helical conformation is diagnostic of the in β-sheet conformation (FIG. 15) The results may be expressed in two different forms: (1) as a ratio (FIG. 15), where index ≦1.0 for βA4 indicates that the protein was originally in all α-helix conformation and index >1.5 indicates presence of β-sheet conformation; (2) per the formula shown above where the excess increase of signal above that expected for α-helical conformation is proportionate to the amount of βA4 in β-sheet conformation.

Example 13

Figure 13:
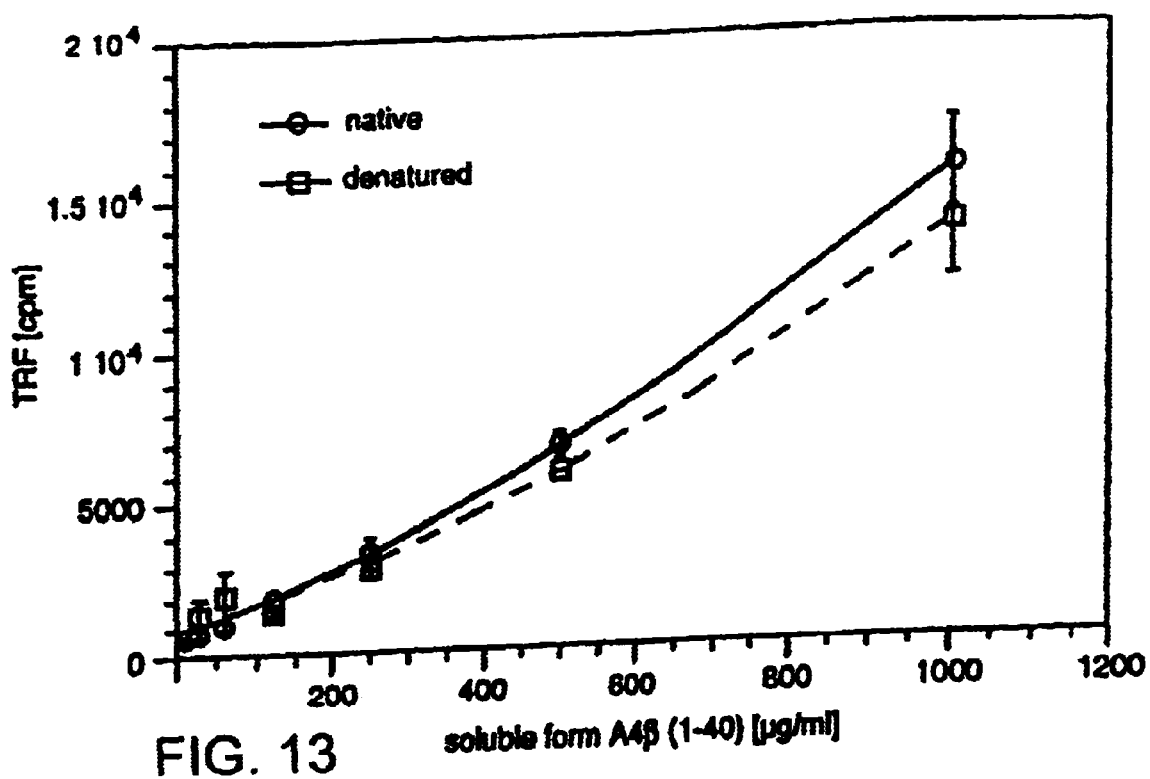
FIG. 13 is a graph of a direct assay of soluble A4β (1–40)
Figure 14:
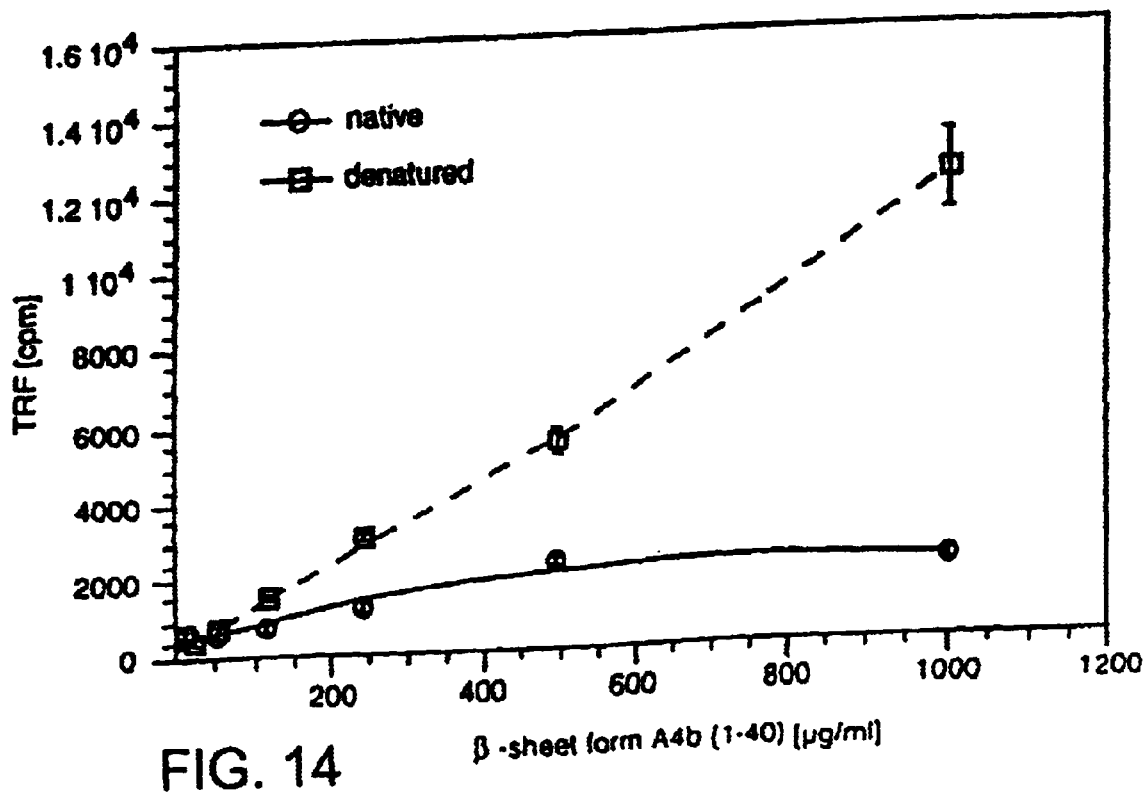
FIG. 14 is a graph of a direct assay of the β-sheet form of A4β (1–40)

Diagnosis of Alzheimer's Disease Based on Increase of Total βA4 Protein Above Physiological Levels Accurate quantitative measurement of total βA4 by exclusively evaluating the signal of denatured sample is apparently more accurate than measurement of βA4 in native conformation (FIGS. 13 and 14). The normal value of the protein may hide a significant portion of the β-sheet form of βA4 protein due to the lower reactivity of this form with antibodies. Because the only known condition for accumulation of βA4 protein is the accumulation of the β-sheet form of βA4 in the brains of patients with Alzheimer's disease, the increased levels of total βA4 in the tested sample is indicative of the presence of pathogenic forms of βA4. This βA4 assay may be used in tissue, body fluids or pharmaceutical sample suspected of containing β-sheet forms of βA4.

Diagnosis of Alzheimer's Disease Based on Increase of the Signal Ration Between Denatured vs. Native βA4 ("βA4 Amyloid Index")

Figure 15:
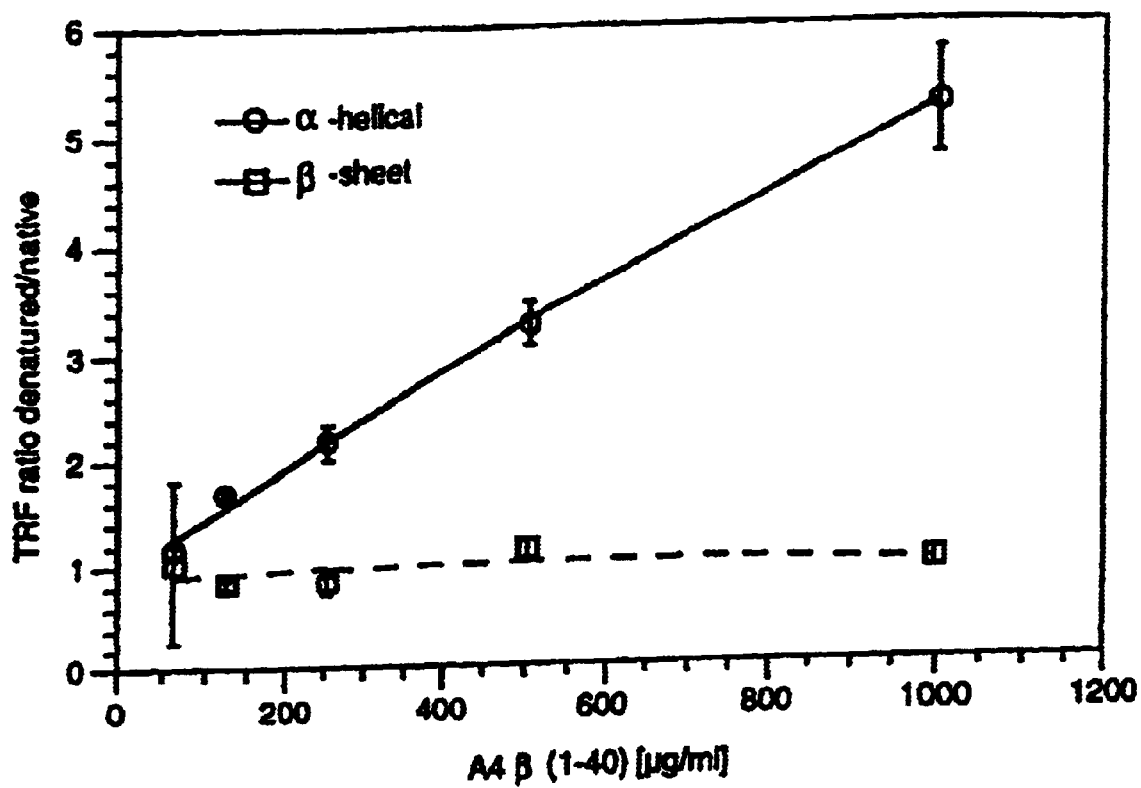
FIG. 15 is a graph showing the ratio of denature to native A4β (1–40)
Figure 16:
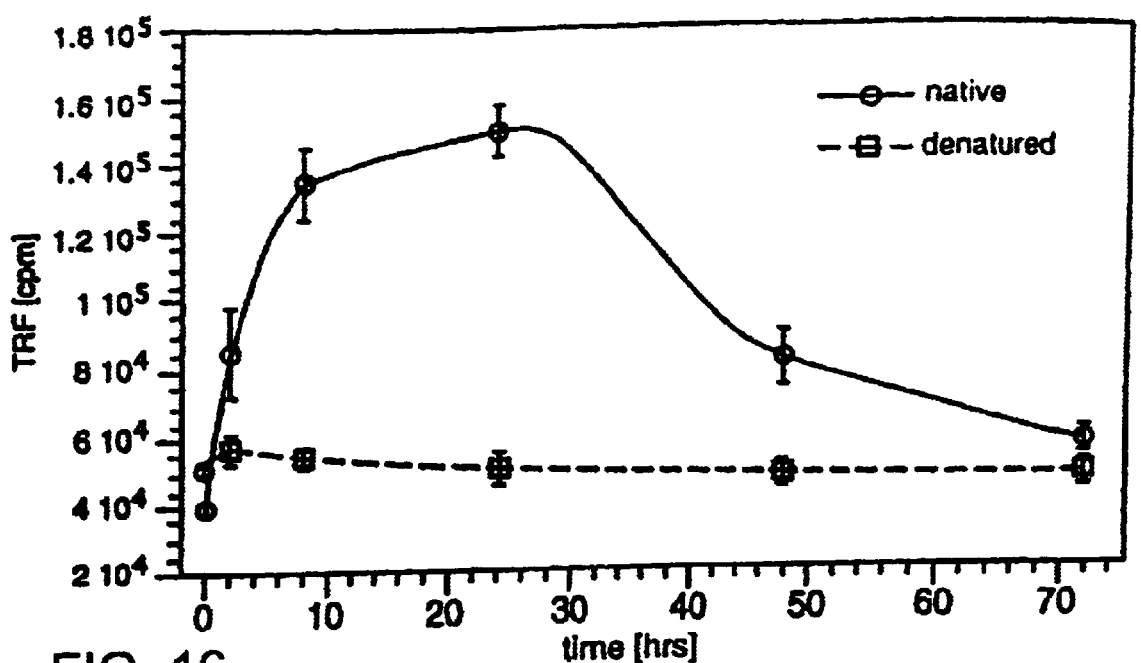
FIG. 16 shows conversion of recombinant ShaPrP90–231 from α-helical to β-sheet conformation during incubation at 37° C. for 72 hrs, as determined by direct differential assay. The increased signal of native conformation at ~24 hrs indicates destabilization of native structure with more open conformation followed by conversion to β-sheet secondary structure (see FIG. 16). The protein concentration was 5 mg/ml.
Figure 17:
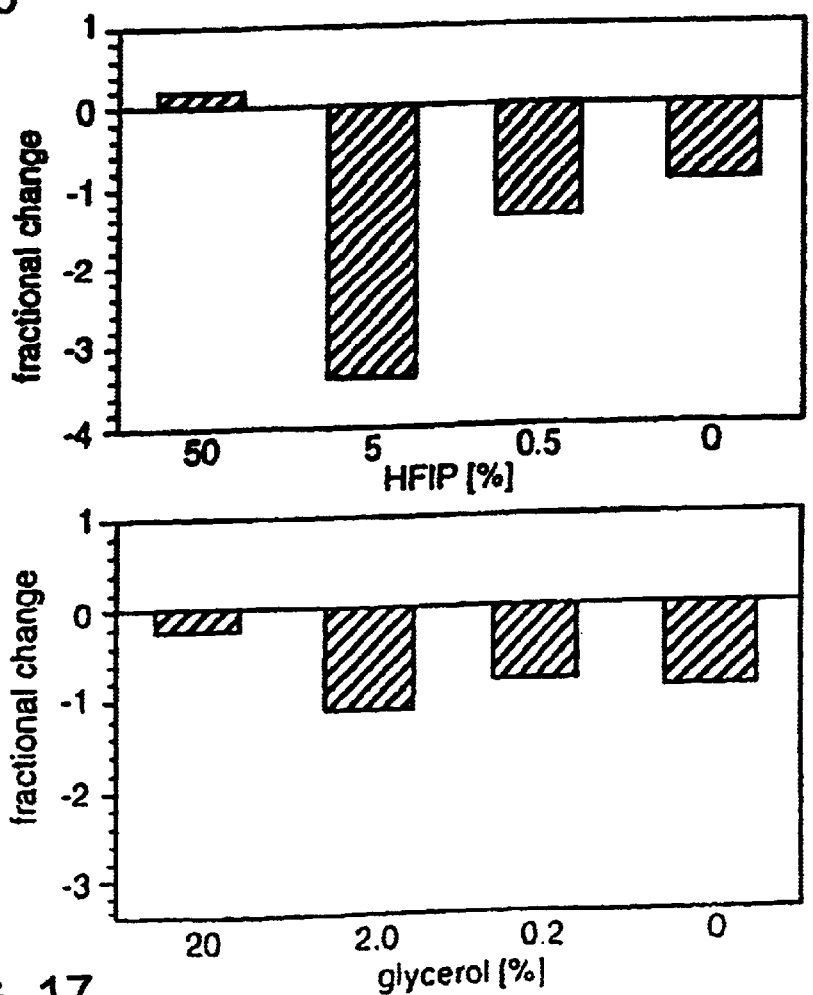
FIG. 17 shows that both HFIP and glycerol are able to prevent α-to-β conformational transition of recombinant ShaPrP90–231. The changes in the TRF signal are expressed as fractional change, where positive value indicates stabilization, negative destabilization. The experimental conditions were as in FIGS. 1 and 16.

The ratio between antibody affinity for denatured (subjected to unfolding treatment) versus native human βA4 protein is in the broad concentration range for 6F3D IgG between 0.8–1.0. The ration for β-sheet βA4 is through the full linearity range above those values (FIG. 15). The "βA4 amyloid index" gives a relative indicator of the presence of pathogenic insoluble β-sheet βA4. This mode of βA4 assay may be used in direct mode in brain, tissue samples, body fluids or pharmaceuticals after determination of the index for normal controls.

Diagnosis of Alzheimer's Disease From Differential Assay by Calculating βA4 Content By using the direct assay and formula shown above, the amount of pathogenic forms of β-sheet βA4 protein can be calculated in brain, tissue samples, body fluids or pharmaceuticals.

Example 14

The Measurement of α-helix-to-β-sheet Conversion of βA4 Protein in vitro to Screen the Potential Disease Therapeutics The aliquots of a 350 μM solution of the α-helical form of synthetic βA4 (1–40, or corresponding recombinant or synthetic peptides of the βA4 protein are incubated in PBS, pH 7.4, for 72 hrs at 37° C. with $10^{-3}$–$10^{-6}$ M concentrations of glycerol, cyclodextrins, heparin, heparin sulfate, Congo Red, cholesterol ester, dimyristoyl phosphatidylcholine. The samples are then divided into two aliquots: (1) untreated, containing 1% Sarcosyl and designated "native"; and (2) mixed with final 4M GdnHCl/1% Sarcosyl and heated for 5 min at 100° C., designated "denatured" meaning subjected to unfolding treatment. Both samples are diluted 20-fold by $H_2O$ and aliquots loaded on polystyrene plate activated with glutaraldehyde. The plates, incubated overnight at 5° C., were blocked with TBS, pH 7.8, containing 0.5% BSA (w/v) and 6% Sorbitol (w/v). In the next step, they were washed three time with TBS, pH 7.8 containing 0.05% (v/v) of Tween® 20 and incubated with 6F3D IgG and then with Eu-labeled anti-mouse antibody. The plates were developed after an additional 7 washing steps in enhancement solution and signal counted on DELFIA 1234 Fluorometer (Wallac Inc., Turku, Finland).

The degree of conversion from α-helical to β-sheet conformation of βA4 is calculated from the "amyloid index" (FIG. 15) or alternatively from the formula shown above. Any compound which inhibits the conversion by stabilizing the α-helical conformation of βA4 protein may have therapeutic potential in vivo by preventing formation of mature amyloid.

Example 15

Standards of Normal and Amyloid Forms of TTR

Soluble forms of TTR were obtained from Sigma Chemical Comp. One portion of the protein was solubilized in 100 mM KCl buffer, pH 7.4, at final protein concentration 0.5 mg/ml; this protein was designated "normal" and was stored at −80° C. until use. The second portion of the protein was converted into amyloid as described [Lai, Colon et al. (1996) *Biochemistry* 35(20):6470–82]. Briefly, the protein was resuspended in 100 mM KCl buffer, containing 50 mM sodium acetate, pH 4.4, at protein concentration 0.2 mg/ml, and incubated for 72 hrs at 37° C. This portion of the protein was designated "amyloid" and was stored until use at −80° C. The turbidimetry and Congo Red binding assay verified the efficient conversion into amyloid [Lai, Colon et al. (1996) *Biochemistry* 35(20):6470–82]. Both proteins were used as standards for the assay development and to establish the sensitivity and linearity range.

Direct Assay Format

The protocols and methods of antibody production and characterization are in general described elsewhere. The data described in this and following examples were generated with commercially available polyclonal antibody, developed against purified human TTR (Accurate Chemical and Scientific Corporation, Westbury, N.Y.).

In the direct assay, each sample of protein taken from the dilution curve of normal and amyloid forms of TTR was divided into two aliquots: (1) untreated and designated "native"; (2) mixed with final 4M GdnHCl/1% Sarcosyl and heated for 5 min at 100° C. and designated "denatured" (subjected to unfolding treatment). Both samples were diluted 20-fold by $H_2O$ and aliquots loaded on polystyrene plate activated with 0.2% glutaraldehyde for 2 hrs. The plates, incubated overnight at 5° C., were blocked with TBS, pH 7.8, containing 0.5% BSA (w/v) and 6% Sorbitol (w/v). In the next step, they were washed three times with TBS, pH 7.8 containing 0.05% (v/v) of Tween 20 and incubated with primary antibodies against TTR (Accurate Chemical and Scientific Corporation, Westbury, N.Y.), washed and then developed with europium-labeled secondary antibodies against rabbit IgG (Wallac Inc., Turku, Finland). The plates were developed after an additional 7 washing steps in enhancement solution and signal counted on DELFIA 1234 Fluorometer (Wallac Inc, Turku, Finland).

Example 16

Diagnosis of SSA and FAP Based on Increase of the Signal Ration Between Denatured vs. Native TTR ("TTR AMYLOID INDEX")

Figure 18:
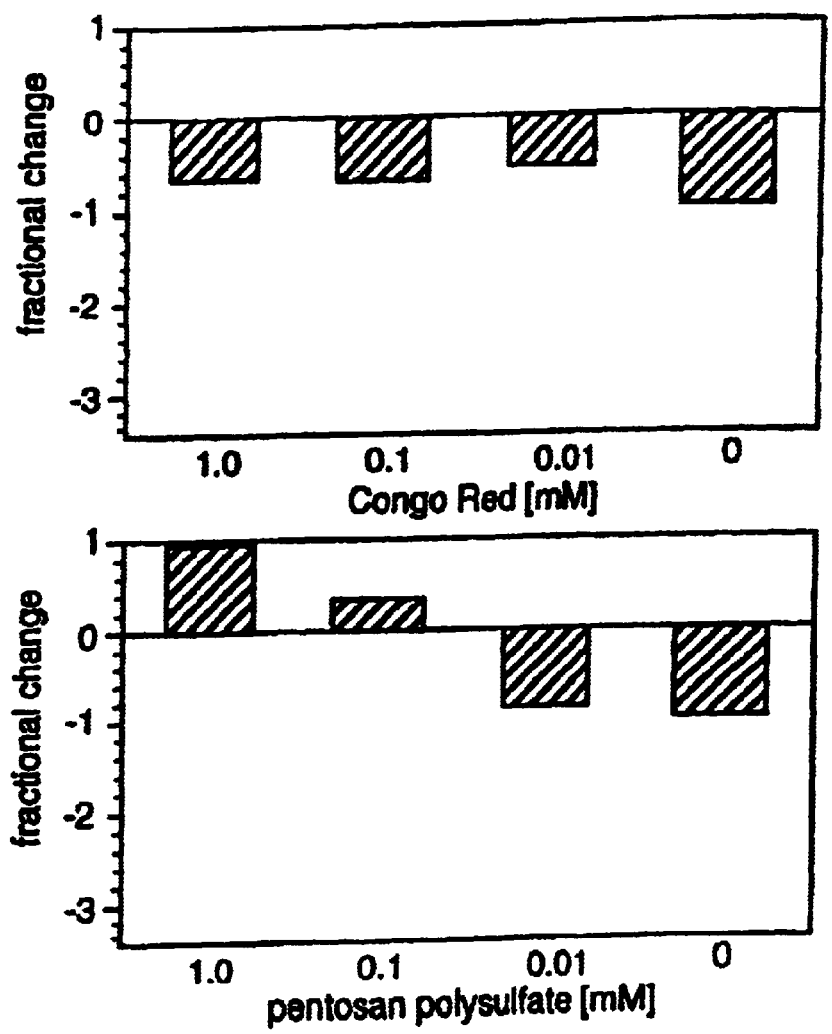
FIG. 18: Pentosan polysulphate stabilizes native conformation of ShaPrP90–231 at low concentrations; Congo red has no effect on stability of ShaPrP90–231. The changes in the TRF signal are expressed as fractional change, where positive value indicates stabilization, negative destabilization. The experimental conditions were as in FIGS. 1 and 16.

The ratio between antibody affinity for denatured (unfolded) versus native form of normal human TTR is in the broad concentration range for polyclonal antibody 1–3:3. The ratio for amyloid form of TTR is through the full linearity range between 0.7–1.0 (FIG. 18). The "TTR amyloid index" gives a relative indicator of the presence of pathogenic, insoluble and amyloid-forming TTR. This mode of TTR assay is being used in direct mode in brain, tissue samples, body fluids or pharmaceuticals after determination of the index for normal controls.

Diagnosis of SSA and FAP From Differential Assay by Calculating TTR Amyloid Content By using the direct assay formula (FIG. 19), the amount of amyloid form of TTR can be calculated in peripheral nerve, tissue samples, body fluids or pharmaceuticals. In formula (FIG. 19), the lower than expected increase of signal for normal conformation is proportional to the amount of TTR in amyloid conformation.

Example 17

The Measurement of Normal-to-amyloid Conversion of TTR in vitro to Screen the Potential Disease Therapeutics The aliquots of a 0.2 mg/ml solution of the normal form of synthetic TTR, or corresponding recombinant or synthetic peptides of the TTR are incubated in 100 mM KCl buffer, containing 50 mM of sodium acetate, pH 4.4 for 72 hrs at 37° C. with $10^{-3}-10^{-6}$ M concentrations of tested organic compounds. The samples are then divided into two aliquots: (1) untreated, containing 1% Sarcosyl and designated "native"; (2) mixed with final 4M GdnHCl/1% Sarcosyl and heated for 5 min at 100° C., designated "denatured." Both samples are diluted 20-fold with $H_2O$ and aliquots loaded on polystyrene plate activated with glutaraldehyde. The plates, incubated overnight at 5° C., were blocked with TBS, pH 7.8, containing 0.5% BSA (w/v) and 6% Sorbitol (w/v). In the next step, they were washed three time with TBS, pH 7.8 containing 0.05% (v/v) of Tween® 20 and incubated with polyclonal anti-TTR antibody (Accurate Chemical and Scientific Corporation, Westbury, N.Y.) and then Eu-labeled anti-rabbit antibody. The plates were developed after additional 7 washing steps in enhancement solution and the signal counted on DELFIA 1234 Fluorometer (Wallac Inc., Turku, Finland).

Figure 19:
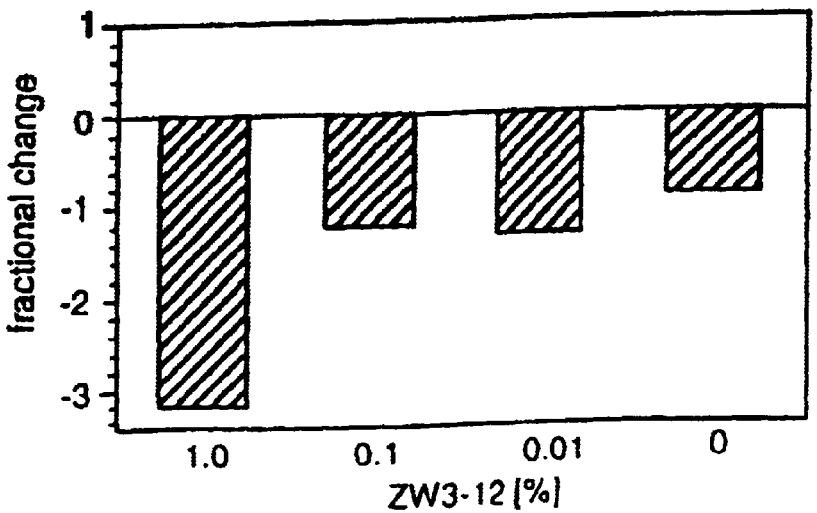
FIG. 19: Zwitterionic detergent ZW3-12 destabilized native conformation of α-helical Sha90–231. The experimental conditions were as in FIGS. 1 and 16; the changes in the TRF signal are expressed as fractional change, where positive value indicates stabilization, negative destabilization.
Figure 20:
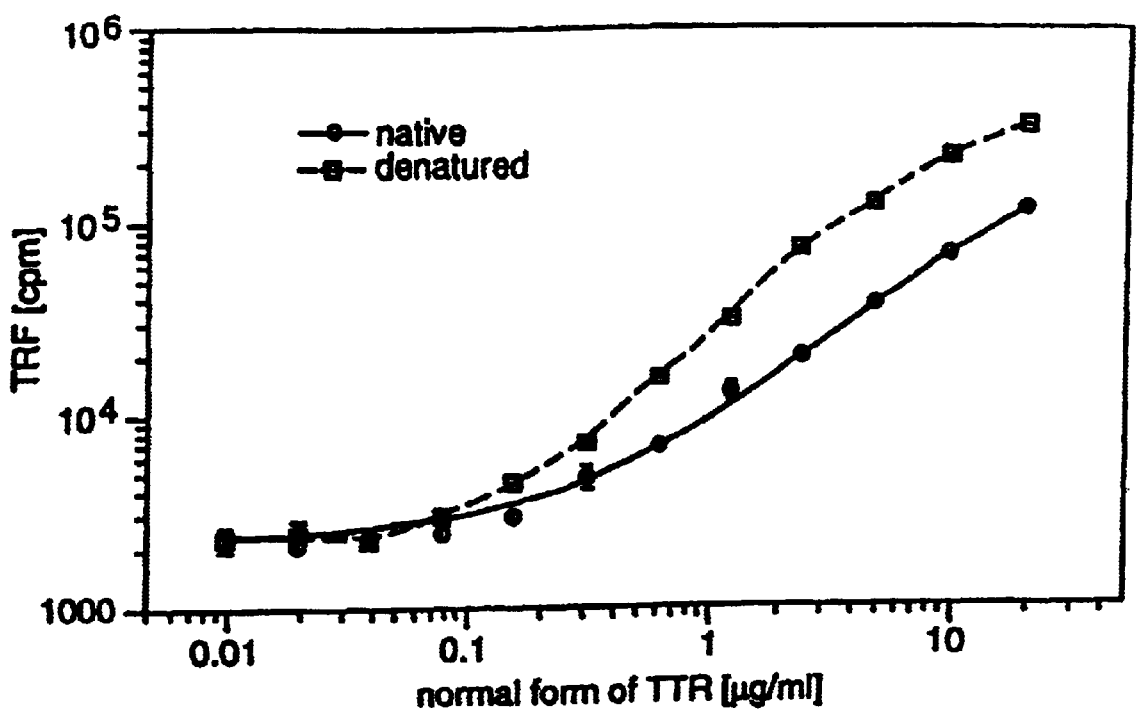
FIG. 20 shows calibration of a direct assay with purified human TTR in normal conformation. The plates were developed with the anti-TTR primary antibodies (Accurate Chemical and Scientific Corporation, Westbury, N.Y.) and secondary Eu-labeled anti-rabbit antibody. The data points and bars represent average±SEM obtained from four independent measurements.
Figure 21:
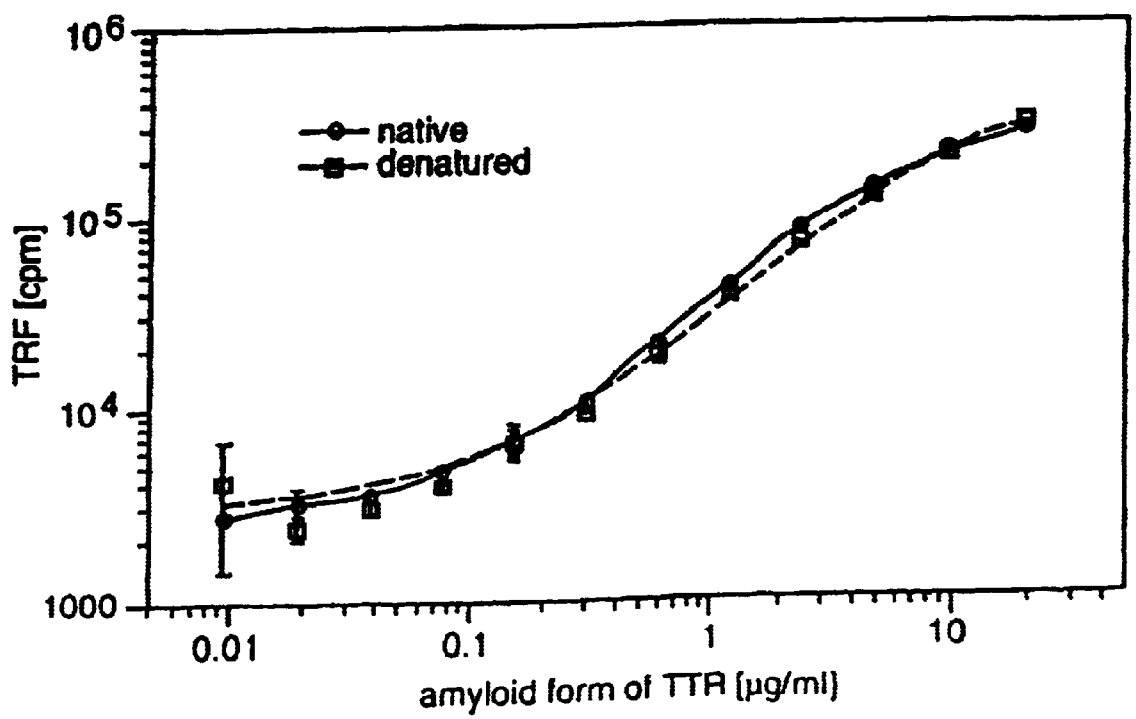
FIG. 21 shows calibration of direct assay with purified human TTR in amyloid conformation. The plates were developed with anti-TTR primary antibodies and secondary Eu-labeled anti-rabbit antibody. The data points and bars represent average±SEM obtained from four independent measurements.
Figure 25:
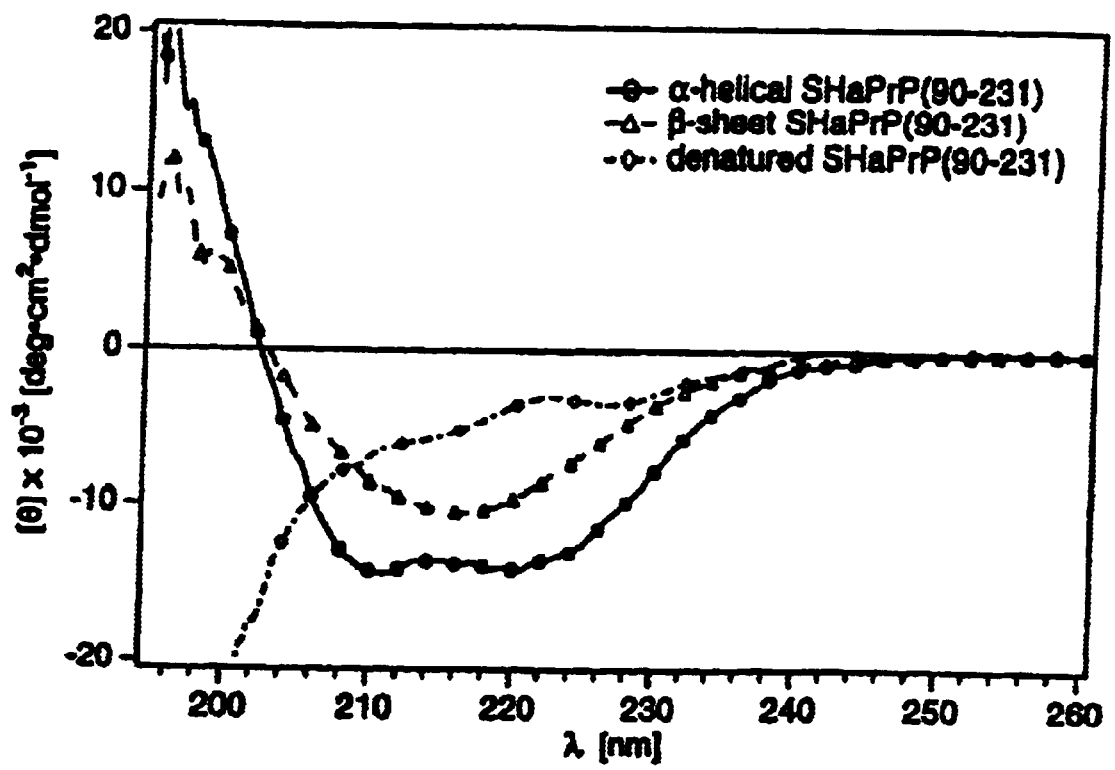
FIG. 25 is a graph as determined by circular dichroism (CD) spectroscopy of SHaPrP (90–231) purified from *E. coli*.
Figure 26:
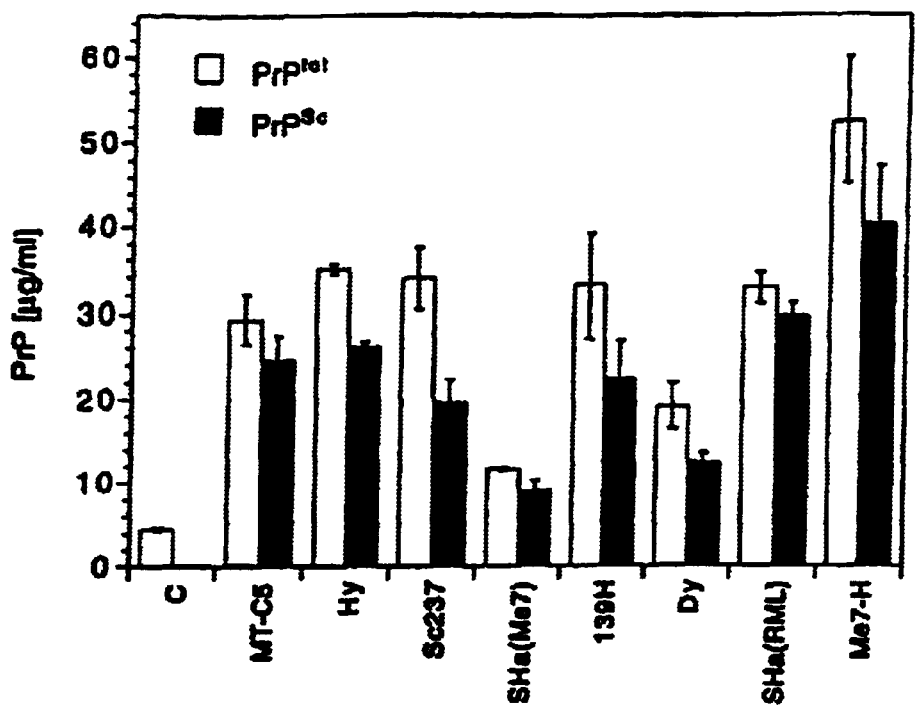
Figure 27:
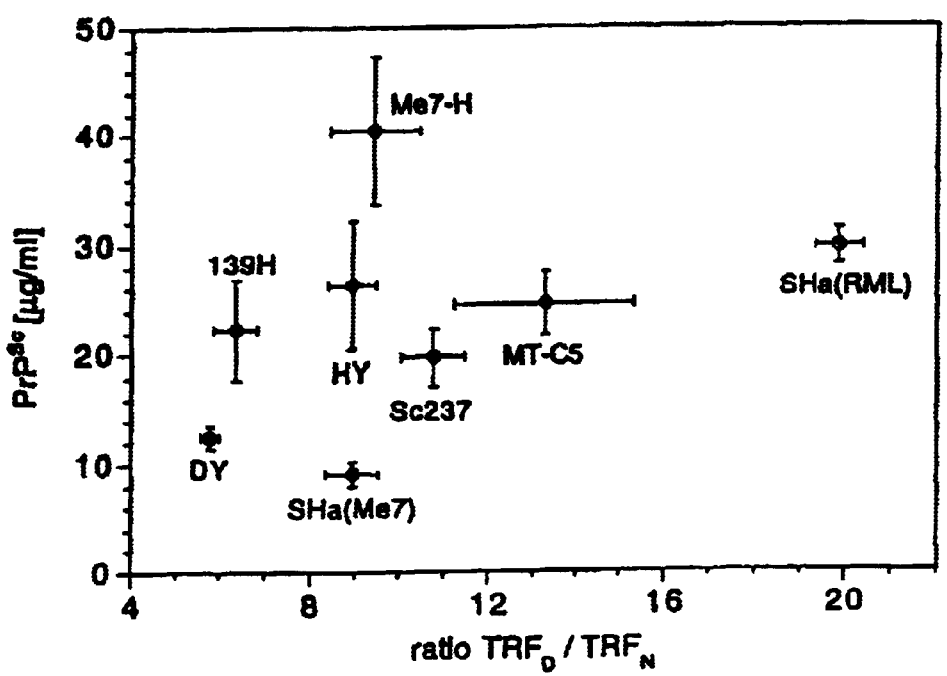
Figure 28:
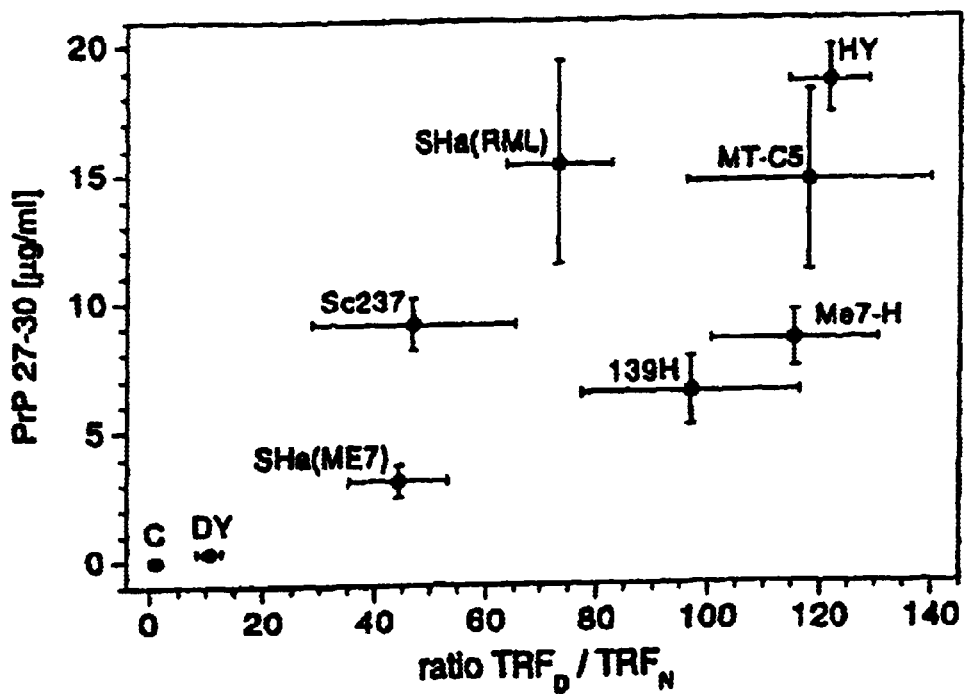

The degree of conversion from normal to amyloid conformation of TTR is calculated from the "amyloid index" (FIG. 18) or alternatively from the formula (FIG. 19). Any compound which inhibits the conversion by stabilizing normal conformation of TTR may have therapeutic potential in vivo by preventing formation of mature amyloid.

Example 18

Typing of Prion Isolates (Strains) in Syrian Hamsters

Syrian hamsters (LVG/LAK) were infected by intracerebral injection of the following hamster adapted scrapie isolates, i.e., different groups of hamsters were infected with individual strains of prions as follows: Drowsy (Dy), 139H, Hyper (Hy), Me7, MT-C5, and Sc237. The animals were euthanized in terminal stages of disease and their brains immediately frozen and stored at −70° C. Brains were homogenized on ice by 3×30 sec strokes of PowerGen homogenizer (Fisher Scientific, Pittsburgh, Pa.) in PBS, pH 7.4, containing protease inhibitors cocktail (PMSF 5 mM, Aprotinin and Leupeptin 4 µg/ml). Resulting 10% (w/v) homogenates were spun for 5 min at 500 g at table top centrifuge. The supernatant was mixed 1:1 with 4% Sarcosyl in PBS, pH 7.4 and divided into two aliquots: (1) untreated and designated native; (2) mixed with a final concentration of 4M GdnHCl and heated for 5 min at 80–100° C. and designated denatured—subjected to unfolding treatment. Both samples were diluted 20-fold by $H_2O$ and aliquots loaded on polystyrene plate activated for 1 hr with 0.2% glutaraldehyde in PBS. The plates, incubated overnight at 5° C., were blocked with TBS, pH 7.8, containing 0.5% BSA (w/v) and 6% Sorbitol (w/v). In the next step, they were washed three times with TBS, pH 7.8 containing 0.05% (v/v) of Tween 20 and incubated for 2 hrs with Europium-labeled monoclonal antibody 3F4. The plates were developed after an additional 7 washing steps in enhancement solution provided by the Europium label supplier (Wallac Inc., Turku, Finland) and signal counted on DELFIA 1234 Fluorometer (Wallac Inc., Turki, Finland). The $PrP^{Sc}$ content and "prion index" (ratio of antibody binding to (unfolded) denatured:native PrP protein) were calculated as described in Examples 11 and 8 and plotted in xy coordinates as shown in FIG. 24. Other samples tested and resulting in the same calculations could be presumed to have the same strain of prion therein.

Example 19

Prion Strains

Syrian hamsters (LVG:Lak) were infected by intracerebral injection of the following hamster-adapted scrapie isolates: Drowsy (DY), 139H, Hyper (HY), Me7-H, MT-C5, Sc237, SHa(Me7), and SHa(RML). The Sc237 strain described in Marsh et al., *J Infect. Dis.*, 131:104–110 (1975) was passaged repeatedly in golden Syrian hamsters (LVG:Lak, Charles River Laboratories). This strain appears to be indistinguishable from strain 263K (see Kimberlin et al., *J. Gen. Virol.*, 34:295–304 (1977)). The MT-C5 strain was isolated in Syrian hamsters (LVG:Lak) from a cow infected with a second passage of sheep scrapie (see Hebbs et al., Bovine Spongeform Encephalopathy: The BSE Dilema, 84–91 (Springer, N.Y. 1996)). For the Me7 hamster isolate see Kimberlin et al. The DY and HY hamster strains are disclosed in Marsh et al., *J. Gen. Virol.*, 72:589–594 (1991). The 139A isolate was obtained after over 20 passages of the Chandler isolate in mice (see Dickenson et al., Slow Virus Disease of Animals in a Man (ed. Kimberlin, RH) 209–241 (North Holland Pub. Amsterdam 1976)). Passage of mouse 139A prions in LVG:Lak golden Syrian hamsters produced the 139H isolate (Kimberlin et al., *Micro. Pathog.*, 2:405–415 (1987)). After six passages in Syrian hamsters, 139H prions were as per Kimberlin et al. Strains SHa(Me7) and SHa(RML) generated by passage of the Me7 strain of scrapie through chimeric Tg(MH2M) and then twice in Syrian hamsters (Scott et al., *J. Virol.*, 71:9032–9044 (1997)).

The animals were euthanized in the terminal stages of disease and their brains immediately frozen and stored at 70° C. Brains were homogenized on ice by three 30-sec strokes of a PowerGen homogenizer (Fisher Scientific, Pittsburgh, Pa.) in PBS, pH 7.4, containing protease inhibitors (5 mM PMSF; aprotinin and leupeptin, 4 µg/ml each). Resulting 10% (w/v) homogenates were spun for 5 min at 500 g in a tabletop centrifuge; supernatant was mixed 1:1 with 4% Sarkosyl in PBS, pH 7.4.

Prion Bioassays

The titer of Sc237 prions was determined in 5% (w/v) brain homogenate by incubation time assay in groups of 4 Syrian hamsters as described in Prusiner et al. *Cell*, 35:349–358 (1983).

Example 20

Expression, Purification, and Refolding of Recombinant SHaPrP(90–231)

For the development and calibration of conformation-dependent immunoassays, recombinant SHaPrP (90–231) was refolded into α-helical or β-sheet conformations as described in (Mehlhorn et al, Biochemistry, 35:5528–5537 (1996)). PCR (Perkin-Elmer) was used to amplify the DNA corresponding to different portions of SHaPrP for ligation into *Escherichia coli* secretion vectors. Clones containing the PrP insert were sequenced and transformed into the protease-deficient expression strain 27C7 (ATCC# 55244). For purification, 100 g of *E. coli* paste was resuspended in 1 L of 25 mM Tris-HCl, pH 8.0/5 mM EDTA (buffer A). This was centrifuged at 10,000×g for 20 min and the supernatant containing soluble periplasmic proteins was discarded. The pellet was resuspended in 1 L of buffer A, passed through a cell disrupter twice (Microfluidics International, model MF 110), and centrifuged at 30,000×g for 1 h, after which the supernatant was discarded and the pellet was washed once in buffer A and centrifuged again at 30,000×g for 1 h. The pellet was subsequently solubilized in 8 M GdnHCl/25 mM Tris-HCl, pH 8.0/100 mM DTT (buffer B) and aliquots of 6 mL of the supernatant containing ~200 mg total protein were separated by size-exclusion chromatography (SEC) followed by reversed phase high performance liquid chromatography (RP-HPLC) employing a 25 mm×25 cm C-4 column (Vydac); Buffer 1; $H_2O$/0.1% TFA, Buffer 2; acetonitrile/0.09% TFA, flow rate 5 mL/min.

Samples of the reduced protein and the refolded oxidized form were concentrated using a Centricon (Amicon) with a molecular weight cutoff of 10,000 Da. The buffer for the reduced protein was 10 mM MES, pH 6.5, whereas the oxidized form was concentrated in the refolding buffer described above. Circular dichroism (CD) spectroscopy on a Jasco 720 spectropolarmeter, as described in Safar et al., *J. Biol. Chem.,* 268:20276–20284 (1993), confirmed that the reduced protein refolded into a β-sheet conformation, and the oxidized protein refolded into an α-helical conformation.

Example 21

Purification of $SHaPrP^{C}$ and $SHaPrP^{Sc}$ From Brain $SHaPrP^{C}$ was purified in a manner similar to that described in Pan et al., *Proc. Natl. Acad. Sci. USA,* 90:10962–10966 (1993). Protein content was determined by amino acid analysis. The purity of $PrP^{C}$ was 95%, as demonstrated by SDS-PAGE followed by silver staining and Western blot.

$SHaPrP^{Sc}$ was purified from a standard pool of scrapie strain Sc237-infected hamster brains in a manner similar to that described in Turk et al., *Eur. J. Biochem.,* 176:21–30 (1988). The infectivity of this pool was 7.3 $ID_{50}$/ml, as determined by an incubation time assay on Syrian hamsters after intracerebral inoculation, and specific infectivity was 8.2 $ID_{50}$/mg of $PrP^{Sc}$. The preparation was considered homogeneous, with one major band on SDS-PAGE after silver staining and Western blots.

Example 22

Labeling of Antibodies

The data were generated with monoclonal antibody 3F4, described in Kascsak et al., *J. Virol.,* 61:3688–3693 (1987).

The IgG was purified from ascitic fluid by Protein A chromatography on a Pharmacia FPLC column and labeled with Europium-chelate of N-(p-isothiocyanatobenzyl)-diethylenetriamine-$N^1$, $N^2$, $N^3$, $N^3$-tetraacetic acid (DTTA) at pH 9.6 for 16 h at room temperature according to manufacturer's protocols (Wallac Inc., Turku, Finland). The final Eu/IgG molar ratio was 13.

Example 23

Immunoassay for $PrP^{Sc}$ by Dissociation-Enhanced Time-Resolved Fluorescence Spectroscopy (TRF)

Each sample was divided into two aliquots: i) untreated and designated native and ii) mixed to a final concentration of 4 M GdnHCl , heated for 5 min at 80° C., and designated denatured (subjected to unfolding treatment). Both samples were immediately diluted 20-fold with $H_2O$ containing protease inhibitors (5 mM PMSF; aprotinin and leupeptin, 4 μg/ml each), and aliquots were loaded on a 96-well polystyrene plate that was previously activated for 1 h with 0.2% glutaraldehyde in PBS, pH 7.4. The plates were incubated overnight at 5° C. and then blocked with TBS, pH 7.8 containing 0.5% BSA (w/v) and 6% Sorbitol (w/v) for 2 h at room temperature. In the next step, they were washed three times with TBS, pH 7.8 containing 0.05% (v/v) of Tween 20 and incubated at room temperature for 2 h with Europium-labeled 3F4 antibodies. The plates were developed after seven washing steps in enhancement solution provided by the Europium label supplier (Wallac Inc, Turku, Finland), and the signal was counted on a DELFIA 1234 (Wallac Inc, Turku, Finland) fluorometer.

Example 24

Calibration of the Conformation-Dependent Immunoassay for PrP

The assay was calibrated for different conformations of PrP in the presence of 5% (w/v) brain homogenate obtained from PrP-deficient (Prnp$^{0/0}$ mice as described in Büehler et al., *Nature,* 356:577–582 (1992). The homogenate was spiked with purified recombinant SHaPrP(90–231) in α-helical or β-sheet conformations, as determined by CD spectroscopy, and with $PrP^{C}$ and $PrP^{Sc}$ purified from SHa brains. The data on antibody binding to denatured recombinant α-helical SHaPrP(90–231) or SHa brain $PrP^{C}$ were plotted as a function of the binding to the native protein and fit by the least squares regression program to obtain the correlation coefficient $f_\alpha$.

Example 25

Ratio of Antibody Binding to Denatured/Native PRP and Quantification of $PRP^{Sc}$ The ratio between binding of Eu-labeled IgG to PrP in native and denatured (unfolded) conformations measured by TRF was designated $TRF_D/TRF_N$. The following s a mathematical model which can be used to calculate the content of β-sheet-structured PrP in an unknown sample directly:

$$[PrP_\beta]\sim\Delta TRF_\beta = TRF_D - (TRF_N * f_\alpha) \qquad \text{(FORMULA 1)}$$

In formula 1 an excess of antibody binding to PrP protein in the transition from native to denatured state (unfolded) over that expected for α-helical conformation is directly proportional to the amount of PrP protein in β-sheet conformation.

Symbols in the equations are as follows: $\Delta TRF_\beta$, change in the time-resolved fluorescence of PrP in β-sheet conformation during the transition from the native to denatured state;

TRF$_D$, time-resolved fluorescence of PrP in the denatured (i.e. unfolded) state;

TRF$_N$, time-resolved fluorescence of PrP in the native conformation; and f$_c$, the correlation coefficient for dependency of TRF$_D$ on TRF$_N$ obtained with serially diluted reduced SHa brain homogenate and with purified SHaPrP$^C$. The coefficient was obtained by fitting the plot of antibody binding to (unfolded) denatured/native protein by the nonlinear least squares regression program.

Example 26

Precipitation of Prions by Sodium Phosphotungstate

Brain homogenate [5% (w/v)] containing 2% Sarkosyl was mixed with stock solution containing 4% sodium phosphotungstate (NaPTA) and 170 mM MgCl$_2$, pH 7.4, to obtain a final concentration of 0.2–0.3% NaPTA. Typically, 1 ml samples were incubated for 16 h at 37° C. on a rocking platform and centrifuged at 14,000×g in a tabletop centrifuge (Eppendorf) for 30 min at room temperature. The optional treatment with 25 µg/ml of proteinase K for 1 h at 37° C. was performed before or after precipitation (decontamination pretreatment) The pellet was resuspended in H$_2$O containing protease inhibitors (0.5 mM PMSF; aprotinin and leupeptin, 2 µg/ml each) and assayed by conformation-dependent immunoassay of the invention.

Example 27

Equilibrium Dissociation and Unfolding in GdnHCl

Aliquots of 5% (w/v) brain homogenates in PBS, pH 7.4 containing 2% Sarkosyl and protease inhibitor cocktail (5 mM PMSF; aprotinin and leupeptin, 4 µg/ml each) were mixed manually to the final concentration of GdnHCl and constant protein concentration in a sample and equilibrated for 16 h at 23 ° C. The concentration of stock solution of 8 M GdnHCl (Pierce, Rockford, Ill.) in TBS, pH 7.4 was controlled by refractometry. Equilibrated samples were diluted 20-fold to the same final protein and GdnHCl concentration and assayed with Eu-labeled 3F4 IgG in conformation-dependent immunoassays as described.

The raw data from each assay were converted into a ratio of antibody binding to (unfolded) denatured/native PrP or the apparent fractional change of unfolding: F$_{app}$ Safar et al., J. Biol. Chem., 268:20276–20284 (1993) and Safar et al., Biochemistry, 33:8875–8883 (1994) by using the formula F$_{app}$=(Y$_{obsd}$-Y$_N$)/(Y$_U$-Y$_N$), where Y$_{obsd}$ is the observed value of the parameter and Y$_N$ and Y$_U$ are the values of the parameters for native and unfolded forms, respectively, at the given GdnHCl concentration.

Example 28

Electron Microscopy

Samples were prepared on carbon-coated 1,000 mesh copper grids that were glow discharged prior to staining. 5 µl samples were absorbed for ~30 sec and washed with 2 drops of water. Contrast was provided by NaPTA retained as positive staining from the NaPTA precipitation step in the preparation; no additional staining was used. After drying, samples were viewed in a Jeol 100CX II electron microscope at 80 kV at a standard magnification of 40,000. The magnification was calibrated with negatively stained catalase crystals.

The instant invention is shown and described herein in what is considered to be the most practical, and preferred embodiments. It is recognized, however, that departures may be made therefrom, which are within the scope of the invention, and that obvious modifications will occur to one skilled in the art upon reading this disclosure.

What is claimed:

1. A method of determining the amount of protease sensitive PrP$^{Sc}$ in a sample, comprising:

determining the total amount of PrP$^{Sc}$ in a unit amount of a sample;

subjecting the sample to limited protease treatment with proteinase K under conditions sufficient to hydrolyze substantially all protein in the sample except for protease insensitive PrP 27–30;

determining the amount of treatment insensitive PrP 27–30 in a unit amount of sample subjected to proteinase K treatment; and subtracting the amounts of treatment insensitive PrP27–30 from the total, amount of PrP$^{Sc}$ to obtain the amount of treatment sensitive PrP$^{Sc}$ in the sample.

2. The method of claim 1, wherein the total amount of disease related conformation of the protein and amount of treatment insensitive protein are determined using a flow cytometry methodology capable of detecting protein concentrations over a range of five orders of magnitude or more.

3. The method of claim 2, wherein the PrP$^{Sc}$ protein is present in the sample in a concentration of 1×10$^3$ particles/ml or less.

4. The method of claim 1, wherein the hydrolyzing agent is a protease and the temperature is a temperature of above 80° C.

5. The method of claim 1, wherein the treatment is carried out using a temperature above 80° C. in a solution at a pH above about 12.0.

6. The method of claim 1, wherein amounts of total PrP$^{Sc}$ are determined using methodology capable of deleting protein concentrations over a range of five orders of magnitude or more.

7. The method of claim 1, wherein the amount of total PrP$^{Sc}$ and treatment insensitive PrP27–30 are determined using time-resolved dissociation enhanced fluorescence.

8. The method of claim 1, wherein the amount of total PrP$^{Sc}$ and treatment insensitive PrP 27–30 are determined using a dual wavelength, laser driven fluorometer.

9. The method of claim 1, wherein the sample is obtained from a cow.

10. The method of claim 1, wherein determining the total amount of PrP$^{Sc}$ in a unit amount of sample is carried out by:

providing a sample suspected of containing a PrP protein which assumes a first conformation and a second, disease related conformation;

dividing the sample into a first portion and a second portion;

contacting the first portion with a labeled antibody which binds to the PrP protein in its first conformation with a higher degree of affinity than it binds to the PrP protein in its second, disease related conformation;

treating the second portion in a manner which causes any PrP protein in the second, disease related conformation to assume a different conformation which conformation has a higher degree of affinity for the labeled antibody as compared to the affinity for the PrP protein in the second disease related conformation;

contacting the second portion with the labeled antibody;

determining the level of binding of labeled antibody to PrP protein in the first portion;

determining the level of binding of labeled antibody to PrP protein in the second portion; and comparing the level of binding of labeled antibody to PrP protein in the first portion with the level in the second portion and thereby determining the total amount of PrP$^{Sc}$ protein in the sample.

11. The method of claim 10, further comprising:

binding PrP protein of the first portion to a first solid support surface; and binding PrP protein of the second portion to a second solid support surface.

12. The method of claim 10, wherein the treating is carried out by subjecting the second portion to a treatment selected from the group consisting of heat, pressure and chemical exposure in order to convert at least 2% of any PrP protein in the second disease related conformation to the different conformation.

13. The method of claim 10, wherein the labeled antibody has at least four times greater affinity for the PrP protein in the first conformation than for the PrP protein in the second conformation.

14. The method of claim 10, wherein the labeled antibody has at least fifteen times greater affinity for the PrP protein in the first conformation than for the PrP protein in the second conformation.

15. The method of claim 10, wherein the labeled antibody has at least thirty times greater affinity for the PrP protein in the first conformation than for the PrP protein in the second conformation.

16. The method of claim 1, wherein the determining of the total amount of PrP$^{Sc}$ in a unit amount of a sample is carried out by:

providing a sample suspected of containing a PrP protein which assumes a first conformation and a second, disease related conformation;

dividing the sample into a first portion and a second portion;

contacting the first portion with a labeled antibody which binds to the PrP protein in its first conformation with a higher degree of affinity than it binds to the PrP protein in its second, disease related conformation;

treating the second portion in a manner which causes any PrP protein in the second, disease related conformation to assume a different conformation which conformation has a higher degree of affinity for the labeled antibody as compared to the affinity for the PrP protein in the second disease related conformation;

contacting the second portion with the labeled antibody;

determining the levels of binding of labeled antibody to PrP protein in the first portion;

determining the level of binding of labeled antibody to PrP protein in the second portion;

adjusting the determined level of binding of labeled antibody to PrP protein in the second portion to compensate for increasing the affinity of the PrP protein in the first conformation for the antibody resulting from the treating;

subtracting the level of binding of labeled antibody protein in the first portion from the adjusted level of binding of labeled antibody in the second portion to obtain a differential.

17. The method of claim 16, further comprising:

applying the differential to the formulae below wherein the differential is represented by the symbol Δ

$$[PrP]\sim\Delta F_{\beta d}F_d-(F_n*f_{\alpha nd})$$

wherein each of the above variables is provided below:

F—any detectable signal;

$F_n$—signal of protein in native conformation;

$F_{n\alpha}$ and $F_{n\beta}$—signals of native non-disease and disease conformations, respectively;

$F_d$—signal of treated protein;

$F_{d\alpha}$ and $F_{d\beta}$—are the signals of treated non-disease and disease conformations;

$\Delta F_{nd}$—increase of signal in the transition from native to treated state;

$\Delta F_{\alpha nd}$—increase in the signal of non-disease conformation in the transition from native to treated state;

$\Delta F_{\beta nd}$—increase in the signal of disease conformation in the transition from native to treated state;

$f_{\alpha nd}$—correlation factor for the transition from native to treated state of non-disease conformation;

$[PrP_\beta]$.—concentration of protein in disease conformation;

∼—is proportional to;

*—multiply by.

18. A method of determining a strain of PrP$^{Sc}$ in a sample, comprising:

determining the total amount of PrP$^{Sc}$ in a unit amount of a sample;

subjecting the sample to limited protease treatment with proteinase K under conditions sufficient to hydrolyze substantially all protein in the sample except for protease insensitive PrP 27–30;

determining the amount of treatment insensitive PrP 27–30 in a unit amount of sample subjected to proteinase K treatment; and subtracting the amounts of treatment insensitive PrP 27–30 from the total amount of PrP$^{Sc}$ to obtain the amount of treatment sensitive PrP$^{Sc}$ in the sample;

determining the ratio of treatment sensitive disease PrP$^{Sc}$ to total PrP$^{Sc}$ protein; and comparing the determined ratio to a known ratio of a known strain of PrP$^{Sc}$ protein to thereby determine the strain of PrP$^{Sc}$ protein in the sample wherein the known strain of PrP$^{Sc}$ is of a strain selected from the group consisting of: Drowsy, 139H, Hyper, Me7, MT-C5, RML and Sc237.

19. The method of claim 18, wherein amounts of total PrP$^{Sc}$ are determined using methodology capable of deleting protein concentrations over a range of five orders of magnitude or more.

20. The method of claim 18, wherein the amount of total PrP$^{Sc}$ and treatment insensitive PrP 27–30 are determined using time-resolved dissociation enhanced fluorescence.

21. The method of claim 18, wherein the amount of total PrP$^{Sc}$ and treatment insensitive PrP 27–30 are determined using a dual wavelength, laser driven fluorometer.

22. A method of determining a strain of PrP$^{Sc}$ in a sample, comprising:

determining the total amount of PrP$^{Sc}$ in a unit amount of a sample;

subjecting the sample to limited protease treatment with proteinase K under conditions sufficient to hydrolyze substantially all protein in the sample except for protease insensitive PrP 27–30;

determining the amount of treatment insensitive PrP 27–30 in a unit amount of sample subjected to proteinase K treatment; and subtracting the amounts of treatment insensitive PrP 27–30 from the total amount of PrP$^{Sc}$ to obtain the amount of treatment sensitive PrP$^{Sc}$ in the sample;

determining the ratios of treatment sensitive PrP$^{Sc}$ to total PrP$^{Sc}$; and comparing the determined ratio to a known ratio of a known strain of PrP$^{Sc}$ to thereby determine the strain and incubation time of PrP$^{Sc}$ in the sample.

23. A method of determining a strain of PrP$^{Sc}$ in a sample, comprising:

determining the total amount of PrP$^{Sc}$ in a unit amount of a sample;

subjecting the sample to limited protease treatment with proteinase K under conditions sufficient to hydrolyze substantially all protein in the sample except for protease insensitive PrP 27–30;

determining the amount of treatment insensitive PrP 27–30 in a unit amount of sample subjected to proteinase K treatment; and subtracting the amounts of treatment insensitive PrP 27–30 from the total amount of PrP$^{Sc}$ to obtain the amount of treatment sensitive PrP$^{Sc}$ in the sample; and plotting the amount of protease sensitive PrP$^{Sc}$ in a unit amount of sample on a graph of incubation time versus amount of sensitive PrP$^{Sc}$ in a unit amount of sample which graph includes plotted data of known strains of PrP$^{Sc}$ and thereby determining the incubation time of the strain and incubation time of PrP$^{Sc}$ in the sample.

24. The method of claim 18, wherein the sample is obtained from a cow.

25. The method of claim 18, wherein determining the total amount of PrP$^{Sc}$ in a unit amount of sample is carried out by:

providing a sample suspected of containing a PrP protein which assumes a first conformation and a second, disease related conformation;

dividing the sample into a first portion and a second portion;

contacting the first portion with a labeled antibody which binds to the PrP protein in its first conformation with a higher degree of affinity than it binds to the PrP protein in its second, disease related conformation;

treating the second portion in a manner which causes any PrP protein in the second, disease related conformation to assume a different conformation which conformation has a higher degree of affinity for the labeled antibody as compared to the affinity for the PrP protein in the second disease related conformation;

contacting the second portion with the labeled antibody;

determining the level of binding of labeled antibody to PrP protein in the first portion;

determining the level of binding of labeled antibody to PrP protein in the second portion; and comparing the level of binding of labeled antibody to PrP protein in the first portion with the level in the second portion and thereby determining the total amount of PrP$^{Sc}$ protein in the sample.

26. The method of claim 25, further comprising:

binding PrP protein of the first portion to a first solid support surface; and binding PrP protein of the second portion to a second solid support surface.

27. The method of claim 25, wherein the treating is carried out by subjecting the second portion to a treatment selected from the group consisting of heat, pressure and chemical exposure in order to convert at least 2% of any PrP protein in the second disease related conformation to the different conformation.

28. The method of claim 25, wherein the labeled antibody has at least four times greater affinity for the PrP protein in the first conformation than for the PrP protein in the second conformation.

29. The method of claim 25, wherein the labeled antibody has at least fifteen times greater affinity for the PrP protein in the first conformation than for the PrP protein in the second conformation.

30. The method of claim 25, wherein the labeled antibody has at least thirty times greater affinity for the PrP protein in the first conformation than for the PrP protein in the second conformation.

31. The method of claim 18, wherein the determining of the total amount of PrP$^{Sc}$ in a unit amount of a sample is carried out by:

providing a sample suspected of containing a PrP protein which assumes a first conformation and a second, disease related conformation;

dividing the sample into a first portion and a second portion;

contacting the first portion with a labeled antibody which binds to the PrP protein in its first conformation with a higher degree of affinity than it binds to the PrP protein in its second, disease related conformation;

treating the second portion in a manner which causes any PrP protein in the second, disease related conformation to assume a different conformation which conformation has a higher degree of affinity for the labeled antibody as compared to the affinity for the PrP protein in the second disease related conformation;

contacting the second portion with the labeled antibody;

determining the levels of binding of labeled antibody to PrP protein in the first portion;

determining the level of binding of labeled antibody to PrP protein in the second portion;

adjusting the determined level of binding of labeled antibody to PrP protein in the second portion to compensate for increasing the affinity of the PrP protein in the first conformation for the antibody resulting from the treating;

subtracting the level of binding of labeled antibody protein in the first portion from the adjusted level of binding of labeled antibody in the second portion to obtain a differential.

32. The method of claim 31, further comprising:

applying the differential to the formulae below wherein the differential is represented by the symbol $\Delta$ $$[PrP] \sim \Delta F_{\beta \rightarrow d} F_d - (F_n * f_{\alpha n \rightarrow d})$$

wherein each of the above variables is provided below:

F—any detectable signal;

$F_n$—signal of protein in native conformation;

$F_{n\alpha}$ and $F_{n\beta}$—signals of native non-disease and disease conformations, respectively;

$F_d$—signal of treated protein;

$F_{d\alpha}$ and $F_{d\beta}$—are the signals of treated non-disease and disease conformations;

$\Delta F_{n \rightarrow d}$—increase of signal in the transition from native to treated state;

$\Delta F_{\alpha n \rightarrow d}$—increase in the signal of non-disease conformation in the transition from native to treated state;

$\Delta F_{\beta n \rightarrow d}$—increase in the signal of disease conformation in the transition from native to treated state;

$f_{\alpha n \rightarrow d}$—correlation factor for the transition from native to treated state of non-disease conformation;

$[PrP_\beta]$—concentration of protein in disease conformation;

~—is proportional to;

*—multiply by.

* * * * *